(12) United States Patent
Yano et al.

(10) Patent No.: US 7,452,960 B2
(45) Date of Patent: Nov. 18, 2008

(54) POLYHYDROXYALKANOATE COPOLYMER, RESIN COMPOSITION, MOLDED PRODUCT, TONER, IMAGE FORMING METHOD AND IMAGE FORMING APPARATUS

(75) Inventors: Tetsuya Yano, Atsugi (JP); Chieko Mihara, Isehara (JP); Shinya Kozaki, Tokyo (JP); Tsutomu Honma, Atsugi (JP); Takashi Kenmoku, Fujisawa (JP); Tatsuki Fukui, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 189 days.

(21) Appl. No.: 10/532,136

(22) PCT Filed: Oct. 24, 2003

(86) PCT No.: PCT/JP03/13604

§ 371 (c)(1),
(2), (4) Date: Apr. 20, 2005

(87) PCT Pub. No.: WO2004/041905

PCT Pub. Date: May 21, 2004

(65) Prior Publication Data

US 2006/0040196 A1   Feb. 23, 2006

(30) Foreign Application Priority Data

| Oct. 24, 2002 | (JP) | ............................. 2002-309785 |
| Mar. 28, 2003 | (JP) | ............................. 2003-092235 |
| Mar. 28, 2003 | (JP) | ............................. 2003-092515 |
| Mar. 28, 2003 | (JP) | ............................. 2003-092558 |
| Oct. 16, 2003 | (JP) | ............................. 2003-357051 |

(51) Int. Cl.
G03G 9/00 (2006.01)
C12P 11/00 (2006.01)

(52) U.S. Cl. ................... 528/361; 528/363; 528/364; 428/108; 428/110; 428/127; 428/137; 435/130; 435/132; 435/136

(58) Field of Classification Search .................. None
See application file for complete search history.

(56) References Cited

U.S. PATENT DOCUMENTS

| 4,393,167 | A | 7/1983 | Holmes et al. ............... 525/64 |
| 4,876,331 | A | 10/1989 | Doi ............................. 528/361 |
| 5,004,664 | A | 4/1991 | Fuller et al. ............... 430/106.6 |
| 5,135,859 | A | 8/1992 | Witholt et al. ............... 435/135 |
| 5,200,332 | A | 4/1993 | Yamane et al. ............... 435/135 |
| 5,292,860 | A | 3/1994 | Shiotani et al. ............. 528/361 |
| 5,334,698 | A | 8/1994 | Witholt et al. ............... 528/354 |
| 5,667,927 | A | 9/1997 | Kubota et al. ............... 430/109 |
| 6,191,203 | B1 | 2/2001 | Asrar et al. |
| 6,221,316 | B1 | 4/2001 | Hänggi et al. ............... 422/102 |
| 6,645,743 | B1 * | 11/2003 | Honma et al. ............... 435/146 |
| 6,808,854 | B2 * | 10/2004 | Imamura et al. ........... 430/110.1 |

| 2003/0013841 | A1 | 1/2003 | Imamura et al. |
| 2003/0096182 | A1 | 5/2003 | Yano et al. |
| 2003/0100700 | A1 * | 5/2003 | Imamura et al. ............ 528/272 |
| 2003/0104300 | A1 | 6/2003 | Kenmoku et al. |
| 2003/0204044 | A1 | 10/2003 | Honma et al. |
| 2005/0250191 | A1 | 11/2005 | Imamura et al. ............ 435/135 |

FOREIGN PATENT DOCUMENTS

| EP | 1236755 | A2 | 9/2002 |
| EP | 1245605 | A2 | 10/2002 |
| EP | 1253161 | A2 | 10/2002 |
| EP | 1253162 | A2 | 10/2002 |
| EP | 1340778 | A1 | 9/2003 |
| JP | 59-190945 | | 10/1984 |
| JP | 05-7492 | | 1/1993 |
| JP | 05-93049 | | 4/1993 |
| JP | 06-15604 | | 3/1994 |
| JP | 06-289644 | | 10/1994 |
| JP | 07-14352 | | 2/1995 |
| JP | 07-120975 | | 5/1995 |

(Continued)

OTHER PUBLICATIONS

Data base WPI Section Ch, Week 1992, Derwent Publications, AN-1992-263777, XP-002266760 for JP04-179967, Jun. 1992.

(Continued)

*Primary Examiner*—Vasu Jagannathan
*Assistant Examiner*—Gennadiy Mesh
(74) *Attorney, Agent, or Firm*—Fitzpatrick, Cella, Harper & Scinto

(57) ABSTRACT

A polyhydroxyalkanoate copolymer comprises one kind of unit of $$-[OCH((CH_2)_x-SOC_6H_5R)CH_2CO]-\ (n=1\text{-}7) \quad (1)$$

(wherein R is any one of H, halogen, CN, $NO_2$, COOR', $SO_2R''$ (R' is any one of H, Na, K, $CH_3$ and $C_2H_5$; R" is any one of OH, ONa, OK, halogen, $OCH_3$ and $OC_2H_5$), $CH_3$, $C_2H_5$, $C_3H_7$, $(CH_3)_2$—CH and $(CH_3)_3$—C) and $$-[OCH((CH_2)_x-SO_2C_6H_5R)CH_2CO]-\ (n=1\text{-}7) \quad (2)$$

(wherein R is any one of H, halogen, CN, $NO_2$, COO R', $SO_2R''$ (R' is any one of H, Na, K, $CH_3$ and $C_2H_5$; R" is any one of OH, ONa, OK, halogen, $OCH_3$ and $OC_2H_5$), $CH_3$, $C_2H_5$, $C_3H_7$, $(CH_3)_2$—CH and $(CH_3)_3$—C) and at least one unit of chemical formulae (3) to (6):

$$-[OCH((CH_2)_m-Rz)CH_2CO]-\ (n=1\text{-}8) \quad (3)$$

(wherein Rz comprises a residue having either a phenyl structure or a thienyl structure), $$-[OCH((CH_2)_k-C_6H_{11}Ra)CH_2CO]-\ (n=1\text{-}8) \quad (4)$$

(wherein $R_a$ is any one of H, CN, $NO_2$, halogen, $CH_3$, $C_2H_5$, $C_3H_7$, $CF_3$, $C_2F_5$ and $C_3F_7$)

$$-[OCH((CH_2)_n-CH=CH_2)CH_2CO]-\ (n=1\text{-}8),$$
and $\quad (5)$ $$-[OCH((CH_2)_n-COORb)CH_2CO]-\ (n=1\text{-}8) \quad (6)$$

(wherein $R_b$ is any one of H, Na and K).

3 Claims, 21 Drawing Sheets

FOREIGN PATENT DOCUMENTS

| | | |
|---|---|---|
| JP | 07-265065 | 10/1995 |
| JP | 08-19227 | 2/1996 |
| JP | 08-262796 | 10/1996 |
| JP | 2642937 | 5/1997 |
| JP | 09-191893 | 7/1997 |
| JP | 09-274335 | 10/1997 |
| JP | 09-281746 | 10/1997 |
| JP | 2989175 | 10/1999 |
| JP | 2002-080751 | 3/2002 |
| WO | WO 97/34953 | 9/1997 |
| WO | WO 99/23161 | 5/1999 |

OTHER PUBLICATIONS

Takagi et al. "Biosynthesis of Polyhydroxyalkanoate . . . *Pseudomonas putida*", Macromolecules, vol. 32, 8315-8318 (1999).

Vogel, et al.; "Acetylornithinase of *Escherichia coli:* . . . properties"; J. Biol. Chem., vol. 218, pp. 97-106 (1956).

Stille, et al.; "Tetracyclic Dienes. I. The Diels-Alder . . . Cyclopentadiene"; J. Am. Chem. Soc., vol. 81, pp. 4273-4275 (1959).

Briggs, et al.; "Degradation of the Lanosterol Side-chain"; J. Chem. Soc., Perkin Trans. I; pp. 806-809 (1973).

Fritzsche, et al.; "An unusual bacterial polyester . . . group"; Makromol. Chem., vol. 191, pp. 1957-1965 (1990).

Kim, et al.; "Preparation and Characterization of Polyβ-hydroxyalkanoates) . . . n-Alkanoic Acids"; Macromolecules, vol. 24, pp. 5256-5260 (1991).

Antoun, et al., "Production of a Chiral Polyester . . . Pentadienoic Acid"; Chirality, vol. 3, No. 6, pp. 492-494 (1991).

Kim, et al.; "Poly(β-hydroxyalkanoate) Copolymers . . . *oleovorans*"; Macromolecules, vol. 25, pp. 1852-1857 (1992).

Ramsay, et al.; "Effect on Nitrogen Limitation . . . *resinovorans*"; Appl. & Environ. Microbiol., vol. 58, No. 2, pp. 744-746 (1992).

G. J. M. de Koning, et al.; "A biodegradable rubber . . . *oleovorans*"; Polymer, vol. 35, No. 10, pp. 2090-2097 (1994).

Ritter, et al.; "Bacterical production of polyesters . . . in the side chains, 1"; Macromol. Chem. Phys., vol. 195, pp. 1665-1672 (1994).

Kim, et al., "Bioengineering of polyβ-hydroxyalkanoates) . . . substituents", Can. J. Microbiol., vol. 41, Suppl. 1, pp. 32-43 (1995).

Kim, et al.; "Poly-3-hydroxyalkanoates Produced . . . ω-Phenoxyalkanoates"; Macromolecules, vol. 29, pp. 3432-3435 (1996).

Curley, et al.; "Production of Poly(3-hydroxyalkanoates) . . . *oleovorans*"; Macrololecules, vol. 29, pp. 1762-1766 (1996).

Gross, et al.; "Cyanophenoxy-containing microbial . . . Biodegradability"; Polymer Intern., vol. 39, pp. 205-213 (1996).

Andujar, et al.; "Polyesters Produced by Pseudomonas . . . Groups"; Macromolecules, vol. 30, pp. 1611-1615 (1997).

Park, et al.; "Epoxidation of Bacterial Polyesters . . . 10-Undecenoic Acid"; Macromolecules, vol. 31, pp. 1480-1486 (1998).

Constantin, et al.; "Chemical modification of . . . sugars"; Macromol. Rapid Commun., vol. 20, pp. 91-94 (1999).

Arostegui, et al., "Bacterial Polyesters . . . groups"; Macromolecules, vol. 32, pp. 2889-2895 (1999).

Takagi, et al., "Biosynthesis of Polyhydroxyalkanoate . . . *putida*"; Macromolecules, vol. 32, pp. 8315-8318 (1999).

Lee, et al.; "Hydrophilic bacterial polyesters . . . groups"; Polymer, vol. 41, pp. 1703-1709 (2000).

Bear, et al.; "Preparation of . . . side chains", C.R. Acad. Sci. Paris, Chimie/Chemistry, vol. 4, pp. 289-293 (2001).

\* cited by examiner

POLYHYDROXYALKANOATE COPOLYMER, RESIN COMPOSITION, MOLDED PRODUCT, TONER, IMAGE FORMING METHOD AND IMAGE FORMING APPARATUS

TECHNICAL FIELD

The present invention relates to a polyhydroxyalkanoate copolymer comprising a new unit, a method for producing a precursor thereof using microorganisms, and a method for producing the copolymer by oxidization of the precursor. Moreover, the present invention relates to a resin composition, a molded article obtained by using the same, and a production method thereof. Furthermore, the present invention relates to a binder resin that can be used for a toner for development of an electrostatic latent image, which is used in recording methods such as the electrophotography, electrostatic recording method, or magnetic recording method, a toner used for electrostatic latent image development, an image forming method using the toner, and an image forming apparatus using the toner.

BACKGROUND ART

Background Art of Resin (Problems Regarding the Conventionally Used Resin)

Plastics such as a polyethylene terephthalate (PET) resin, polyester resin, vinyl chloride resin or polyolefin resin have previously been used for a wide range of uses as molded articles, e.g., containers such as food containers, beverage bottles, cosmetic containers or plant pots.

The majority of these plastics are discarded after use. The plastic wastes have previously been disposed by incineration or landfilling. However, since the wastes generate a great burning energy by incineration, they have problems such as regarding the durability of incinerators caused by a high burning temperature, processing cost by high temperature durable incinerators, and air pollution caused by generation of toxic combustion gas such as carbon monoxide, sulfur compounds, chlorine gas or dioxin. In addition, when the plastic wastes are landfilled, they remain without being decomposed on a semi-permanent basis, and they are accumulated as wastes in a disposal field, thereby causing a social problem that is called a waste problem. Moreover, since the plastic wastes exist as are in the earth, they cause a problem regarding instability of the ground in a landfill site, and there is also a risk that the wastes might affect the natural environment and various types of organisms in the landfill site or the peripheral area.

Thus, to solve these problems, a biodegradable resin has become a focus of attention in these years. The term "biodegradable resin" is used herein to mean a resin, which has physical properties almost equivalent to those of general-purpose plastics during the use as a material, but after the use, is rapidly decomposed by microorganisms in the natural environment such as on the earth, in the earth, in the compost, in the active slurry, or in the water. The resin is decomposed into a fine form, and several types of biodegradable resins are finally converted into carbon dioxide and water.

Other than specific polyester biodegradable resins, blended resin compositions have conventionally been known to satisfy the above described requirements, and examples of such blended resin compositions include a starch-ethylene vinyl alcohol copolymer resin, an ethylene vinyl alcohol copolymer resin-aliphatic polyester resin, and an aliphatic polyester resin-polyolefin resin. These resins or resin compositions are molded into various forms such as a bottle and are in practical use. However, a resin composition, which is excellent in moldability required in its production process, as well as various physical properties required as containers and biodegradability required after being discarded, has not yet been proposed. For example, a resin composition having both biodegradability and heat resistance in a molding process has not yet been accomplished.

(Concerning Polyhydroxyalkanoate (PHA))

By the way, in recent years, as a method for solving the problem regarding environmental contamination caused by wastes such as plastic molded articles, the use of a biodegradable resin synthesized by microorganisms as a molding material has been proposed. Examples of known biodegradable resins derived from microorganisms include polyhydroxyalkanoate (hereinafter referred to as PHA at times) such as a copolymer (hereinafter referred to as PHB/V) of poly-3-hydroxy-n-butyric acid (hereinafter referred to as PHB at times) or 3-hydroxy-n-butyric acid (hereinafter referred to as 3HB at times) and 3-hydroxy-n-valeric acid (hereinafter referred to as 3HV at times), polysaccharide such as bacteria cellulose or Pullulan, and polyamino acid such as poly-γ-glutamic acid or polylysine. In particular, PHA is, as with the conventional plastics, used for various products after undergoing a melt-processing. Further, since PHA is excellent in biodegradability, it is expected that this compound will be applied to soft components for medical use, etc.

It has hitherto been reported that many microorganisms produce poly-3-hydroxybutyric acid (PHB) or other PHAs and accumulate it in the cell. Like conventional plastics, these polymers can be utilized for the production of various products by melt processing or the like. Also, since they are biodegradable, they have an advantage of being completely broken down by microorganisms in the natural world, and by no means remain in natural environment to cause pollution unlike many conventional synthetic polymeric compounds.

It is known that such PHAs produced by microorganisms may have various compositions and structures depending on types of microorganisms used for its production, the composition of culture medium, the conditions for culture and so forth. Researches on how to control such compositions and structures have hitherto chiefly been made from the viewpoint of the improvement in physical properties of PHAs.

(1) Especially, biosynthesis of PHA obtained by polymerization of a monomer units with a relatively simple structure such as 3HB, 3HV, 3-hydroxyhexanoic acid (hereinafter referred to as 3HHx) and 4-hyddroxy-n-butyric acid (hereinafter referred to as 4HB) have been studied, and production using various microorganisms has been reported (Japanese Patent Publications Nos. 6-15604, 7-14352 and 8-19227; Japanese Patent Application Laid-Open Nos. 5-7492, 5-93049, 7-265065 and 9-191893; Japanese Patent No. 2642937 and Appl. Environ. Microbiol., 58(2), 746, 1992).

(2) When, however, broader application of such PHAs produced by microorganisms, e.g., application as functional polymers is taken into account, a PHA in which a substituent other than an alkyl group has been introduced in the side chain, i.e., "unusual PHA" is expected to be very useful. Examples of such a substituent may include those containing aromatic rings (such as a phenyl group and a phenoxy group), and unsaturated hydrocarbons, an ester group, an allyl group, a cyano group, halogenated hydrocarbons and epoxides.

For example, there are reports on production of: PHA containing a phenyl group or its partially substituted group such as PHA containing 3-hydroxy-5-phenylvaleric acid as a unit using 5-phenylvaleric acid as a substrate (Makromol.

Chem. Phys., 191, 1957-1965 (1990); Macromolecules, 24, 5256-5260 (1991) and Chirality, 3, 492-494 (1991)), PHA containing 3-hydroxy-5-(4'-tolyl) valeric acid as a unit using 5-(4'-tolyl) valeric acid as a substrate (Macromolecules, 29, 1762-1766 (1996)), and PHA containing 3-hydroxy-5-(2', 4'-dinitrophenyl) valeric acid and 3-hydroxy-5-(4'-nitrophenyl) valeric acid as a unit using 5-(2', 4'-dinitrophenyl) valeric acid as a substrate (Macromolecules, 32, 2889-2895 (1999)); PHA containing a phenoxy group or its partially substituted group such as PHA copolymer containing 3-hydroxy-5-phenoxyvaleric acid and 3-hydroxy-9-phenoxynonanoic acid using 11-pheoxyundecanoic acid as a substrate (Macromol. Chem. Phys., 195, 1665-1672 (1994)), PHA containing a 3-hydroxy-4-phenoxybutyric acid unit and a 3-hydroxy-6-phenoxyhexanoic acid unit from 6-phenoxyhexanoic acid, PHA containing a 3-hydroxy-4-phenoxybutyric acid unit, a 3-hydroxy-6-phenoxyhexanoic acid unit, and a 3-hydroxy-8-phenoxyoctanoic acid unit from 8-phenoxyoctanoic acid, and PHA containing a 3-hydroxy-5-phenoxyvaleric acid unit and a 3-hydroxy-7-phenoxyheptanoic acid unit from 11-phenoxyundecanoic acid (Macromolecules, 29, 3432-3435 (1996)). There is also a report (Japanese Patent No. 2989175) on a homopolymer consisting of 3-hydroxy-5-(monofluorophenoxy) pentanoate (3H5(MFP)P) units or 3-hydroxy-5-(difluorophenoxy) pentanoate (3H5(DFP)P) units, and a PHA copolymer containing at least (3H5(MFP)P) units or (3H5(DFP)P) units, of which advantage is to provide stereoregularity and water repellency while maintaining a high melting point and good processability.

Further, studies are conducted on cyano-substituents and nitro-substituents in addition to the fluorine-substituent described above. For example, PHA containing 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as substrates (Can. J. Microbiol., 41, 32-43 (1995); and Polymer International, 39, 205-213 (1996)).

These reports are useful in obtaining polymers each having an aromatic ring in the side chain of PHA and having properties derived therefrom unlike general PHA whose side chain contains an alkyl group. Further, as the example of unusual-PHA having a cyclohexyl group, production of PHA from cyclohexylbutyric acid or cyclohexylvaleric acid has been reported (Macromolecules, 30, 1611-1615 (1997)).

(3) Without being confined merely to changes in physical properties, research in a new category is being conducted to produce a PHA having a suitable functional group in the side chain.

For example, a study has been made to produce a PHA having, in a unit thereof, an active group having high reactivity in an addition reaction, such as a bromo group or vinyl group, and to introduce any given functional group into the side chain of the polymer by chemical transformation using the above active group, so as to obtain a multifunctional PHA.

As an example of synthesizing a PHA containing a unit having a thioether (—S—; a sulfanyl linkage), which is expected to provide a high reactivity, Macromolecules, 32, 8315-8318 (1999) reports that *Pseudomonas putida* strain 27N01 produces a PHA copolymer of 3-hydroxy-5-thiophenoxyvaleric acid (3-hydroxy-5-(phenylsulfanyl)valeric acid) with 3-hydroxy-7-thiophenoxyheptanoic acid (3-hydroxy-7-(phenylsulfanyl)heptanoic acid), using 11-thiophenoxyundecanoic acid (11-(phenylsulfanyl)undecanoic acid) as a substrate.

Macromol. Rapid Commun., 20, 91-94 (1999) has reported that using *Pseudomonas oleovorans*, a PHA having a bromo group on a side chain thereof is produced, and then the side chain is modified with the thiol product of an acetylated maltose, so as to synthesize PHAs having different solubility and hydrophilicity.

It is reported in Polymer, 41, 1703-1709 (2000) that a change of solubility in solvents has been found such that 3-hydroxyalkanoic acid having diol on the side chain terminal, synthesized by an oxidation reaction using potassium permanganate after producing PHA containing as a monomer unit 3-hydroxyalkenoic acid having an unsaturated bond in the terminal of the side chain terminal using 10-undecenoic acid as a substrate, is rendered soluble in polar solvents such as methanol, acetone-water mixture (80/20, v/v) and dimethylsulfoxide, and insoluble in nonpolar solvents such as chloroform, tetrahydrofuran and acetone.

Likewise, Macromolecules, 31, 1480-1486 (1998) has reported that using *Pseudomonas oleovorans,* polyester having a vinyl group on a side chain thereof is produced, and then the vinyl group is epoxidized, so as to produce polyester having an epoxy group on a side chain thereof.

Moreover, Polymer, 35, 2090-2097 (1994) has reported that using a vinyl group on the side chain of polyester, a crosslinking reaction is carried out in the polyester molecule, so as to improve the properties of the polyester.

It is reported in Macromolecular chemistry, 4, 289-293 (2001) that an improvement in speed of decomposition has been found for PHA containing 3-hydroxy-10-carboxydecanoic acid as a monomer unit, synthesized by an oxidization cleavage reaction using potassium permanganate after producing PHA containing as a monomer unit 3-hydroxy-10-undecenoic acid using 10-undecenoic acid as a substrate.

At the same time, in order to change the physical properties of a PHA having an active group in its unit and to actually use it as a polymer, the synthesis of a PHA copolymer comprising units other than units having active groups by using microorganisms has been studied. Macromolecules, 25, 1852-1857 (1992) has reported that using *Pseudomonas oleovorans,* a PHA copolymer comprising a 3-hydroxy-ω-bromoalkanoic acid unit and a straight-chain alkanoic acid unit has been produced in the coexistence of ω-bromoalkanoic acid and n-nonanoic acid, such as 11-bromoundecanoic acid, 8-bromooctanoic acid and 6-bromohexanoic acid.

Thus, into a PHA having, in its units, active groups with high reactivity, such as a bromo or vinyl group, various functional groups can be introduced. Or, chemical transformation can also be performed on such a PHA. Moreover, since a PHA having an active group can be a crosslink point of a polymer, it can be said that such a PHA is extremely effective to achieve multifunctionality of a PHA.

Background Art of Toner

A large number of electrophotographic methods have been known so far. In general, copied images are obtained by forming an electrostatic latent image on an image-bearing member (photosensitive member) by utilizing a photoconductive material and by various means, subsequently developing the latent image by the use of a toner to form a visible image (toner image), transferring the toner image to a transfer medium as the occasion demands, then fixing the toner image to the transfer medium by heating and/or pressing. As methods by which the electrostatic latent image is formed into a visible image, cascade development, magnetic brush development, pressure development and so forth are known in the art. Another method is also known in which, using a magnetic toner and a rotary developing sleeve provided with magnetic poles at the core, the magnetic toner is caused to fly from the developing sleeve to the photosensitive member by the aid of an electric field.

As development methods used when electrostatic latent images are developed, available are a two-component development method making use of a two-component type developer comprised of a toner and a carrier and a one-component development method making use of a one-component developer using no carrier and comprised of only a toner.

Fine colored particles commonly called a toner are composed of a binder resin and a colorant as essential components and optionally a magnetic material and so forth.

(Concerning Binder Resin)

Binder resin is made up of a major part of toner. Accordingly, the physical properties of a binder resin have a great effect on the physical properties of the toner. For example, a binder resin is required to have delicate hardness and hot-melt properties. Toner obtained by crushing and classifying a binder resin containing a dispersed coloring agent or the like is required to show good flowability, without generating fine particles by mechanical impulse generated as a result of stirring in a development apparatus or without aggregation of the toner itself. Moreover, it is required that a toner is quickly melted at a low temperature when it is fixed, and that the melted toner shows cohesiveness when it is melted. This is to say, it is possible to control the physical properties of a toner by controlling the physical properties of a binder resin.

As binder resins, a styrene-acrylic ester copolymer, a polyester resin, an epoxy resin, an olefin resin and others have conventionally been used. Of these, a polyester resin is now widely used as a resin for heat-roll fixing for the reasons that when it is melted, the dispersion of toner additives such as carbon black or wetting into a transfer paper progresses favorably, and that it is also excellent in fixability.

Moreover, from the viewpoint of environmental protection, recently, people worldwide are more aware of the recycling of source, the reduction of wastes and the improvement of safety of wastes than ever. The above objects should be achieved also in the field of electrophotography. That is, with the diffusion of copying machines and printers, the wasted amount of a toner fixed on a paper, a used waste toner, and printed papers has increased year by year. Since the constitutional components of the conventional toner are all stable artificial compounds, the conventional toner is persistent, and in some cases, it remains for a long time in any type of the environment such as in the earth or in the water. Furthermore, recycling and reusing of ordinary papers is an important object for recycling source. However, when the conventional binder resins including a styrene resin as a typical example are used for a toner, it is difficult to deink it by alkali hydrolysis, and therefore, this is one of the objects for recycling ordinary papers. Still further, from the viewpoint of protection of terrestrial environment and influence on the human body, safety of wastes is also an important object.

(Application of Biodegradable Resin to Toner)

In the field of electrophotography also, a method of using a biodegradable resin as a binder resin has been proposed to achieve a toner causing no environmental contamination when it is discarded.

Japanese Patent Application Laid-Open No. 6-289644 disclose an electrophotographic toner particularly used for heat-roll fixing, which is characterized in that at least a binder resin contains a vegetable wax and a biodegradable resin (as exemplified by polyesters produced by microorganisms and natural polymeric materials derived from vegetables or animals), and the vegetable wax is added to the binder resin in an amount of from 5 to 50% by weight.

Japanese Patent Application Laid-Open No. 8-262796 discloses an electrophotographic toner containing a binder resin and a colorant, and is characterized in that the binder resin comprises a biodegradable resin (as exemplified by aliphatic polyester resins) and the colorant comprises a water-insoluble coloring matter.

Moreover, U.S. Pat. No. 5,004,664 discloses a toner comprising, as a composition, a biodegradable resin, especially, polyhydroxybutyric acid, polyhydroxyvaleric acid, a copolymer thereof, or a blended form thereof.

In these techniques, binder resins have problems regarding their essential functions. For example, since binder resins are biodegradable, when a toner containing such resins is landfilled, it is certainly decomposed in the earth, but it has low durability. Moreover, high hygroscopicity of these binder resins results in unstable electrical charge. For example, PHB is a hard brittle material with properties such as a melting point of 180° C., a degree of crystallinity between 50% and 70%, a Young's modulus of 3.5 Gpa, and a breaking extension of 5%, and so it is unsatisfactory to be practically used as a binder resin for a toner.

Toner comprising polylactic acid aliphatic polyester as a main component has been disclosed for the reason that the toner has biodegradability and is efficiently decomposed by alkali hydrolysis so that it is useful for recycling of papers. For example, Japanese Patent Application Laid-Open No. 7-120975 has proposed a method for preparing a toner from a lactic acid homopolymer, and polylactic acid obtained by ring-opening polymerization has been described therein as a typical example.

In the ring-opening polymerization, lactic acid is once oligomerized by dehydration, the oligomerized product is then converted into a cyclic dimer lactide by depolymerization, and it is then subjected to ring-opening polymerization. Since this method comprises such complicated steps, the obtained polylactic acid used as a resin for a toner is extremely expensive.

Moreover, since the above ring-opening polymerization is a cationic ring-opening polymerization, used solvents should be anhydrous compounds, and ionic species as a polymerization terminator should be removed. Thus, since this method has low production efficiency and monomer species used in the production of polyester is limited to a cyclic ester, it is difficult to control physical properties necessary as a resin for a toner. Furthermore, it is also difficult to copolymerize with various monomers to control the balance between degradability and physical properties. Accordingly, a low-cost degradable polyester whose physical properties are easily controlled is desired. When a toner is directly produced from polylactic acid, the obtained toner has problems regarding preservative quality and anti-offset property. Accordingly, it has not yet been in actual use.

Japanese Patent Application Laid-Open No. 9-274335 discloses an electrostatic latent image developing toner characterized in that it contains a polyester resin obtained by dehydrating polycondensation of a composition containing lactic acid and tri- or higher functional oxycarboxylic acid and a coloring agent. However, since the polyester resin is formed through dehydrating polycondensation of an alcohol group in lactic acid and a carboxylic acid group in oxycarboxylic acid, the molecular weight of the obtained resin is likely to increase, and it is therefore considered that biodegradability is lowered. Moreover, as with Japanese Patent Application Laid-Open No. 7-120975, this resin causes problems regarding the preservative quality and anti-offset property of the obtained toner.

Japanese Patent Application Laid-Open No. 9-281746 still also discloses a toner for developing electrostatic latent images which is characterized by containing a urethanated polyester resin and a colorant; the urethanated polyester resin being obtained by cross-linking polylactic acid with a tri- or more functional polybasic isocyanate.

However, this toner also has problems regarding degree of biodegradability, preservative quality and anti-offset property.

Moreover, polycaprolactone that is a representative homopolymer of hydroxycarboxylic acid has a low melting point and a low glass transition point, and is excellent in compatibility with various types of resins. However, since it has a low melting point of 60° C., it is not suitable as a binder resin when it is used singly. Furthermore, polylactic acid has a high glass transition point (60° C.), and crystalline polylactic acid is a thermoplastic polymer having a high melting point (around 180° C.). However, as stated above, it has not yet practically used as a binder resin. Still further, a toner resin consisting of the conventional degradable polyester generally has poor crushability, and therefore it is difficult to use such a toner resin as a binder resin, which makes up 90% of a toner with a particle size of approximately 10 μm. Thus, when considered the commercialization of the above toner resin as a binder resin, the improvement of its physical properties is strongly desired.

In all the electrophotographic toners stated above, biodegradable resins are used as their binder resins, and they are understood to have the effect of contributing to environmental conservation.

(Concerning Other Prior Art Publications)

In the invention of the present application, microorganisms described in Japanese Patent Applications Laid-Open Nos. 2001-288256 and 2002-80571 are used. Description regarding a medium in Non Patent Publication 17 can be incorporated herein by reference. Moreover, J. Chem. Soc., Perkin. Trans. 1, 806 (1973), Org. Synth., 4, 698 (1963), J. Org. Chem., 46, 19 (1981), and J. Am. Chem. Soc., 81, 4273 (1959) describe that carboxylic acid is obtained by cleaving the double bond of carbon-carbon by oxidation with an oxidizing agent.

That is to say, both the conventional plastic molded articles and toner binders for electrophotographic toner comprise, as raw materials, a resin that is not decomposed in the nature and thereby might cause various environmental problems, when it is directly discarded. The used amount of such a resin is increasing year by year. Accordingly, it is strongly desired to take measures against waste treatment quickly.

The previously reported polyester that is obtained by chemical reaction and treatment of polyester having a vinyl group can possess various functions, but since it has a medium or long alkyl chain on a side chain thereof, its thermal property is not necessarily preferable. That is to say, the above polyester has a low glass transition temperature and a low melting point, thereby narrowing the applicable range as a molded article or film.

On the other hand, as stated above, polyester having an aromatic ring on a side chain thereof generally has a character that it has a high melting point and also has a wide applicable range as a molded article or film. However, in general, the above described "unusual PHA" also has a low glass transition temperature (up to approximately 30° C.), and the control of the solubility in a solvent has a certain limit. Accordingly, when various types of application and use of the PHA are considered, the improvement of the thermal property (especially grass transition temperature) and the control of the solubility in a solvent are large problems.

Moreover, in the case of the above reported PHA in which a monomer unit having a carbonyl group, epoxy group or diol group on a side chain terminal is introduced, the copolymer unit is a monomer unit having a straight-chain alkyl group on a side chain thereof, and this polymer has a low glass transition temperature. Further, it is difficult to control the solubility in a solvent only by the monomer unit having the straight-chain alkyl group.

For the above reasons, it is desired to achieve a PHA in which the ratio of a monomer unit can be arbitrarily controlled and its physical properties, especially its thermal property and solubility in a solvent can be arbitrarily controlled, so that the application as a polymer is not limited, and a method for producing the same.

DISCLOSURE OF THE INVENTION

In order to solve the above described problems, the present invention is provided to achieve a polyhydroxyalkanoate-type polyester copolymer having a unit comprising a phenylsulfinyl and/or phenylsulfonyl group that is available for various types of application, and a method for producing the same.

Moreover, the present invention is also provided to achieve a resin composition comprising the above polyhydroxyalkanoate-type polyester or a copolymer thereof, which can prevent various environmental problems caused by wastes, a molded article obtained by using the resin composition, and a method for producing the same. Furthermore, the present invention is also provided to achieve a molded article consisting of a biodegradable resin excellent in extrusion molding property, mechanical property, heat resistance and other properties, and especially a resin composition having both biodegradability and heat resistance when it is molded.

Still further, as stated above, by applying biological engineering means to the production of a resin composition and a molded article, it becomes possible to produce a novel resin composition and a novel molded article, which have been hardly produced by the conventional organic synthetic chemical method. Still further, in the conventional organic synthetic chemical method, the production process consists of multi steps of reactions, but in the present invention, the production process consists of only one step in many cases. Accordingly, the simplification of a production process, cost-reduction, the reduction of time required are also expected. Still further, the present invention also enables the reduction of use of organic solvents, acid, alkali, surfactants and others, the setting of moderate reaction conditions, and synthesis from nonoil materials or raw materials with low purity, thereby realizing an environmentally low burden and source recycling-type synthetic process.

Describing the above synthesis from raw materials with low purity further in detail, since the substrate specificity of enzyme as a catalyst is generally high in a biological engineering synthetic process, although low-purity raw materials are used, it is possible to advance a desired reaction, selectively. Accordingly, this synthetic process can also be expected to be sued for wastes or recycling materials.

What is more, the present invention is provided to achieve: a binder resin comprising the above polyhydroxyalkanoate-type polyester or a copolymer thereof, which is biodegradable, highly contributes to the protection of the natural environment, facilitates the conventional deinking process of using alkali, so as to promote the reuse of used copying papers, and also satisfies various properties as a toner including carrier spent, fogging, stability in electrification, durability, stability in conservation, crushability, cost, etc.; an electrostatic latent image developing toner comprising the above binder resin; and an image forming method and an image forming apparatus using the toner.

According to an aspect of the-present invention, there is provided a polyhydroxyalkanoate copolymer comprising at least, per polymer molecule, one kind of unit selected from the group consisting of chemical formulae (1) and (2):

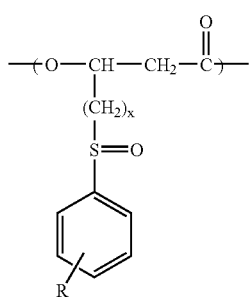
(1)

X = 1–7

(wherein R is any one selected from the group consisting of H, halogen, CN, $NO_2$, COOR', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for each unit)

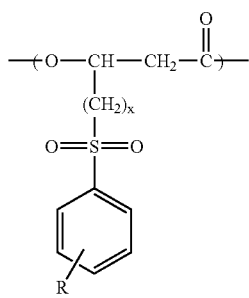
(2)

X = 1–7

(wherein R is any one selected from the group consisting of H, halogen, CN, $NO_2$, COO R', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for unit) and at least one unit selected from the group consisting of chemical formulae (3) to (6):

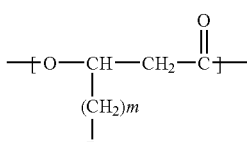
(3)

m = 1–8

(wherein m is an integer selected from the range shown in the same chemical formula; Rz comprises a residue having either a phenyl structure or a thienyl structure; and when more than one unit exist, m and Rz of each unit can independently represent any one of the integers and the substituents described above, respectively)

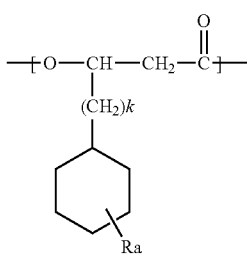
(4)

k = 0–8

(wherein $R_a$ is any one selected from the group consisting of H, CN, $NO_2$, halogen, $CH_3$, $C_2H_5$, $C_3H_7$, $CF_3$, $C_2F_5$ and $C_3F_7$; k is an integer selected from the range shown in the same chemical formula; and when more than one unit exist, k and $R_a$ of each unit can independently represent any one of the integers and the substituents described above, respectively)

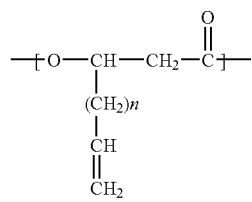
(5)

n = 1–8

(wherein n is an integer selected from the range shown in the same chemical formula, and when more than one unit exist, n of each unit can represent any one of the integers described above independently)

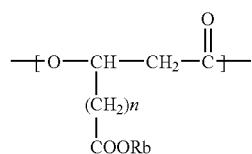
(6)

n = 1–8

(wherein n is an integer selected from the range shown in the same chemical formula; $R_b$ is any one selected from the group consisting of H, Na and K; and when more than one unit exist, n and $R_b$ of each unit can independently represent any one of the integers and the substituents described above, respectively).

According to another aspect of the present invention, there is provided a process of preparing a polyhydroxyalkanoate copolymer comprising, per polymer molecule, a 3-hydroxy-(substituted phenylsulfanyl)alkanoic acid unit having chemical formula (7):

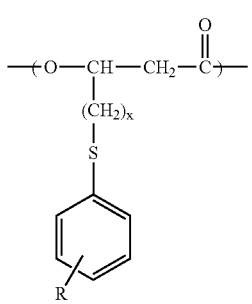

(7)

X = 1–7

(wherein R is any one selected from the group consisting of H, halogen, CN, $NO_2$, COOR', $SO_2R"$ (R' is any one selected from the group consisting of H, Na, K, $CH_3$ and $C_2H_5$; R" is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for unit) and at least one unit selected from the group consisting of units having chemical formulae (4), (5) and (20):

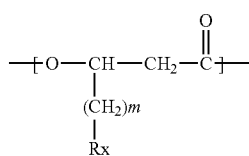

(20)

m = 1–8

(wherein m is an integer selected from the range shown in the same chemical formula; Rx comprises a residue having either a phenyl structure or a thienyl structure; and when more than one unit exists, m and Rx of each unit can independently represent any one of the integers and the substituents described above, respectively), which comprises the steps of allowing a microorganism capable of producing the polyhydroxyalkanoate copolymer to biosynthesize the polyhydroxyalkanoate copolymer under the condition that at least one ω-(substituted phenylsulfanyl)alkanoic acid having chemical formula (16):

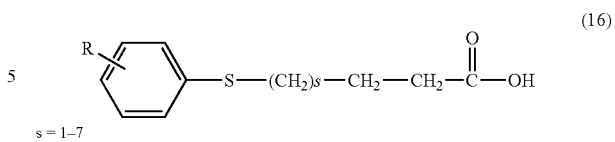

(16)

s = 1–7

(wherein R is any one selected from the group consisting of H, halogen, CN, $NO_2$, COOR', $SO_2R"$ (R' is any one selected from the group consisting of H, Na, K, $CH_3$ and $C_2H_5$; R" is any one selected from the group consisting of OH, ONa, OK, halogen, $OCH_3$ and $OC_2H_5$) , $CH_3$, $C_2H_5$, $C_3H_7$, $(CH_3)_2$—CH and $(CH_3)_3$—C, and when more than one unit exist, R of each unit can represent any one of the substituents described above independently; and s is an integer selected from 1 to 7 and can differ for each unit) and at least one compound selected from the group consisting of compounds having chemical formulae (17), (18) and (19):

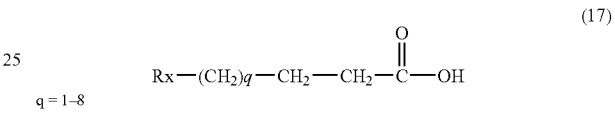

(17)

q = 1–8

(wherein q is an integer selected from the range shown in the same chemical formula; and Rx comprises a residue having either a phenyl structure or a thienyl structure)

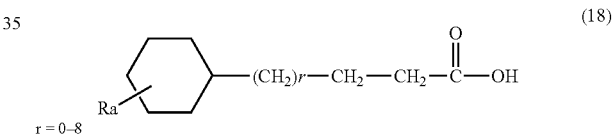

(18)

r = 0–8

(wherein $R_a$ is any one selected from the group consisting of H, CN, $NO_2$, halogen, $CH_3$, $C_2H_5$, $C_3H_7$, $CF_3$, $C_2F_5$ and $C_3F_7$; r is an integer selected from the range shown in the same chemical formula)

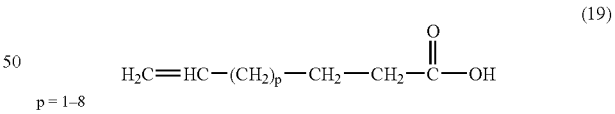

(19)

p = 1–8

(wherein p is an integer selected from the range shown in the same chemical formula) exist.

According to still another aspect of the present invention, there is provided a process of preparing a polyhydroxyalkanoate copolymer comprising, per polymer molecule, at least one unit selected from the group consisting of formulae (1) and (2) and at least one unit selected from the group consisting of chemical formulae (3) to (6), which comprises the steps of employing as a raw material a polyhydroxyalkanoate copolymer comprising, per polymer molecule, a 3-hydroxy-(substituted phenylsulfanyl)alkanoic acid unit having chemical formula (7) and at least one unit selected from the group consisting of chemical formulae (4), (5) and (20) and oxidizing at a time the 3-hydroxy-(substituted phenylsulfanyl)alkanoic acid unit having chemical formula (7) and the at least one unit selected from the group consisting of chemical formulae (4), (5) and (20).

According to a further aspect of the present invention, there is provided a resin composition comprising a resin (A) that is comprised of a polyhydroxyalkanoate comprising, per polymer molecule, at least one unit selected from the group consisting of 3-hydroxy-(substituted phenylsulfinyl)alkanoic acid units having chemical formula (1) and 3-hydroxy-(substituted phenylsulfonyl)alkanoic acid units having chemical formula (2) and a thermoplastic resin (B) that comprises no unit selected from the group consisting of 3-hydroxy-(substituted phenylsulfinyl)alkanoic acid units having chemical formula (1) and 3-hydroxy-(substituted phenylsulfonyl)alkanoic acid units having chemical formula (2), the content of the resin (A) being higher than that of the resin (B) in terms of mass percentage.

According to a further aspect of-the present invention, there is provided a resin composition comprising the resin (A) and an additive for resin.

According to a further aspect of the present invention, there is provided a resin for being decomposed by microorganisms comprising the resin (A).

According to a further aspect of the present invention, there is provided a method of decomposing the resin (A) comprising the steps of providing the resin and decomposing the resin in contact with microorganisms.

According to a further aspect of the present invention, there is provided a binder resin for forming a resin-based powder or granular material, which comprises a polyhydroxyalkanoate comprising, per polymer molecule, at least one unit selected from the group consisting of 3-hydroxy-(substituted phenylsulfinyl)alkanoic acid units having chemical formula (1) and 3-hydroxy-(substituted phenylsulfonyl)alkanoic acid units having chemical formula (2).

According to a further aspect of the present invention, there is provided a toner for developing electrostatic charge images, wherein the toner comprises the binder resin according to the binder resin of the present invention.

According to a further aspect of the present invention, there is provided a method for forming an image comprising the steps of charging an electrostatic latent image carrier by applying voltage to a charging member from outside; forming an electrostatic charge image on the charged electrostatic latent image carrier; developing the electrostatic charge image with a toner for developing electrostatic charge images to form a toner image on the electrostatic latent image carrier; transferring the toner image on the electrostatic latent image carrier to a recording medium; and fixing the toner image on the recording medium by heat, wherein the toner for developing electrostatic charge images of the present invention is used.

According to a further aspect of the present invention, there is provided an image forming apparatus comprising a charging means of charging an electrostatic latent image carrier by applying voltage to a charging member from outside; an electrostatic charge image forming means for the step of forming an electrostatic charge image on the charged electrostatic latent image carrier; a developing means of developing the electrostatic charge image with a toner for developing electrostatic charge images to form a toner image on the electrostatic latent image carrier; a transferring means of transferring the toner image on the electrostatic latent image carrier to a recording medium; and a fixing means of fixing the toner image on the recording medium by heat, wherein the toner for developing electrostatic charge images of the present invention is used.

According to the present invention, there are provided a polyhydroxyalkanoate copolymer comprising a monomer unit having a phenylsulfinyl or phenylsulfonyl structure on a side chain terminal thereof and further comprising a monomer unit having a substituent group other than a straight-chain alkyl group, such as a phenyl structure, thienyl structure or cyclohexyl structure, a vinyl group, or a carbonyl group on a side chain thereof; and a method for producing the same. The present invention enables the improvement of the thermal property of a polyhydroxyalkanoate copolymer and the control of the solubility in a solvent, thereby contributing greatly to the industry.

Moreover, according to the present invention, there are provided a resin composition, which comprises a polyhydroxyalkanoate having at least one type of unit selected from a group consisting of 3-hydroxy-(phenylsulfinyl)alkanoic acid units and 3-hydroxy-(phenylsulfonyl)alkanoic acid units and has biodegradability, heat resistance and mechanical property in a well balanced manner; a molded article; and a method for producing the same.

The resin composition of the present invention can be used for various types of heating apparatuses, containers, automotive parts, etc., and more specifically, it can be used for containers such as food containers, beverage containers, toiletry containers including containers for shampoo or conditioner, drug containers, cosmetic containers, etc.

Furthermore, according to the present invention, there are provided a binder resin comprising a PHA having at least one type of unit selected form a group consisting of 3-hydroxy-(phenylsulfinyl)alkanoic acid units and 3-hydroxy-(phenylsulfonyl)alkanoic acid units, which is biodegradable, highly contributes to the protection of the natural environment, facilitates the conventional deinking process of using alkali, so as to promote the reuse of used copying papers, and also satisfies various properties as toner including carrier spent, fogging, stability in electrification, durability, stability in conservation, crushability, cost, etc.; an electrostatic latent image developing toner comprising the binder resin; and an image forming method and an image forming apparatus using the toner.

BEST MODE FOR CARRYING OUT THE INVENTION

Figure 1:
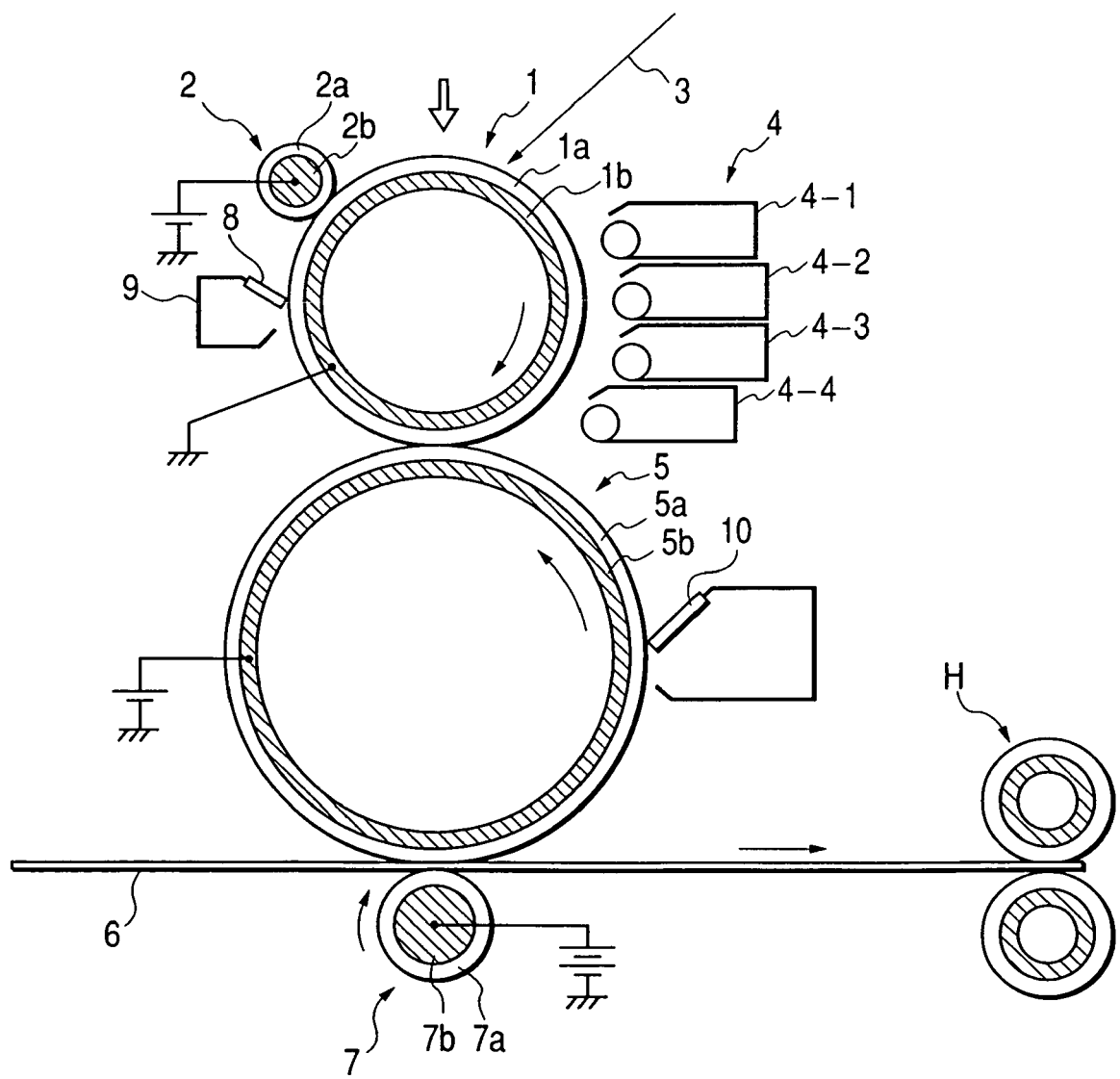
FIG. 1 is a schematic explanatory view of an image forming apparatus used in Examples D-19 to D-34 and Comparative Examples D-3 and D-4.

The polyhydroxyalkanoate copolymer of the present invention may further comprises, per polymer molecule, at least one unit selected from the group consisting of 3-hydroxy-(substituted phenylsulfanyl)alkanoic acid units having chemical formula (7):

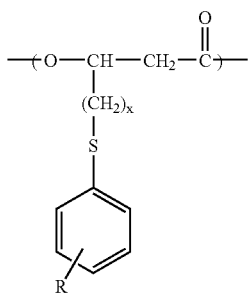

(7)

X = 1–7

(wherein R is any one selected from the group consisting of H, halogen, CN, $NO_2$, COO R', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for unit).

In the polyhydroxyalkanoate copolymer of the present invention, Rz in chemical formula (3) is preferably any one residue selected from the group consisting of chemical formulae (8), (9), (10), (11), (12), (13), (14) and (15):

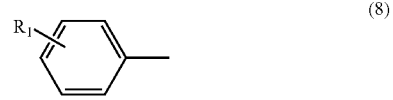

(8)

(wherein $R_1$ is any one selected from the group consisting of H, halogen, CN, $NO_2$, COOR' except the substituent introduced into the para-position of the phenyl group (R' is any one selected from the group consisting of H, Na and K) , $CH_3$, $C_2H_5$, $C_3H_7$, CH=$CH_2$, $CF_3$, $C_2F_5$ and $C_3F_7$, and when more than one unit exist, $R_1$ of each unit can represent any one of the substituents described above independently)

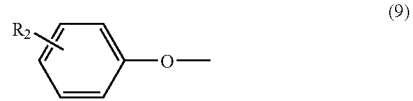

(9)

(wherein $R_2$ is any one selected from the group consisting of H, halogen, CN, $NO_2$, $CH_3$, $C_2H_5$, $C_3H_7$, $SCH_3$, $CF_3$, $C_2F_5$ and $C_3F_7$, and when more than one unit exist, $R_1$ of each unit can represent any one of the substituents described above independently)

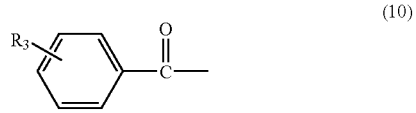

(10)

(wherein $R_3$ is any one selected from the group consisting of H, halogen, CN, $NO_2$, $CH_3$, $C_2H_5$, $C_3H_7$, $CF_3$, $C_2F_5$ and $C_3F_7$, and when more than one unit exist, $R_3$ of each unit can represent any one of the substituents described above independently)

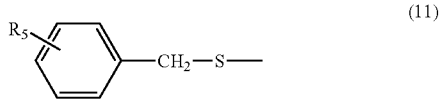

(11)

(wherein $R_5$ is any one selected from the group consisting of H, halogen, CN, $NO_2$, COOR', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, $R_5$ of each unit can represent any one of the substituents described above independently)

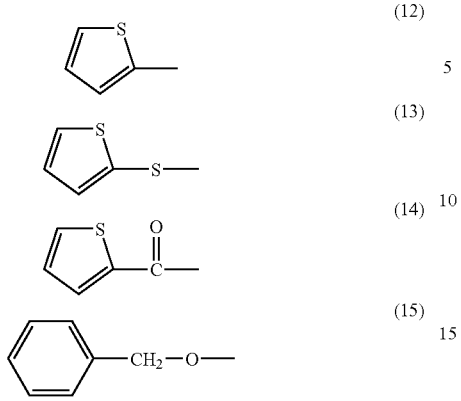

(12)

(13)

(14)

(15)

and when more than one unit exist, Rz of each unit can represent any one of the residues described above independently.

The polyhydroxyalkanoate copolymer of the present invention preferably has a number average molecular weight of 1,000 to 1,000,000.

The above-mentioned condition in the process of preparing a polyhydroxyalkanoate copolymer of the present invention is preferably comprised of cultivating the microorganism in a medium that comprises at least one ω-(substituted phenylsulfanyl)alkanoic acid having chemical formula (16) and at least one compound selected from the group consisting of compounds having chemical formulae (17) to (19). The medium may further comprise at least one selected from the group consisting of peptides, yeast extract, organic acids or the salts thereof, amino acids or salts thereof, saccharides, and strait-chain alkanoic acids with 4 to 12 carbon atoms or the salts thereof. Preferably, the petides are polypeptone; the organic acids or the salts thereof are pyruvic acid, oxalacetic acid, citric acid, isocitric acid, ketoglutaric acid, succinic acid, fumaric acid, malic acid, lactic acid and the salts thereof; the amino acids or the salts thereof are glutamic acid, aspartic acid and the salts thereof; and the saccharides are glyceraldehyde, erythrose, arabinose, xylose, glucose, galactose, mannose, fructose, glycerol, erythritol, xylitol, gluconic acid, glucuronic acid, galacturonic acid, maltose, sucrose and lactose. Further, the process of preparing a polyhydroxyalkanoate copolymer may comprise a step of recovering the polyhydroxyalkanoate copolymer produced by the microorganism from the cells of the microorganism. The microorganism is preferably one classified as *Pseudomonas* sp., and more preferably any one or more strains selected from the group consisting of *Pseudomonas cichorii* YN2 (FERM BP-7375), *Pseudomonas cichorii* H45 (FERM BP-7374) and *Pseudomonas jessenii* P161 (FERM BP-7376).

In the process of preparing a polyhydroxyalkanoate copolymer of the present invention, the polyhydroxyalkanoate copolymer as the raw material is preferably prepared by any one process selected from the group consisting of the above-mentioned processes of the present invention. The oxidation is preferably conducted using one or more oxidizing agents selected from the group consisting of permanganate, bichromate, periodate, hydrogen peroxide, sodium percarbonate, metachloroperbenzoate, performic acid and peracetic acid. The oxidizing agent is preferably permanganate and the oxidizing treatment is performed under acidic conditions. Further, the oxidization is preferably conducted using ozone.

In the process of preparing a polyhydroxyalkanoate copolymer of the present invention, Rz in chemical formula (3) is preferably at least any one kind of residue selected from the group consisting of chemical formulae (8), (9), (10), (11), (12), (13), (14) and (15), and Rx in chemical formula (20) is preferably-at least any one kind of residue selected from the group consisting of chemical formulae (9), (10), (11), (12), (13), (14), (15) and (21):

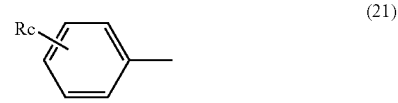

(21)

(wherein Rc is any one selected from the group consisting of H, halogen, CN, $NO_2$, $CH_3$, $C_2H_5$, $C_3H_7$, $CH=CH_2$, $CF_3$, $C_2F_5$ and $C_3F_7$, and when more than one unit exist, Rc of each unit can represent any one of the substituents described above independently).

In the resin composition of the present invention, the thermoplastic resin (B) is preferably comprised of one or more resins selected from the group consisting of polyester-based resin, polystyrene-based resin, polypropylene-based resin, polyethylene terephthalate-based resin, polyurethane-based resin, polyvinyl-based resin and polyamide-based resin. The polystyrene-based resin is more preferably polystyrene. The polyester-based resin is more preferably poly-ε-caprolactone or polylactic acid.

The resin composition of the present invention may further comprise an additive for resin.

The binder resin of the present invention may further comprise a thermoplastic resin other than the polyhydroxyalkanoate, wherein the content of the polyhydroxyalkanoate is higher than that of the thermoplastic resin in content by weight. The thermoplastic resin is preferably one or more selected from the group consisting of polycaprolactone and polylactic acid.

In the binder resin of the present invention, the number average molecular weight of the binder resin is preferably 2,000 or more and 300,000 or less.

The glass transition point of the binder resin of the present invention is preferably 30 to 80° C. and the softening point of the same is 60 to 170° C.

The resin-based powder or granular material in the binder resin of the present invention is preferably a toner for developing electrostatic charge images.

The transferring step in the image forming method of the present invention preferably comprises a first transferring step of transferring the toner image on the electrostatic latent image carrier to an intermediate transfer medium and a second transferring step of transferring the toner image on the intermediate transfer medium to the recording medium.

The transferring means in the image forming apparatus of the present invention preferably comprises a first transferring means of transferring the toner image on the electrostatic latent image carrier to an intermediate transfer medium and a second transferring means of transferring the toner image on the intermediate transfer medium to the recording medium.

PHA

Polyhydroxyalkanoate used in the present invention has a basic skeleton as a biodegradable resin, and is therefore capable of being used for producing various kinds of products through melt-processing and the like, as in the case of conventional plastics, and it also has a remarkable characteristic such that it is decomposed by organisms and involved in the material cycle in the natural world, unlike synthetic polymers derived from oil. Therefore, the compound requires no combustion process, and it is an effective material in the sense that it contributes to prevention of air pollution and global warming. The compound can be used as a plastic enabling preservation of environments.

Generally, Tm and Tg are important physical properties associated with the heat resistance or mechanical strength (e.g., elastic modulus) of resin materials. For example, a resin material with a high Tm or Tg value is excellent in heat resistance or strength. In contrast, a resin material with a low Tm or Tg value is poor in heat resistance or strength, although it has an advantage such as good moldability. A majority of the conventional PHA has a relatively low Tm or Tg value. Therefore, their extrusion molding property, mechanical property and heat resistance have a certain limit, and the scale-up of the uses also has a certain limit.

In a case where the polyhydroxyalkanoate used in the present invention is mixed with other resins to obtain a resin composition, when compared with the conventional resin composition using only the conventional mcl-PHA or unusual-PHA, the obtained resin composition has improved thermal property and improved mechanical property. Accordingly, the thus obtained resin composition can be applied to uses requiring the above physical properties. For example, it can be used under the environment where the temperature is relatively high (140° C. or lower)

Moreover, as described later, the polyhydroxyalkanoate of the present invention can also be used as a raw material for a toner binder for an electrophotographic toner. It has an extremely excellent character as a binder resin and can reduce burden on the environment caused by an electrophotographic process. Furthermore, the polyhydroxyalkanoate of the present invention is highly safe to the human body or environment. Still further, when an electrostatic latent image developing toner comprising the above binder resin is used in an image forming apparatus having a certain development system, significant effects can be obtained.

The PHA having these desired physical properties can be obtained by selecting conditions for culturing microorganisms capable of synthesizing the PHA of the present invention, and other conditions. For example, the number average molecular weight of the PHA can be controlled by controlling culture time or the like. Moreover, the number average molecular weight can also be controlled by eliminating low molecular weight components by means such as solvent extraction or reprecipitation. Herein, a glass transition temperature and a softening point correlate with the molecular weight of the PHA. It is also possible to control the glass transition temperature and the softening point by controlling the type and/or composition ratio of monomer units comprised in the PHA.

The molecular weight of the PHA is desirably between 1,000 and 10,000,000 at a number average molecular weight.

When such a compound is produced using microorganisms, the polyester resin is an isotactic polymer consisting only of an R form. However, if the object of the present invention is achieved from both physical and functional-aspects, it is not necessarily an isotactic polymer, but an atactic polymer can also be used. Moreover, it is also possible to produce the PHA by a chemical synthesis method in which a lactone compound is subjected to ring-opening polymerization using an organic metal catalyst (e.g., an organic catalyst containing aluminum, zinc or tin).

A PHA of interest in the present invention comprises at least one type of unit selected from a group consisting of a 3-hydroxy-(substituted phenylsulfinyl)alkanoic acid unit expressed by chemical formula (1) and a 3-hydroxy-(substituted phenylsulfonyl)alkanoic acid unit expressed by chemical formula (2). The PHA is synthesized, for example, using the microorganisms with an ability to produce the PHA, which will be described later. After biosynthesizing a PHA comprising a 3-hydroxy-(substituted phenylsulfanyl)alkanoic acid unit expressed by chemical formula (7) that is a raw material for the PHA of the present invention, an oxidization reaction is carried out using an oxidizing agent, so as to synthesize the PHA of the present invention.

Moreover, the use of the above microorganisms under appropriate conditions enables to synthesize a copolymer comprising at least one type selected from a group consisting of a 3-hydroxy-(substituted phenylsulfinyl)alkanoic acid unit and a 3-hydroxy-(substituted phenylsulfonyl)alkanoic acid unit, and another 3-hydroxyalkanoic acid unit. Specific examples of such a monomer unit may include: a 3-hydroxy-(substituted phenylsulfanyl)alkanoic acid unit that is a raw material for the PHA of the present invention; a 3-hydroxyalkanoic acid unit constituting an mcl-PHA, such as a 3-hydroxyhexanoic acid unit, 3-hydroxyheptanoic acid unit, 3-hydroxyoctanoic acid unit, 3-hydroxynonanoic acid unit, 3-hydroxydecanoic acid unit, 3-hydroxydodecanoic acid unit or 3-hydroxytetra acid unit; and a 3-hydroxyalkanoic acid having an aromatic ring, such as a 3-hydroxyphenylvaleric acid unit or 3-hydroxyphenoxyvaleric acid unit. Moreover, the PHA may comprise a plurality of these monomer units. In this case, using the characters of each monomer unit or functional groups contained therein, it is possible to control the physical properties of the PHA, to impart multiple functions to the PHA, and to express a new function by interaction among functional groups.

The polyhydroxyalkanoate comprising the unit expressed by the above chemical formula (7) that is used as a starting material for the present invention is not particularly limited. It can be produced by a production method comprising a production process by microorganisms having an ability to produce the PHA that will be described later, a production method using a plant/crop system into which a gene having an ability to produce PHA is introduced, a production method by chemical polymerization, and other methods. Preferably, the production method comprising a production process by microorganisms is used.

A production method of the present invention in which a polyhydroxyalkanoate comprising the unit expressed by the above chemical formula (7) as a starting material is used will be explained below.

The above polyhydroxyalkanoate as a starting material is produced by a production method, which is characterized in that the above microorganisms are cultured in a medium containing at least one type of ω-(substituted phenylsulfanyl)alkanoic acid expressed by chemical formula (16).

<Microorganisms Producing PHA>

The microorganism for use in the method of producing polyhydroxyalkanoate containing units each expressed by chemical formula (7) as a starting material according to the present invention may be any microorganism as long as it is a microorganism capable of producing PHA, namely a microorganism capable of producing a PHA type polyester containing 3-hydroxy-(substituted phenylsulfanyl)alkanoic acid units each expressed by general chemical formula (7) by culturing the microorganism in a culture medium containing ω-(substituted phenylsulfanyl)alkanoic acid expressed by chemical formula (16). A suitable example of usable microorganisms capable of producing PHA may be a microorganism belonging to *Pseudomonas*.

More specifically, among microorganisms belonging to *Pseudomonas*, more preferable species as the microorganism for use in the production method of the present invention may include *Pseudomonas cichorii*, *Pseudomonas putida*, *Pseudomonas fluorecense*, *Pseudomonas oleovolans*, *Pseudomonas aeruginosa*, *Pseudomonas stutzeri* and *Pseudomonas jessenii*.

Further, a more suitable strain includes, for example, *Pseudomonas cichorii* YN2 (FERM BP-7375), *Pseudomonas cichorii* H45 (FERM BP-7374), *Pseudomonas jessenii* P161 (FERM BP-7376) and *Pseudomonas putida* P91 (FERM BP-7373). These four types of strains are deposited on Nov. 20, 2000 at the International Patent Organism Depositary (IPOD) of National Institute of Advanced Industrial Science and Technology (AIST), Tsukuba Central 6, 1-1, Higashi 1-chome, Tsukuba-shi, Ibaraki-ken 305-8566, Japan, and described in Japanese Patent Application Laid-Open No. 2001-288256 (Patent Document 16) and Japanese Patent Application Laid-Open No. 2002-80751.

Moreover, other than these microorganisms belonging to *Pseudomonas* species, many types of microorganisms belonging to *Burkholderia* sp., *Aeromonas* sp., *Comamonas* sp., etc., are known to produce an mcl-PHA or unusual PHA, and they can also be applied to the biosynthesis of the PHA of the present invention.

These microorganisms have an ability to produce a polyhydroxyalkanoate comprising a ω-substituted-3-hydroxy-alkanoic acid as a monomer unit, from a raw material, ω-substituted-straight-chain alkanoic acid substituted with a 6-membered ring atomic group such as a substituted or unsubstituted phenyl group, substituted or unsubstituted phenoxy group, or substituted or unsubstituted cyclohexyl group on a side chain thereof, or ω-substituted-straight-chain alkanoic acid substituted with a 5-membered ring atomic group such as a thienyl group.

<Culture>

The above microorganisms are cultured in a medium containing at least a carbon source used as a substrate for introduction of a 3-hydroxy-(substituted phenylsulfanyl)alkanoic acid unit, another carbon source used as a substrate for introduction of a desired monomer unit other than the 3-hydroxy-(substituted phenylsulfanyl)alkanoic acid unit, and another carbon source for growth of the microorganisms, so as to produce a PHA of interest. The produced PHA is generally an isotactic polymer consisting only of an R form.

In the production method of the present invention, any culture medium may be used for the culture medium for use in the process of culturing a microorganism as long as the culture medium is an inorganic salt culture medium containing a phosphate and a nitrogen source such as an ammonium salt or nitrate, and in the process of producing PHA in the microorganism, the productivity of PHA can be improved by adjusting the concentration of the nitrogen source.

In addition, nutrients such as an yeast extract, polypeptone and a meat extract can be added to the culture medium as a matrix for promoting the propagation of the microorganism. That is, peptides may be added as an energy source and a carbon source in the form of nutrients such as an yeast extract, polypeptone and a meat extract.

Alternatively, for the culture medium, saccharides, for example, aldoses such as glyceroaldehyde, erythrose, arabinose, xylose, glucose, galactose, mannose and fructose, alditols such as glycerol, erythritol and xylitol, aldonic acids such as gluconic acid, uronic acids such as glucuronic acid and galacturonic acid, and disaccharides such as maltose, sucrose and lactose may be used as an energy source and a carbon source consumed with propagation of the microorganism.

Instead of the above described saccharides, organic acids or salts thereof, more specifically organic acids involved in the TCA cycle and organic acids derived from a biochemical reaction with less steps by one or two steps than the TCA cycle, or water soluble salts thereof may be used. As the organic acid or salt thereof, hydroxycarboxylic acids and oxocarboxylic acids such as pyruvic acid, oxalacetic acid, citric acid, isocitric acid, ketoglutaric acid, succinic acid, fumaric acid, malic acid and lactic acid or water soluble salts thereof can be used. Alternatively, amino acids or salts thereof, for example amino acids such as asparaginic acid and glutamic acid or salts thereof can be used. When the organic acid or salt thereof is added, it is more preferable that one or more types are selected from a group consisting of pyruvic acid, oxalacetic acid, citric acid, isocitric acid, ketoglutaric acid, succinic acid, fumaric acid, malic acid, lactic acid and salts thereof, and are added to the culture medium and dissolved therein. Alternatively, when the amino acid or salt thereof is added, it is more preferable that one or more types are selected from a group consisting of asparaginic acid, glutamic acid and salts thereof, and are added to the culture medium and dissolved therein. At this time, as required, all or part thereof can be added in the form of a water soluble salt to be dissolved uniformly without affecting the pH of the culture medium.

It is desirable that the concentration of the above coexisting substrate added to the culture medium as a carbon source for growth of the microorganism and energy source for production of polyhydroxyalkanoate is usually selected so that it is in the range of from 0.05 to 5% (w/v), more preferably 0.2 to 2% (w/v) per culture medium. That is, for peptides, yeast extracts, organic acids or salts thereof, amino acids or salts thereof, and saccharides that are used as the above coexisting substrates, one or more types thereof may be added, and at this time, it is desirable that the total concentration of these added substrates is with in the above described range of total concentrations.

Any carbon source may be used as a substrate for production of a polyhydroxyalkanoate of interest, as long as it can be converted into the monomer unit by the used microorganisms. A preferred substrate is ω-(substituted phenylsulfanyl)alkanoic acid expressed by chemical formula (16). More specifically, examples of such a substrate may include substituted phenylsulfanylbutyric acid, substituted phenylsulfanylvaleric acid, substituted phenylsulfanylhexanoic acid and substituted phenylsulfanylheptanoic acid. Of these, in terms of thermal property, substituted phenylsulfanylbutyric acid, substituted phenylsulfanylvaleric acid and substituted phenylsulfanylhexanoic acid are preferable. The ratio of content of these substrates is preferably within the range between 0.01% and 1% (w/v) per medium, and more preferably between 0.02% and 0.2% (w/v) per medium.

Any inorganic salt culture medium can be used in the production method of the present invention, as long as it contains components in which microorganisms can grow, such as a phosphorus source (e.g., phosphate) or nitrogen source (e.g., ammonium salts or nitrate). Examples of such an inorganic salt medium may include an MSB medium, an E medium (J. Biol. Chem., 218, 97-106 (1956)), and an M9 medium.

As one example, the composition of the inorganic salt culture medium (M9 culture medium) used in Examples described later is shown below.

(Composition of M9 Culture Medium)
$Na_2HPO_4$: 6.3
$KH_2PO_4$: 3.0
$NH_4Cl$: 1.0
NaCl: 0.5
(by g/L, at pH=7.0).

Further, for ensuring satisfactory propagation of cells and associated improvement of productivity of PHA, an essential trace element such an essential trace metal element should be added in an appropriate amount to an inorganic salt culture medium such as the above described M9 culture medium, and it is very effective to add about 0.3% (v/v) trace component solution of which composition is shown below. The addition of such a trace component solution supplies a trace metal element for use in propagation of the microorganism.

(Composition of Trace Component Solution)
nitrilotriacetic acid: 1.5; $MgSO_4$: 3.0; $MnSO_4$: 0.5; NaCl: 1.0; $FeSO_4$: 0.1; $CaCl_2$: 0.1; $CoCl_4$: 0.1; $ZnSO_4$: 0.1; $CuSO_4$: 0.1; $AlK(SO_4)_2$: 0.1; $H_3BO_3$: 0.1; $Na_2MoO_4$: 0.1; $NiCl_4$: 0.1 (g/L).

Any temperature at which microorganism strains to be used can suitably be propagated may be selected as a culture temperature, and an appropriate temperature is usually in the range of from about 15 to 37° C., more preferably from about 20 to 30° C.

Any culture method such as liquid culture and solid culture may be used for the culture as long as it allows propagation of microorganism and production of PHA. In addition, any type of culture method such as batch culture, fed-batch culture, semi-continuous culture and continuous culture may be used. Forms of liquid batch culture include a method of supplying oxygen while vibrating the microorganism in a vibration flask, and a method of supplying oxygen adopting a stirring ventilation system with a jar fermenter.

For the method of making the microorganism produce and accumulate PHA, a two-step culture method in which the microorganism is cultured by two steps may be adopted other than the one-step culture method in which the microorganism is cultured in an inorganic salt culture medium containing a phosphate and a nitrogen source such as an ammonium salt or a nitrate with a matrix added therein in a predetermined concentration as described above. In this two-step culture method, the microorganism is once propagated sufficiently in the inorganic salt culture medium containing a phosphate and a nitrogen source such as an ammonium salt or a nitrate with a matrix added therein in a predetermined concentration as a primary culture, and thereafter cells obtained by the primary culture are relocated to a culture medium with a matrix added therein in a predetermined concentration after limiting the amount of nitrogen source such as ammonium chloride contained in the culture medium, and are further cultured as a secondary culture, thereby making the microorganism produce and accumulate PHA. Use of this two-step culture method may improve the productivity of desired PHA.

Generally, a produced PHA type polyester has reduced water solubility because of the presence of hydrophobic atom groups such as a phenylsulfanyl group derived from a 3-hydroxy-(substituted phenylsulfanyl)akanoic acid unit in the side chain, and is accumulated in cells of the microorganism capable of producing PHA, and therefore can easily be separated from the culture medium by collecting cells propagated by culture and involved in production and accumulation of desired PHA type polyester. After the collected cells are washed and dried, the desired PHA type polyester can be collected.

In addition, polyhydroxyalkanoate is usually accumulated in cells of such a microorganism capable of producing PHA. For the method of collecting desired PHA from these microorganism cells, a method that is usually used may be adopted. For example, extraction with organic solvents such as chloroform, dichloromethane and acetone is most convenient. Other than the above described solvents, dioxane, tetrahydrofuran and acetonitrile may be used. In addition, in a working environment in which use of any organic solvent is not preferred, a method in which in stead of solvent extraction, any one of a treatment by surfactants such as SDS, a treatment by enzymes such as lysozyme, a treatment by chemicals such as hypochlorites, ammonium and EDTA, an ultrasonic crashing method, a homogenizer method, a pressure crushing method, a bead impulse method, a grinding method, an immersion method and a freeze-thaw method is used to physically crush microorganism cells, followed by removing cell components other than PHA to collect PHA may be adopted.

When the PHA of the present invention is produced using microorganisms, the produced PHA can contain monomer units other than the above 3-hydroxy-(substituted phenylsulfanyl)alkanoic acid unit. Accordingly, a polymer may be designed in consideration of the functionality and physical properties required of the polymer. Generally, a polymer comprising the above 3-hydroxy-(substituted phenylsulfanyl)alkanoic acid unit is expected to fully achieve the object of the present invention. However, if it is desired that the functionality and physical properties are widely controlled, it is also possible that the polymer comprises more types of monomer units, and it is preferable.

This is to say, not only a substrate for production of a polyhydroxyalkanoate of interest, that is, at least one type of ω-(substituted phenylsulfanyl)alkanoic acid expressed by chemical formula (16) is used, but also at least one type of ω-substituted alkanoic acid compounds expressed by chemical formula (17), at least one type of ω-cyclohexylalkanoic acid compounds expressed by chemical formula (18), or at least one type of ω-alkenoic acid compound expressed by chemical formula (19) is allowed to coexist with the above substrate during culture, so that it is possible to produce a polyhydroxyalkanoate comprising the 3-hydroxy-ω-substituted alkanoic acid unit expressed by chemical formula (20), the 3-hydroxy-ω-cyclohexylalkanoic acid unit expressed by chemical formula (4) or the 3-hydroxy-ω-alkenoic acid unit expressed by chemical formula (5) other than the 3-hydroxy-(substituted phenylsulfanyl)alkanoic acid unit expressed by chemical formula (7). In this case, each of at least one type of the ω-(substituted phenylsulfanyl)alkanoic acid expressed by chemical formula (16), at least one type of the ω-substituted alkanoic acid compounds expressed by chemical formula (17), at least one type of the ω-cyclohexylalkanoic acid compounds expressed by chemical formula (18) and at least one type of the ω-alkenoic acid compounds expressed by chemical formula (19) is selected preferably within the range between 0.01% and 1% (w/v) per medium, and more preferably within the range between 0.02% and 0.2% per medium.

Moreover, it is also possible to synthesize a copolymer comprising other 3-hydroxyalkanoic acid units. A 3-hydroxyalkanoic acid unit constituting an mcl-PHA, such as a 3-hydroxyhexanoic acid unit, 3-hydroxyheptanoic acid unit, 3-hydroxyoctanoic acid unit, 3-hydroxynonanoic acid unit, 3-hydroxydecanoic acid unit, 3-hydroxydodecanoic acid unit or 3-hydroxytetra acid unit may be a specific example of such a monomer unit. Furthermore, it is also possible that the PHA comprises a plurality of these monomer units. In this case, using the characters of each monomer unit or functional groups contained therein, it is possible to control the physical properties of the PHA, to impart multiple functions to the PHA, and to express a new function by interaction among functional groups.

<Synthesis of PHA of the Present Invention by Oxidization Reaction>

A polyhydroxyalkanoate comprising at least one type of unit selected from a group consisting of the 3-hydroxy-(substituted phenylsulfinyl)alkanoic acid unit expressed by chemical formula (1) and the 3-hydroxy-(substituted phenylsulfonyl)alkanoic acid unit expressed by chemical formula (2) can be produced by selectively oxidizing a sulfanyl group (—S—) that is a sulfur portion of the unit expressed by chemical formula (7) having the sulfanyl group (—S) as a phenylsulfanyl group or substituted phenylsulfanyl group on a side chain terminal thereof. Thus, a polyhydroxyalkanoate comprising at least one type of the unit expressed by chemical formula (1) or (2) can be obtained.

With respect to such a oxidation treatment, some reagents e.g. peroxide compound can be utilized. Any types of peroxide compound may be used as far as it contributes to the object of the present invention, that is, oxidation of the sulfanyl group (—S—) present as a phenylsulfanyl group or substituted phenylsulfanyl group. On this occasion, it is preferred to use in particular a peroxide compound selected from the group consisting of hydrogen peroxide, sodium percarbonate, metachloroperbenzoic acid, performic acid, and peracetic acid when taking into consideration the efficiency of oxidation, influences on the main chain skeleton of PHA and copolymer containing it, simplicity of treatment and so forth.

First, of those, treatment with hydrogen peroxide, which is easy in its treating method, will be described. The simplest treating method with hydrogen peroxide is a method in which a microorganism is cultured under the above-mentioned culture conditions and the microbial cells having accumulated therein PHA containing the unit of the chemical formula (7), i.e., a precursor of the PHA of the present invention, are suspended in hydrogen peroxide solution as they are and optionally heated and agitated for a predetermined period of time to treat the cells, and then the target PHA is recovered as an insoluble component. When the concentration of hydrogen peroxide is relatively high or when the reaction temperature is relatively high, the insoluble component derived from the microbial cells, for example, cell membrane may be oxidized to be decomposed and solubilized while only the PHA of the present invention is recovered as insoluble component in a substantially pure form. On the other hand, under mild conditions, the decomposition and solubilization of the insoluble component are not performed sufficiently and the step of disrupting living cells derived from the microbial cells may partly remain.

Upon utilizing such mild conditions, it is possible to apply a method in which cultured microbial cells are disrupted in advance, the insoluble component derived from the microbial cells is removed, PHA containing the unit of the chemical formula (7), which is a precursor of PHA of the present invention, is recovered as a crude product, then treated with hydrogen peroxide solution. By adopting the method including the step of disrupting cultured microbial cells in advance and separating and recovering the intermediate raw material (precursor) PHA, PHA having sufficiently high purity can be recovered even when the treatment with hydrogen peroxide solution is performed under relatively mild conditions.

In the method of producing the PHA according to the present invention, it is preferred that the step of disrupting living cells as described above is performed by means using no chemicals for disrupting cell membranes, such as a supersonic wave disrupting method, a homogenizer method, a pressure disrupting method, a bead impact method, a triturating method, a grinding method (in which cells are ground in a mortar with addition of an auxiliary agent such as glass powder or alumina powder), and a freezing and thawing method. After the step of disrupting living cells, the separated insoluble component is resuspended and subjected to centrifugation or the like to separate a solid component and a soluble component from each other, and only the solid component, which contains the PHA component serving as an intermediate raw material is treated with hydrogen peroxide.

Further, another method for separating PHA includes a method in which after the culture step only PHA is extracted and isolated from PHA accumulating microbial cells by utilizing a means for extraction and isolation with a solvent in which the accumulated PHA is soluble, such as chloroform, dichloromethane or acetone, and after the extraction and isolation, only the obtained PHA is treated with hydrogen peroxide. In this method of utilizing solvent extraction, the precursor PHA extracted and recovered from microbial cells tends to become agglomerate in an aqueous medium in which treatment with hydrogen peroxide is performed. The agglomerated precursor PHA frequently involves concomitant difficulty and troubles in operation; for example, its contact with a peroxide compound such as hydrogen peroxide is prevented and in some cases the efficiency of the oxidation reaction may be significantly reduced. From this standpoint, the two methods as earlier described are convenient in operation because the precursor PHA originally exists in the form of fine particles in the microbial cell so that in such a state fine particulate precursor PHA can be subjected to the treatment with hydrogen peroxide as a suspension in water.

In the method of producing the PHA according to the present invention, the hydrogen peroxide utilized as an oxidizing agent may be used in any form as far as it can attain the object of the present invention, that is, oxidation of the sulfanyl group (—S—) present as a phenylsulfanyl group or substituted phenylsulfanyl group. From the standpoint of controlling production processes, it is desirable to use a hydrogen peroxide solution whose concentration is in a stable state, for example, hydrogen peroxide dissolved in an aqueous solvent. For example, a hydrogen peroxide solution according to JIS K-8230, which can be produced stably on an industrial scale in large amounts, may be recommended. For example, hydrogen peroxide solution prepared by Mitsubishi Gas Chemical Company, Inc. (containing 31% of hydrogen peroxide) is a preferred solution of hydrogen peroxide in the method of the present invention.

In the method for producing the PHA according to the present invention, the conditions of the oxidation treatment with the hydrogen peroxide may vary depending on the state of PHA to be treated (whether or not microbial cell components are present, whether or not it is agglomerated or in a state of fine particules, etc.), but it is preferred to select the conditions approximately within the range described below. Generally, when the residual amount of microbial cell components is small, or when the form of the precursor PHA is particulate, oxidation and solubilization of unnecessary microbial cell components are performed readily or the particulate PHA itself is treated more quickly, and thus milder conditions may be used. When utilizing the above-mentioned JIS K-8230 standard preparation hydrogen peroxide solution (containing 31% of hydrogen peroxide), the dilution condition (concentration), use amount, treating temperature, treating time and so forth may be selected within the ranges described below.

Concentration of hydrogen peroxide in the treating solution: depending on reaction temperature; from 8% (about 4 fold dilution) to 31% (stock solution), a more preferred concentration range being from 16% (about 2-fold dilution) to 31% (stock solution);

Reaction amount: depending on the ratio of the units of the chemical formula (7) contained in the precursor PHA; from 30 mL to 500 mL in terms of the stock solution of hydrogen peroxide solution (containing 31% of hydrogen peroxide) per 1 g of PHA before the treatment, a more preferred reaction amount being within the range of from 100 mL to 300 mL;

Reaction temperature: depending on the concentration of hydrogen peroxide in the treating solution; from 30° C. to 100° C., a more preferred temperature being selected to fall within the range of from 80° C. to 100° C.; and Reaction time: depending on the reaction temperature; from 10 minutes to 180 minutes, a more preferred reaction time being within the range of from 30 minutes to 120 minutes.

Treatment with hydrogen peroxide performed under the conditions within the ranges described above converts the precursor PHA containing the unit of the chemical formula (7) which is accumulated in the microbial cell into a PHA containing in the polymer molecule thereof at least one of the units of the chemical formulae (1) and (2), or a PHA that contains in addition to the units of the chemical formulae (1) and/or (2) the unit of the chemical formula (7) derived from the intermediate raw material PHA. On this occasion, by selecting the reaction conditions of the treatment with hydrogen peroxide to control a rate at which oxidation proceeds and a reaction amount, the existence ratio of the units of three types described above can be regulated.

Next, the method in which metachloroperbenzoic acid (MCPBA) is used as the peroxide compound will be described.

When MCPBA is used, the oxidation of sulfanyl group (—S—) that exists as a phenylsulfanyl group or substituted phenylsulfanyl group proceeds stoichiometrically, so that it is easy to control the content ratios of the units of the chemical formulae (1) and (2). Also, since the reaction conditions are mild, unnecessary side reactions such as cleavage of PHA main chain backbone, crosslinking reaction at the active site and the like are prevented from easily occurring. Therefore, in the method for the production of PHA according to the present invention, metachloroperbenzoic acid (MCPBA) is one of very suitable peroxide compounds for selectively producing the target PHA.

As for the general reaction conditions for selectively oxidizing a sulfanyl group (—S—) into a sulfinyl group (—SO—), the reaction is performed in chloroform with the amount of MCPBA being selected to be slightly in excess of 1 mole per mole of the unit containing a sulfanyl group (—S—) in the intermediate raw material PHA (precursor), specifically from the range of from 1.1 to 1.4 moles, at a temperature selected from the range of from 0° C. to 30° C. Under the oxidation conditions as described above, the reaction can proceed up to approximately 90% of the stoichiometric value when the reaction time is so set as to be about 10 hours and up to approximately 100% of stoichiometric value when the reaction time is so set as to be about 20 hours.

To oxidize all the sulfanyl groups (—S—) to sulfonyl groups (—$SO_2$—), the reaction may be performed with the amount of MCPBA being selected to be slightly in excess of 2 moles per mole of the unit containing a sulfanyl group (—S—) in the intermediate raw material PHA (precursor), specifically, in the range of from 2.1 to 2.4 moles, under the same solvent, temperature and time conditions as those described above.

Moreover, a method of using permanganate will be explained as an example of using other compounds as a peroxide compound. Potassium permanganate is common as the above described permanganate used as an oxidizing agent. The use amount of permanganate may be usually at least 1 mol equivalent, and preferably 2 to 10 mol equivalent with respect to 1 mol of the unit comprising a phenylsulfanyl group expressed by chemical formula (7).

Various types of inorganic acids or organic acids such as sulfuric acid, hydrochloric acid, acetic acid or nitric acid are generally used to set a reaction system under an acidic condition. However, when acid such as sulfuric acid, nitric acid or hydrochloric acid is used, there is a risk that the ester bond of the main chain of a polyhydroxyalkanoate might be cleaved, resulting in decrease of the molecular weight. Accordingly, acetic acid is preferably used. The use amount of acid is generally within the range of 0.2 to 2,000 mol equivalent, and preferably 0.4 to 1,000 mol equivalent with respect to 1 mol of the unit comprising a phenylsulfanyl group expressed by chemical formula (7). If the used amount is less than 0.2 mol equivalent, it results in low yield. If it exceeds 2,000 mol equivalent, decomposed matter is generated by acid as a by-product. Thus, both cases are not preferable. Moreover, crown-ether can be used to promote the reaction. In such a case, crown-ether and permanganate form a complex, thereby obtaining an effect to increase reaction activity. Examples of a commonly used crown-ether include dibenzo-18-crown-6-ether, dicyclo-18-crown-6-ether, and 18-crown-6-ether. The use amount of crown-ether is usually 0.005 to 2.0 mol equivalent, and preferably 0.01 to 1.5 mol equivalent with respect to 1 mol of permanganate.

A solvent used in the oxidization reaction of the present invention is not particularly limited, as long as it is inactive to the reaction. Examples of a solvent to be used may include water; acetone; ethers such as tetrahydrofuran or dioxane; aromatic hydrocarbons such as benzene, toluene or xylene; aliphatic hydrocarbons such as hexane or heptane; and halogenated hydrocarbons such as methyl chloride, dichloromethane or chloroform. Of these, halogenated hydrocarbons such as methyl chloride, dichloromethane or chloroform and acetone are preferable in terms of the solubility of the polyhydroxyalkanoate.

In the above oxidization reaction of the present invention, the polyhydroxyalkanoate comprising the unit expressed by chemical formula (7), permanganate and acid may be fed to a reaction system together with a solvent from the beginning of the reaction, or each of these compounds may be added to the reaction system continuously or intermittently during the reaction. Otherwise, it may be possible that only permanganate has previously been dissolved or suspended in a solvent and that the polyhydroxyalkanoate and acid are then added to the reaction system continuously or intermittently during the reaction, or it may be also possible that only the polyhydroxyalkanoate has previously been dissolved or suspended in a solvent and that permanganate and acid are then added to the reaction system continuously or intermittently during the reaction. Moreover, it may also be possible that the polyhydroxyalkanoate and acid have previously been fed to the reaction system and that permanganate is then added thereto continuously or intermittently during the reaction. Furthermore, it may also be possible that permanganate and acid have previously been fed to the system and that the polyhydroxyalkanoate is then added thereto continuously or intermittently during the reaction. Still further, it may also be possible that the polyhydroxyalkanoate and permanganate have previously been fed to the system and that acid is then added thereto continuously or intermittently during the reaction.

The reaction temperature is usually between −20° C. and 40° C., and preferably 0° C. and 30° C. The reaction time depends on the stoichiometric ratio of the unit expressed by chemical formula (7) and permanganate and the reaction temperature, but it is usually 2 to 48 hours.

A precursor polyhydroxyalkanoate comprising the unit expressed by chemical formula (7) can be converted into a polyhydroxyalkanoate comprising in a molecule thereof at least one type selected from a group consisting of units expressed by chemical formulas (1) and (2) by treating the phenylsulfanyl group expressed by chemical formula (7) with an oxidizing agent. The polyhydroxyalkanoate produced by the method of the present invention having a polyhydroxyalkanoate produced by microorganisms as an intermediate material comprises, in a molecule thereof, a unit having at least one of a sulfinyl structure (—SO—) and a sulfonyl structure (—SO$_2$—). These structures strongly promote the localization of electrons in a molecule at the unit terminal. There is a possibility that the electric property of the polyhydroxyalkanoate of the present invention significantly differs from that of the conventional polyhydroxyalkanoate. Moreover, because of the localization of electrons, its manner to a solvent also differs from that of the conventional polyhydroxyalkanoate. For example, the polyhydroxyalkanoate of the present invention is soluble in a polar solvent such as dimethylformamide (DMF). Moreover, the inventive polyhydroxyalkanoate has remarkably controlled thermal properties such as an increased glass transition temperature as a typical example, and therefore it can be applied to a wide range of uses.

Furthermore, a polyhydroxyalkanoate copolymer comprising a unit having a carboxyphenyl group that is a structure expressed by chemical formula (3) and a unit expressed by chemical formula (6) can be obtained by oxidizing with an oxidizing agent a carbon-carbon double bond portion or a methyl group portion in a vinylphenyl group or methylphenyl group that is a structure expressed by chemical formula (2)) or a terminal vinyl group expressed by chemical formula (5). Examples of known methods of obtaining carboxylic acid by oxidizing a carbon-carbon double bond or methyl group with an oxidizing agent may include a method of using permanganate (J. Chem. Soc., Perkin. Trans. 1, 806 (1973)), a method of using dichromate, a method of using periodate, a method of using nitric acid (Japanese Patent Application Laid-Open No. 59-190945), and a method of using ozone (J. Am. Chem. Soc., 81, 4273 (1959)). Moreover, with regard to polyhydroxyalkanoate, the above Macromolecular chemistry, 4, 289-293 (2001) discloses a method of obtaining carboxylic acid by oxidizing a carbon-carbon double bond located at the side chain terminal of the polyhydroxyalkanoate with potassium permanganate as an oxidizing agent under an acidic condition. The same above method can be applied in the present invention.

Potassium permanganate is common as the above permanganate used as an oxidizing agent. Since the oxidization reaction is a stoichiometric reaction, the use amount of permanganate may be usually at least 1 mol equivalent, and preferably 2 to 10 mol equivalent with respect to 1 mol of the unit comprising a vinylphenyl or methylphenyl group that is a structure expressed by chemical formula (20), or to 1 mol of the unit expressed by chemical formula (5).

Various types of inorganic acids or organic acids such as sulfuric acid, hydrochloric acid, acetic acid or nitric acid are generally used to set a reaction system under an acidic condition. However, when acid such as sulfuric acid, nitric acid or hydrochloric acid is used, there is a risk that the ester bond of the main chain of a polyhydroxyalkanoate might be cleaved, resulting in decrease of the molecular weight. Accordingly, acetic acid is preferably used. The use amount of acid is generally within the range of 0.2 to 2,000 mol equivalent, and preferably 0.4 to 1,000 mol equivalent with respect to 1 mol of the unit comprising a vinylphenyl or methylphenyl group that is a structure expressed by chemical formula (20) or 1 mol of the unit expressed by chemical formula (5). If the used amount is less than 0.2 mol equivalent, it results in low yield. If it exceeds 2,000 mol equivalent, decomposed matter is generated by acid as a by-product. Thus, both cases are not preferable. Moreover, crown-ether can be used to promote the reaction. In such a case, crown-ether and permanganate form a complex, thereby obtaining an effect to increase reaction activity. Examples of a commonly used crown-ether include dibenzo-18-crown-6-ether, dicyclo-18-crown-6-ether, and 18-crown-6-ether. The use amount of crown-ether is usually 0.005 to 2.0 mol equivalent, and preferably 0.01 to 1.5 mol equivalent with respect to 1 mol of permanganate.

A solvent used in the oxidization reaction of the present invention is not particularly limited, as long as it is inactive to the reaction. Examples of a solvent to be used may include water; acetone; ethers such as tetrahydrofuran or dioxane; aromatic hydrocarbons such as benzene, toluene or xylene; aliphatic hydrocarbons such as hexane or heptane; and halogenated hydrocarbons such as methyl chloride, dichloromethane or chloroform. Of these, halogenated hydrocarbons such as methyl chloride, dichloromethane or chloroform and acetone are preferable in terms of the solubility of the polyhydroxyalkanoate.

In the above oxidization reaction of the present invention, a polyhydroxyalkanoate copolymer comprising the unit expressed by chemical formula (7) and the unit expressed by chemical formula (20) or (5), permanganate and acid may be fed to a reaction system together with a solvent from the beginning of the reaction, or each of these compounds may be added to the reaction system continuously or intermittently during the reaction. Otherwise, it may be also possible that only permanganate has previously been dissolved or suspended in a solvent and that the polyhydroxyalkanoate copolymer and acid are then added to the reaction system continuously or intermittently during the reaction, or it may be also possible that only the polyhydroxyalkanoate copolymer has previously been dissolved or suspended in a solvent and that permanganate and acid are then added to the reaction system continuously or intermittently during the reaction. Moreover, it may also be possible that the polyhydroxyalkanoate copolymer and acid have previously been fed to the reaction system and that permanganate is then added thereto continuously or intermittently during the reaction. Furthermore, it may also be possible that permanganate and acid have previously been fed to the system and that the polyhydroxyalkanoate copolymer is then added thereto continuously or intermittently during the reaction. Still further, it may also be possible that the polyhydroxyalkanoate copolymer and permanganate have previously been fed to the system and that acid is then added thereto continuously or intermittently during the reaction.

The reaction temperature is usually between −20° C. and 40° C., and preferably 0° C. and 30° C. The reaction time depends on the stoichiometric ratio between the units expressed by chemical formula (7) and chemical formula (20) or (5) and permanganate, and the reaction temperature, but it is usually 2 to 48 hours.

A precursor polyhydroxyalkanoate copolymer comprising the unit expressed by chemical formula (7) can be converted into a polyhydroxyalkanoate comprising in a molecule thereof at least one type selected from a group consisting of units expressed by chemical formulas (1) and (2), or into a polyhydroxyalkanoate copolymer still comprising the unit expressed by chemical formula (7) derived from the polyhydroxyalkanoate as an intermediate material as well as the units expressed by chemical formulas (1) and (2). At the same time, the precursor polyhydroxyalkanoate copolymer can be simultaneously converted into a polyhydroxyalkanoate copolymer comprising, in a molecule thereof, a unit comprising a carboxyl group as well as the units expressed by chemical formulas (1) and (2) by treating with an oxidizing agent a carbon-carbon double bond portion or methyl group portion in a vinylphenyl group or methylphenyl group that is a structure expressed by chemical formula (20) or a terminal vinyl group expressed by chemical formula (5).

<Resin Composition and Molded Article>

The PHA obtained by the above method is subjected to molding or processing as necessary, so as to obtain a molded article with a desired form.

The above PHA can be singly used as a biodegradable resin composition, but it can also be blended with other resin components depending on purposes within the range where desired properties are maintained. Regarding the mixing ratio of the PHA and a thermoplastic resin, it is preferable that the content of the PHA is larger than that of the thermoplastic resin. Specific examples of resin components may include a polyester resin, a polystyrene resin, a polypropylene resin, a polyethylene terephthalate resin, a polyurethane resin, a polyvinyl resin, and a polyamide resin. Of these, when a polyester resin such as poly-$\epsilon$-caprolactone or polylactic acid is used, a resin composition with excellent biodegradability can be obtained. However, even when other resin compositions such as polystyrene are used, it is possible to improve biodegradability by applying the method of the present invention. This is because the PHA of the present invention contained in a molded article that is obtained by blending the above PHA with the above resin is quickly decomposed in the natural environment, the molded article is thereby quickly decomposed, and because the blended resin also easily undergoes photolysis or biodegradation.

Moreover, resin additives can be added to the resin composition as necessary. Examples of such additives may include a plasticizer, a heat stabilizer, a lubricant, an antiblocking agent, a nuclear agent, a photolysis promoting agent, a biodegradation promoting agent, an antioxidant, an ultraviolet stabilizer, an antistatic agent, a flame retardant, a dropping agent, an antimicrobial agent, a deodorant, a filler, a coloring agent, and a mixture thereof.

Specific examples of a plasticizer may include an aliphatic dibasic acid ester, a phthalate ester, a hydroxypolycarboxylic acid ester, a polyester plasticizer, a fatty acid ester, an epoxy plasticizer, and a mixture thereof. The additive amount of such a plasticizer is different depending on purposes, but it is appropriate to add 3 to 30 parts by mass of plasticizer with respect to 100 parts by mass of resin composition.

A specific example of a heat stabilizer may include aliphatic carboxylate. More specific examples may include salts of sodium, calcium, aluminum, barium, magnesium, manganese, iron, zinc, lead, silver or copper, such as lactic acid or hydroxybutyric acid. The additive amount of such a heat stabilizer is preferably 0.5 to 10 parts by mass with respect to 100 parts by mass of resin composition.

Specific examples of a lubricant may include a fatty acid ester, a hydrocarbon resin, paraffin, higher fatty acid, oxy fatty acid, fatty acid amide, alkylene bis fatty acid amide, aliphatic ketone, a fatty acid lower alcohol ester, a fatty acid polyhydric alcohol ester, a fatty acid polyglycol ester, aliphatic alcohol, polyhydric alcohol, polyglycol, polyglycerol, a metallic soap, a denatured silicon, and a mixture thereof. The additive amount of such a lubricant is preferably 0.05 to 5 parts by mass with respect to 100 parts by mass of resin composition.

Specific examples of a photolysis promoting agent may include benzoins, benzoin alkyl ethers, benzophenones and derivatives thereof such as benzophenone or 4,4-bis(dimethylamino)benzophenone, acetophenones and derivatives thereof such as acetophenone or $\alpha,\alpha$-diethoxyacetophenone, quinones, thioxantones, an agent for photoexcitation such as phthalocyanine, anatase titanium oxide, an ethylene-carbon monoxide copolymer, and a sensitizer consisting of aromatic ketone and metal salts. Moreover, two or more of these photolysis promoting agents can be used in combination.

Specific examples of a biodegradation promoting agent may include organic acids such as glycolic acid, lactic acid, citric acid, tartaric acid, malic acid, oxalic acid, malonic acid, succinic acid, succinic anhydride or glutaric acid, and coconut shell activated carbon. Moreover, two or more of these biodegradation promoting agents can be used in combination.

Mn of the thus obtained resin composition comprising the PHA as a main component is preferably between 1,000 and 1,000,000.

The resin composition of the present invention can be used for mechanical parts, electrical or electronic components, various types of heating apparatuses, wrapping containers, automotive parts, etc., to which the conventional mcl PHA or unusual PHA has not been applied because of their thermal properties. For example, food wrapping containers are produced by any method selected from a group consisting of foam extrusion molding, nondrawn extruded sheet molding, biaxially-stretched extruded sheet molding, injection hollow molding, and injection molding, followed by postforming processing as necessary.

For example, in the case of foam extrusion molding, a melted resin is impregnated with gas as a foaming agent to form a foaming sheet, and it is then molded into a tray for perishable foodstuff, or bowl-shaped or horned container for instant needle. The obtained foaming sheet is postformed into a desired shape, so as to obtain a food wrapping material of interest in the present invention. Moreover, other food wrapping materials of interest such as a lunch box, lids thereof or food packages are obtained by forming a sheet with or without performing a drawing process, and then performing a postforming on the obtained sheet. Food containers or cups obtained by injection hollow molding or injection molding are also included in the above food wrapping containers.

Application to Toner

The polyhydroxyalkanoate of the present invention is applied to an electrostatic latent image developing toner and an image formation process using the same. More specifically, the inventive polyhydroxyalkanoate can be used as a raw material for a binder resin constituting the majority of the substantial part of the toner other than pigments.

That is to say, the present invention relates to a binder resin comprising the above polyhydroxyalkanoate, and further, it relates to an electrostatic latent image developing toner comprising the binder resin. Furthermore, the present invention relates to an image forming method, which comprises an electrification step of applying a voltage to an electrification member from the outside to uniformly electrify an electrostatic latent image carrier, a development step of forming a toner image on the electrified electrostatic latent image carrier, a transferring step of transferring the toner image on the electrified electrostatic latent image carrier to an object transfer material with or without an intermediate transferring member, and a heat-fixation step of heat-fixing the toner image on the material. Still further, the present invention relates to an image forming apparatus having each means corresponding to the above each step of the above method, that is, electrification means, development means, transferring means, and heat-fixation means.

<Binder Resin>

For the binder resin of the present invention, the above polyhydroxyalkanoate may be directly used, but the binder resin may also comprise other thermoplastic resins typically including biodegradable resins such as polycaprolactone or polylactic acid. When the number average molecular weight of the PHA is less than 300,000, the PHA has good solubility in each of polycaprolactone and polylactic acid, and therefore a transparent and colorless melted polymer blend body is obtained. Thus, low number average molecular weight is preferable. In contrast, when the PHA has a relatively high number average molecular weight such as more than 500,000, it does not have good solubility, and so the obtained melted polymer blend body has an unfavorable color. However, even in this case, if the molecular weight is decreased to less than 300,000 by mixing under a high shearing force for example, the solubility is improved, and a transparent and colorless melted polymer blend body can be obtained.

The number average molecular weight of the binder resin of the present invention is preferably between 2,000 and 300,000. Further, in order to express functions as a binder resin, the glass transition point of the binder resin of the present invention is preferably between 30° C. and 80° C., and the softening point is preferably between 60° C. and 170° C.

The PHA has a basic skeleton as a biodegradable resin, and is therefore capable of being used for producing various kinds of products through melt-processing and the like, as in the case of conventional plastics, and it also has a remarkable characteristic such that it is decomposed by organisms and involved in the material cycle in the natural world, unlike synthetic polymers derived from oil. Therefore, the compound requires no combustion process, and it is an effective material in the sense that it contributes to prevention of air pollution and global warming. The compound can be used as a plastic enabling preservation of environments.

Moreover, the PHA is easily hydrolyzed in the presence of alkaline water. Accordingly, it has an advantage in that it efficiently eliminates a toner containing pigments such as carbon black from printed papers.

In a case where the PHA of the present invention is used as a binder resin, its glass transition temperature is preferably between 30° C. and 80° C., more preferably between 40° C. and 80° C., and particularly preferably between 50° C. and 70° C. If the glass transition temperature is lower than 30° C., the blocking property of the binder resin is likely to become poor, and if it is higher than 80° C., its fixability is likely to become poor. In addition, the softening point of the PHA of-the present invention is preferably between 60° C. and 170° C., and particularly preferably between 80° C. and 140° C. If the softening point is lower than 60° C., the anti-offset property is likely to deteriorate, and if it is higher than 170° C., the fixing temperature is likely to rise.

Moreover, when the PHA is used as a binder resin, its number average molecular weight Mn is preferably between 2,000 and 300,000, more preferably between 2,000 and 150,000, and particularly preferably between 5,000 and 100,000. If the Mn is less than 2,000, the glass transition temperature is significantly decreased, and it might result in deterioration of the anti-blocking property. If it exceeds 300,000, viscosity is increased during the melting process, and it might result in deterioration of the low-temperature fixability.

Commercially available products, e.g., Lacty (product name) manufactured by Shimadzu Corporation, can be preferably used as thermoplastic resins such as polylactic acid that can be added to the PHA of the present invention. In addition, those obtained by various types of polymerization methods can also be used. Moreover, any given resins that will be described later in "Binder resin" can also be mixed into the PHA.

<Other Constitutional Materials>

Other constitutional materials constituting the electrostatic latent image developing toner of the present invention will be explained below. The electrostatic latent image developing toner of the present invention comprises a coloring agent, an electrical charge controlling agent, and other additives that are added as necessary, as well as the above binder resin.

(Binder Resin: Components Other Than PHA)

The binder resin of the present invention can be preferably used as a binder resin. However, thermoplastic resins other than the binder resin of the present invention can also be contained in the binder resin. For example, the binder resin of the present invention can be mixed with polystyrene, polyacrylic acid ester, a styrene-acrylic acid ester copolymer, polyvinyl chloride, polyvinyl acetate, polyvinylidene chloride, a phenol resin, an epoxy resin, or a polyester resin. Such a thermoplastic resin is not particularly limited, and any thermoplastic resin can be used with the binder resin of the present invention, as long as it is commonly used for the production of a toner. When a thermoplastic resin having no biodegradability is used as a binder resin other than PHA, the mixing ratio of other thermoplastic resins is preferably less than 50% by mass with respect to the total binder resin. If the mixing ratio of other thermoplastic resins is more than 50% by mass, other binder resins have too strong binding strength to the surface of a paper, thereby decreasing the deinking ability. Moreover, when the resin is used as a biodegradable toner, it is preferable not to add other thermoplastic resins with no biodegradability thereto.

(Other Biodegradable Plastics)

In addition, in the present invention, various commercially available biodegradable plastics are preferably used. Examples of the biodegradable plastics are "Ecostar", "Ecostar plus" (produced by Hagiwara Industries, Inc.), "Biopole" (produced by Monsanto Company), "Ajicoat" (Ajinomoto Co., Ltd.), "Placcel", "Polycaprolactone" (produced by Daicel Chem., Ind., Ltd.), "SHOWLEX", "Bionolle" (produced by Showa Denko K.K.), "Lacty" (produced by Shimadzu Corporation), "Lacea" (produced by Mitsui Chemicals, Inc.) and the like. When these resins are used as a mixture, bioderadability that is the characteristic of the toner of the present invention will not be damaged.

Of these, polycaprolactone (i.e., an ϵ-caprolactone copolymer) or the above polylactic acid is particularly preferable in that these compounds are easily and completely decomposed by lipase, esterase, etc., and in that they are easily blended with other resins and their physical properties are easily modified by copolymerization or the like.

(Specific Examples of other Resins)

Examples of the styrene-based polymer include copolymers of styrene and (meth)acrylic acid ester, copolymers of these monomers and other monomer copolymerizable therewith, copolymers of styrene and a diene-based monomer (butadiene, isoprene or the like) and copolymers of these monomers and other monomers copolymerizable therewith, and the like. The polyester-based polymer includes polycondensation products between an aromatic dicarboxylic acid and an alkylene oxide adduct of an aromatic diol and the like. The epoxy-based polymer includes reaction products between an aromatic diol and epichlorohydrin and modified products thereof and the like. The polyolefin-based polymer includes polyethylene, polypropylene and copolymer chains of these and other monomers copolymerizable therewith, and the like. The polyurethane-based polymer includes polyaddition products between an aromatic diisocyanate and an alkylene oxide adduct of an aromatic diol and the like.

Specific examples of the binder resin used in combination with the electrical charge controlling agent of the present invention or in mixture with the binder resin of the present invention include polymers of polymerizable monomers described below, mixtures of these or copolymerization products obtained by using two or more polymerizable monomers described below. Specifically, such polymers include, for example, styrene-based polymers such as styrene/acrylic acid copolymers, or styrene/methacrylic acid-based copolymers, polyester-based polymers, epoxy-based polymers, polyolefin-based polymers, polyurethane-based polymers and the like, which are suitably used.

Specific examples of the polymerizable monomer includes styrene and derivatives of styrene, for example, styrene; styrene derivatives, such as o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; ethylenically unsaturated monoolefins, such as ethylene, propylene, butylene, and isobutylene; unsaturated polyenes, such as butadiene; vinyl halides, such as vinyl chloride, vinylidene chloride, vinyl bromide, and vinyl fluoride; vinyl esters, such as vinyl acetate, vinyl propionate, and vinyl benzoate; α-methylene-aliphatic monocarboxylic acid esters, such as methyl methacrylate, ethyl methacrylate, propyl methacrylate, methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylic acid esters, such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, and phenyl acrylate; vinyl ethers, such as vinyl methyl ether, vinyl ethyl ether, and vinyl isobutyl ether; vinyl ketones, such as vinyl methyl ketone, vinyl hexyl ketone, and methyl isopropenyl ketone; N-vinyl compounds, such as N-vinylpyrrole, N-vinylcarbazole, N-vinylindole, and N-vinylpyrrolidone; vinylnaphthalenes; acrylic acid or methacrylic acid derivatives, such as acrylonitrile, methacrylonitrile, and acrylamide; dicarboxylic acids, such as maleic acid, phthalic acid, succinic acid, terephthalic acid; esters of the above-mentioned α,β-unsaturated esters and diesters of dibasic acids such as methyl maleate, butyl maleate, and dimethyl maleate; polyol compounds, such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, and polyoxyethylenated bisphenol A; isocyanates, such as p-phenylene diisocyanate, p-xylylene diisocyanate, and 1,4-tetramethylene diisocyanate; amines, such as ethylamine, butylamine, ethylenediamine, 1,4-diaminobenzene, 1,4-diaminobutane, and monoethanolamine; epoxy compounds, such as diglycidyl ether, ethylene glycol diglycidyl ether, bisphenol A glycidyl ether, and hydroquinone diglycidyl ether; and so forth.

(Crosslinking Agent)

In the case of forming a binder resin, which is used in combination with the electrical charge controlling agent of the present invention or in mixture with the binder resin of the present invention, crosslinking agents described below may be used as necessary. Examples of the bifunctional crosslinking agent include divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates (MANDA, trade name; available from Nippon Kayaku Co., Ltd.), and the above diacrylates whose acrylate moiety has been replaced with dimethacrylate.

More than bifunctional, that is, polyfunctional cross-linking agents may include pentaerythritol triacrylate, trimethylolethane triacrylate, trimethylolpropane triacrylate, tetramethylolmethane tetraacrylate, oligoester acrylate, and the above compounds whose acrylate moiety has been replaced with methacrylate, and also 2,2-bis(4-methacryloxypolyethoxyphenyl)propane, diallyl phthalate, triallyl cyanurate, triallyl azo cyanurate, triallyl isocyanurate and diaryl chlorendate.

(Polymerization Initiator)

In the case of forming a binder resin, which is used in combination with the electrical charge controlling agent of the present invention or in mixture with the binder resin of the present invention, polymerization initiators described below may be used as necessary. The polymerization initiator includes, for example, t-butyl peroxy-2-ethylhexanoate, cumene perpivalate, t-butyl peroxylaurate, benzoyl peroxide, lauroyl peroxide, ocatanoyl peroxide, di-t-butyl peroxide, t-butylcumyl peroxide, dicumyl peroxide, 2,2'-azobisisobutyronitrile, 2,2'-azobis(2-methylbutyronitrile), 2,2'-azobis(2,4-dimethylvaleronitrile),2,2'-azobis(4-methoxy-2,4-dimethylvaleronitrile), 1,1-bis(t-butylperoxy)-3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl-4,4-bis(t-butylperoxy)valerate, 2,2-bis(t-butylperoxy)butane, 1,3-bis(t-butylperoxyisopropyl)benzene, 2,5-dimethyl-2,5-di(t-butylperoxy)hexane, 2,5-dimethyl-2,5-di(t-butylperoxy)hexane, 2,5-dimethyl-2,5-di(benzoylperoxy)hexane, di-t-butyl diperoxyisophthalate, 2,2-bis(4,4-di-t-butylperoxycyclohexyl)propane, di-t-butyl peroxy-α-methylsuccinate, di-t-butyl peroxydimethylglutarate, di-t-butyl peroxyhexahydroterephthalate, di-t-butyl peroxyazelate, 2,5-dimethyl-2,5-di(t-butylperoxy)hexane, diethylene glycol bis(t-butylperoxycarbonate), di-t-butyl peoxytrimethyladipate, tris(t-butylperoxy)triazine, vinyl tris (t-butylperoxy)silane and the like. These may be used singly or in combination. As for the amount thereof, they may be used in a concentration of 0.05 mass parts or more, preferably from 0.1 to 15 mass parts per 100 mass parts of the monomer.

<Electrical Charge Controlling Agent>

A commonly used electrical charge controlling agent can be used as an electrical charge controlling agent that is combined with the binder resin comprising the PHA of the present invention. Specific examples of such an electrical charge controlling agent may include nigrosine dyestuff, quaternary ammonium salts, and monoazo metallic complex salt dyestuff. The additive amount of an electrical charge controlling agent can be determined, considering various conditions such as the electrification characteristic of the binder resin, the production method including the additive amount of a coloring agent and a dispersion method, and the electrification characteristic of other additives. The electrical charge controlling agent can be added generally at a ratio of 0.1 to 20 parts by mass, and preferably at a ratio of 0.5 to 10 parts by mass with respect to 100 parts by mass of binder resin. Other than the above described substances, inorganic particles of metallic oxide, or inorganic substances whose surface is treated with the above organic substances, may also be used. These electrical charge controlling agents may be mixed into the binder resin, or may be attached on the surface of toner particles.

<Colorant>

As for the colorant that constitutes the electrostatic charge image developing toner of the present invention, any colorant that is generally used in producing toners may be used and is not particularly limited. For example, carbon black, titanium white, monoazo red pigments, disazo yellow pigments, quinacridone magenta pigments, anthraquinone pigments, any other pigments and/or dyes may be used.

More concretely speaking, when the electrostatic charge image developing toner of the present invention is used as a magnetic color toner, the colorant that can be used includes, for example, C.I. Direct Red 1, C.I. Direct Red. 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, C.I. Basic Green 6, etc.

As the pigment, there may be used chrome yellow, cadmium yellow, mineral fast yellow, navel yellow, naphthol yellow S, Hansa yellow G, permanent yellow NCG, tartrazine lake, chrome orange, molybdenum orange, permanent orange GTR, pyrazolone orange, benzidine orange G, cadmium red, permanent red 4R, watching red calcium salt, eosin lake, brilliant carmine 3B, manganese violet, fast violet B, methyl violet lake, Prussian blue (iron blue), cobalt blue, alkali blue lake, victoria blue lake, phthalocyanine blue, fast sky blue, indanthrene blue BC, chrome green, chromium oxide, pigment green B, malachite green lake, final yellow green G and the like.

Further, when the electrostatic charge image developing toner of the present invention is used as a toner for two-component full color toner, the following may be used as a colorant. Examples of the coloring pigment for magenta color toner include C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, and 209, C.I. Pigment Violet 19, C.I. Vat Red 1, 2, 10, 13, 15, 23, 29, and 35, etc.

In the present invention, the above-cited pigments may be used singly. However, it is more preferred that a dye and a pigment are used in combination to increase sharpness of the pigment in consideration of the image quality of full color images. Examples of the dye for magenta used in this case include oil-soluble dyes, such as C.I. Solvent Red 1, 3, 8, 23, 24, 25, 27, 30, 49, 81, 82, 83, 84, 100, 109, and 121, C.I. Disperse Red 9, C.I. Solvent Violet 8, 13, 14, 21, and 27, C.I. Disperse Violet 1, etc.; basic dyes, such as C.I. Basic Red 1, 2, 9, 12, 13, 14, 15, 17, 18, 22, 23, 24, 27, 29, 32, 34, 35, 36, 37, 38, 39, 40, C.I. Basic Violet 1, 3, 7, 10, 14, 15, 21, 25, 26, 27, and 28; etc.

Other coloring pigments include cyan coloring pigments, such as C.I. Pigment Blue 2, 3, 15, 16, and 17, C.I. Vat Blue 6, C.I. Acid Blue 45 and copper phthalocyanine pigments having a phthalocyanine skeleton substituted with 1 to 5 phthalimidomethyl groups, etc.

Examples of the coloring pigment for yellow include C.I. Pigment Yellow 1, 2, 3, 4, 5, 6, 7, 10, 11, 12, 13, 14, 15, 16, 17, 23, 65, 73, and 83, C.I. Vat Yellow 1, 3, and 20, etc.

The dyes and pigments as described above may be used singly or as optional mixtures in order to obtain a desired color tone of the toner. Taking into consideration environmental protection or safety for the human body, various kinds of edible coloring matter such as edible lake may be suitably used. Examples of such a food color may include food red 40 aluminum lake, food red 2 aluminum lake, food red 3 aluminum lake, food red 106 aluminum lake, food yellow 5 aluminum lake, food yellow 4 aluminum lake, food blue 1 aluminum lake, and food blue 2 aluminum lake.

The above water-insoluble food colors can be function as electrical charge controlling agents. In this case, the above aluminum lake can be preferably used for negative charge. Thus, when a water-insoluble food color has a function as an electrical charge controlling agent, it cannot only improve the safety of a toner to the environment, but also can contribute to the cost-reduction of the toner.

The content of the above-mentioned colorants in the toner may be varied widely depending on a desired coloring effect or other factors. Usually, to obtain the best toner characteristics, that is, taking into consideration coloring power of printing, shape stability of toner, flying of toner and so forth, the colorants are used in a proportion of usually from 0.1 to 60 mass parts, preferably from 0.5 to 20 mass parts per 100 mass parts of the binder resin.

<Other Components of Toner>

The electrostatic charge image developing toner of the present invention may contain, besides the above-mentioned binder resin and colorant components, the compounds described below within the range in which they do not give adverse influence on the effects of the present invention (in a proportion smaller than the contents of the binder resin component). Examples of such compounds include aliphatic or alicyclic hydrocarbon resins and aromatic petroleum resins, such as silicone resin, polyester, polyurethane, polyamide, epoxy resin, polyvinyl butyral, rosin, modified rosin, terpene resin, phenol resin, low molecular weight polyethylene, and low molecular weight polyproplene, and chlorinated paraffin, paraffin wax, and so-forth. Preferably usable waxes among these specifically include low molecular weight polypropylene and side products thereof, low molecular weight polyesters and ester-based waxes, aliphatic derivatives thereof. Also, waxes prepared by fractionation of these waxes according to molecular weight by various methods may be preferably used in the present invention. Further, after the fractionation, oxidation, block copolymerization or graft modification may be performed.

In particular, the electrostatic charge image developing toner of the present invention exhibits excellent characteristics in the case where laminagraphic observation performed with a transmission electron microscope (TEM) shows that the wax component is dispersed in the binder resin in the form of substantially spherical and/or spindle-shaped islets <Toner Production Process>

As a specific method for producing the electrostatic charge image developing toner of the present invention having the above constitution, any one of known methods may be used. The electrostatic charge image developing toner of the present invention can be produced by the so-called pulverization method in which a toner is obtained, for example, by the following processes.

That is, stated specifically, the electrostatic charge image developing toner of the present invention can be obtained as follows: resins such as a binder resin, and a electrical charge controlling agent and a wax that is added as needed are sufficiently mixed in a mixer such as a Henschel mixer, a ball mill or the like and melt-kneaded by using a thermal kneader such as a heat roll, a kneader or an extruder to make the resins compatible with each other. Then, a pigment, dye or magnetic material as a colorant, and an additive that is added as needed, such as a metal compound, are dispersed or dissolved in the kneaded resin and cooled and solidified. The solid is then pulverized by a pulverizer such as a jet mill or a ball mill and classified to produce the electrostatic charge image developing toner of the present invention having a desired particle size. In the classification step, it is preferred to use a multisegment classifier to increase the production efficiency.

The electrostatic charge image developing toner of the present invention can be obtained also by the following method. That is, a binder resin and the electrical charge controlling agent are mixed in the form of solutions by using a solvent or solvents (aromatic hydrocarbons such as toluene and xylene, halides such as chloroform and ethylene dichloride, ketones such as acetone and methyl ethyl ketone, amides such as dimethylformamide, and the like) and agitated. Thereafter, the mixed solution is poured into water to cause reprecipitation, and the solids are filtered, dried and pulverized by using a pulverizer such as a jet mill or a ball mill, followed by classification to obtain the electrostatic charge image developing toner of the present invention having a desired particle size. In the classification step, it is preferred to use a multisegment classifier to increase the production efficiency.

Further, the electrostatic charge image developing toner of the present invention can be obtained also by a so-called polymerization method as described below. In this case, the binder resin of the present invention, a polymerizable monomer of the other binder resin and a electrical charge controlling agent and a materials such as a pigment, dye or magnetic material as a colorant and optionally a crosslinking agent, a polymerization initiator, a wax, the other binder resin and other additives are mixed and dispersed and subjected to suspension polymerization in an aqueous dispersion medium in the presence of a surfactant and the like to synthesize polymerizable colored resin particles. Then, the obtained particles are subjected to solid-liquid separation, dried and classified as necessary to obtain the electrostatic charge image developing toner of the present invention.

Furthermore, colored fine particles containing no charge control agent can be prepared by the methods described above and then, the electrical charge controlling agent, singly or together with an external additive such as colloidal silica, may be added and fixed to the surface of the particles by a mechanochemical method or the like.

(Silica External Additive)

In the present invention, it is preferred that silica fine powder is added externally to the toner prepared by the above-mentioned method in order to increase charge stability, developability, flowability and durability. On this occasion, use of silica fine powder that has a specific surface area in the range of 20 $m^2$/g or more, in particular 30 to 400 $m^2$/g, as measured by nitrogen absorption according to the BET method can give good results. In this case, it is preferred to use the silica fine powder in an amount of from about 0.01 to about 8 mass parts, preferably from about 0.1 to about 5 mass parts, per 100 mass parts of the toner particle. As for the silica fine powder to be used, it is preferred to use one that is treated with a treating agent such as silicone varnish, various kinds of modified silicone varnish, silicone oil, various kinds of modified silicone oil, silane coupling agents, silane coupling agents having a functional groups, and other organosilicon compounds as needed for the purpose of imparting to the toner hydrophobic nature or controlling the chargeability of the toner. These treating agents may be used as mixtures.

(Inorganic Powder)

To increase the developability and durability of the toner, it is preferred to add inorganic powders, for example, powders of oxides of metals such as magnesium, zinc, aluminum, cerium, cobalt, iron, zirconium, chromium, manganese, strontium, tin, and antimony; composite metal oxides such as calcium titanate, magnesium titanate, and strontium titanate; metal salts such as calcium carbonate, magnesium carbonate and aluminum carbonate; clay minerals such as kaolin; phosphate compounds such as apatite; silicon compounds such as silicon carbide and silicon nitride; and carbon powders such as carbon black and graphite. Among those, fine powders of zinc oxide, aluminum oxide, cobalt oxide, manganese dioxide, strontium titanate, and magnesium titanate are preferably used.

(Lubricant)

Further, lubricant powder as described below may be added to the toner. Examples of the lubricant powder includes fluororesins such as Teflon, polyvinylidene fluoride; fluoro compounds such as carbon fluoride; fatty acid metal salts such as zinc stearate; fatty acid, fatty acid derivatives such as fatty acid esters; molybdenum sulfide and the like.

Although contents of these colorant, electrical charge controlling agent, binder resin used in mixture with the binder resin of the present invention and additives added as occasion demands in the toner are slight, it is more preferable to use any biodegradable material for them in view of waste disposal.

<Carrier>

The electrostatic charge image developing toner of the present invention having the above-described structure and properties may be applied to various kinds of known toners; for example, it may be used as a nonmagnetic toner that is used singly as a nonmagnetic one-component developer or as a magnetic two-component developer together with a magnetic carrier, or as a magnetic toner used singly as a magnetic one-component developer. Any conventionally known carrier may be used as a carrier in the two-component developing method. Specifically, surface-oxidized or -non-oxidized particles having an average particle size of from 20 to 300 μm formed from metals such as iron, nickel, cobalt, manganese, chromium, and rare earth elements, alloys thereof or oxides may be used as carrier particles. It is preferred that the carrier used in the present invention comprise the carrier particles described above, the surface of which are coated with a substance such as a styrene-based resin, acrylic-based resin, a silicone-based resin, a fluoro-based resin, a polyester resin or the like or has such a substance adhered thereto.

<Magnetic Toner>

The electrostatic charge image developing toner of the present invention may contain a magnetic material in the toner particles to form a magnetic toner. In this case, the magnetic material may also serve as a colorant. The magnetic material that can be used on this occasion includes iron oxides such as magnetite, hematite and ferrite; and metals such as iron, cobalt and nickel or alloys and mixtures of these metals with other metals such as aluminum, cobalt, copper, lead, magnesium, tin, zinc, antimony, beryllium, bismuth, cadmium, calcium, manganese, selenium, titanium, tungsten, and vanadium. Preferably, the magnetic materials that can be used in the present invention have an average particle size of 2 μm or less, more preferably from about 0.1 to about 0.5 μm. It is preferred that they are contained in the toner in an amount of from 20 to 200 mass parts per 100 mass parts of the binder resin, particularly preferably from 40 to 150 mass parts per 100 mass parts of the binder resin.

Further, to accomplish high image quality, it is necessary to make it possible to faithfully develop finer latent image dots. For this purpose, for example, it is preferable to control the electrostatic charge image developing toner particles of the present invention so as to have a weight average particle size in the range of from 4 to 9 μm. That is, the toner particles having a weight average particle size less than 4 μm are undesirable, since with such a toner the image transfer efficiency tends to decrease and much untransferred toner is liable to remain on the photosensitive member after the transfer, which tends to cause unevenness of image due to fogging/ transfer failure. If the weight average particle size of the toner particle exceeds 9 μm, scattering of characters or line images tends to occur.

In the present invention, the average particle size and particle size distribution of the toner are determined by using Coulter Counter TA-II (available from Coulter Electronics, Inc.) or Coulter Multisizer (available from Coulter Electronics Inc.), connected to an interface (Nikkaki Co., Ltd.) for outputting number distribution and volume distribution, and a personal computer PC 9801 (available from NEC K.K.). As the electrolyte to be used in the measurement is a 1% NaCl aqueous solution prepared with first class grade sodium chloride. The 1% NaCl aqueous solution is also commercially available; for example, ISOTON R-II (produced by Coulter Scientific Japan Co.). Specifically, for measurement, 0.1 to 5 mL of a surfactant (preferably an alkylbenzenesulfonic acid salt) as a dispersant and further 2 to 20 mg of a measurement sample are added to 100 to 150 mL of the electrolytic solution to form a sample for measurement. In the measurement, the resultant suspension of the measurement sample in the electrolytic solution is subjected to a dispersion treatment by an ultrasonic disperser for about 1 to 3 minutes and then subjected to measurement of particle size distribution by using the above-mentioned Coulter Counter TA-II equipped with a 100 μm-aperture as an aperture to obtain the volume and number of toner particles equal to or greater than 2 μm. From these a volume-basis particle size distribution and a number-basis particle size distribution were calculated. Then, the volume-basis weight average particle size (D4) and number-basis length-average particle size (D1) related to the present invention are derived from the volume-basis and number-basis distributions, respectively.

<Charge Amount>

It is preferred that the electrostatic charge image developing toner of the present invention has a charge quantity (two component method) per unit mass methacryloxypolyethoxyphenyl)propane, of −10 to −80 μC/g, more preferably −15 to −70 μC/g in order to increase transfer efficiency in a transfer method using a voltage applied transfer member.

Figure 7:
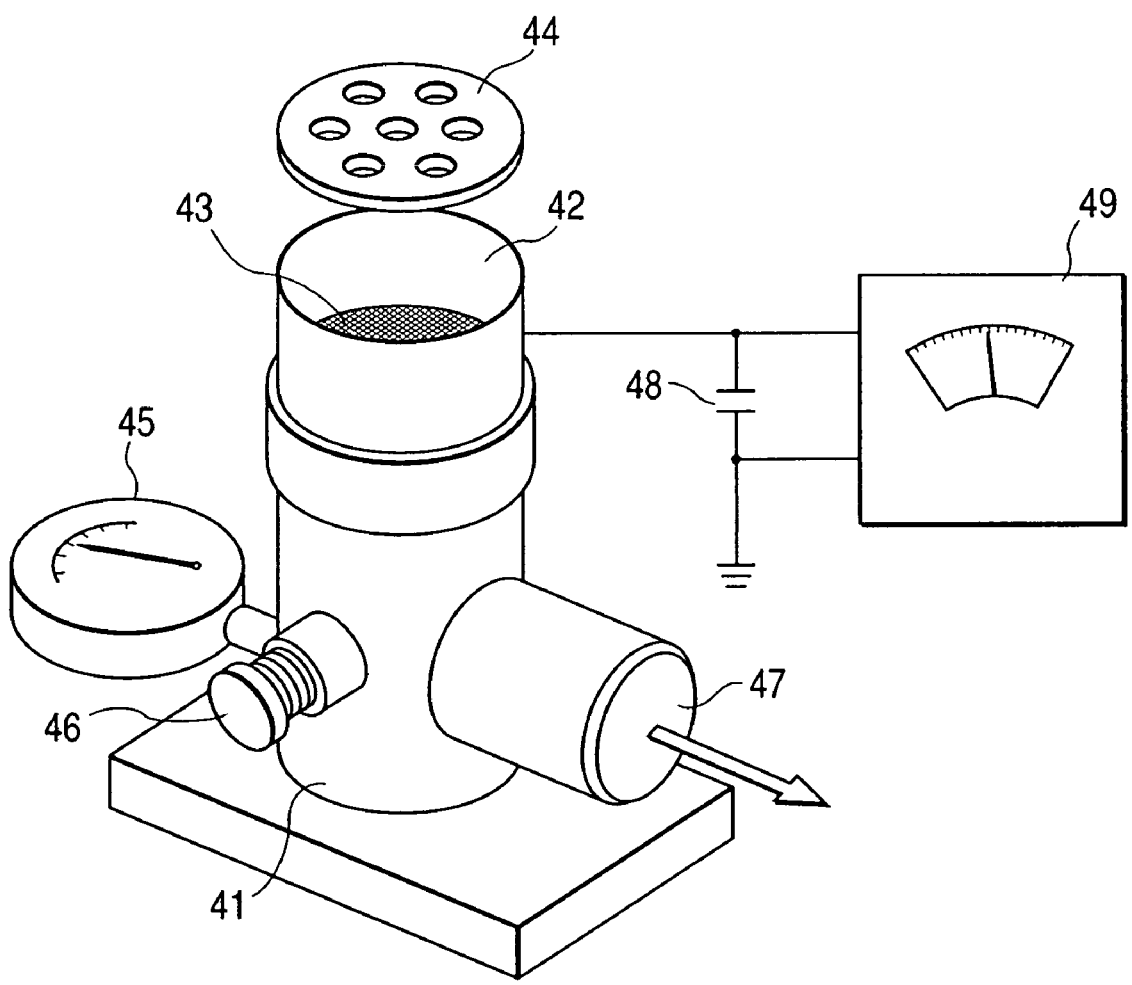
FIG. 7 is a schematic view showing a blow-off charge level measuring apparatus for measuring the charge level of the toner.

The method for measuring a charge quantity (two component triboelectric charge amount) by a two component method used in the present invention is as indicated below. For measurement, a charge amount measuring apparatus as shown in FIG. 7 is used. First, under a certain environment, a mixture of 9.5 g of EFV 200/300 (tradename, produced by Powdertech Co., Ltd.) as a carrier and 0.5 g of toner to be measured is added into a 50 to 100 mL capacity polyethylene bottle, which is then placed in a shaker set under shaking conditions of a fixed shaking width of 100 mm and a shaking speed of 100 strokes per minute and shaken for a predetermined period of time. Then, 1.0 to 1.2 g of the shaken mixture is charged in a measurement container 42 (made of metal) provided with a 500-mesh screen 43 at the bottom of the charge amount measuring apparatus shown in FIG. 7 and covered with a metal lid 44. The total mass of the measurement container 42 is weighed and denoted by WI (g). Then, an aspirator (not shown), in which at least the part contacting with the measurement container 42 is composed of an insulator, is operated to effect suction through a suction port 47 while pressure is so regulated as to be 2450 Pa (250 mmAq) with a vacuum gauge 45 by adjusting an airflow control valve 46. In this state, suction is continued for 1 minute to remove the toner. The reading at this time of a potential meter 49 is denoted by V (volts). Here, 48 designates a capacitor having a capacitance C (μF). The total mass of the measuring apparatus after the suction is measured and denoted by W2 (g). Then, the triboelectric charge amount (μC/g) of the toner is calculated by the following equation:

$$\text{Triboelectric charge amount } (\mu C/g) = C \times V/(W1-W2).$$

<Molecular Weight Distribution of Binder Resin>

It is preferred that the binder resin used as a constituent material of the electrostatic charge image developing toner of the present invention shows a low molecular weight region peak in the range from 3,000 to 15,000 in the molecular weight distribution by gel permeation chromatography (GPC), in particular, when it is prepared by a pulverization method. That is, if the GPC peak in the low molecular weight region exceeds 15,000, improvement in transfer efficiency may in some cases become insufficient. On the other hand, the use of a binder resin having a GPC peak in the low molecular weight region of less than 3,000 is not desirable since fusion tends to occur at the time of surface treatment.

In the present invention, the molecular weight of the binder resin is measured by gel permeation chromatography (GPC). A specific method for the measurement by GPC may include the following method: the toner is beforehand extracted with THF (tetrahydrofuran) solvent for 20 hours by means of a Soxhlet extractor, and the sample thus obtained is used for measurement of molecular weight by using columns of Shodex A-801, 802, 803, 804, 805, 806 and 807, (trade names, made by Showa Denko K.K.) connected in series, and using a calibration curve of reference polystyrene resin. In the present invention, it is preferred to use a binder resin having a ratio (Mw/Mn), which is a ratio of the weight average molecular weight (Mw) and number average molecular weight (Mn) thus measured, in the range of from 2 to 100.

<Glass Transition Point of Toner>

It is preferred that the toner of the present invention is so prepared as to have a glass transition point Tg of 40 to 75° C., more preferably 52 to 70° C., by using appropriate materials in consideration of fixing property and shelf life. In this case, the glass transition point Tg of the toner is measured using a high-precision differential scanning calorimeter in internal heat, input compensation type, for example, DSC-7, manufactured by Perkin Elmer Co., according to ASTM D3418-82. In the present invention, when measuring the glass transition point Tg, the temperature of a sample to be measured is once elevated to record all the thermal hysteresis and then quickly cooled. Again, the temperature of the sample is elevated at a temperature rise rate of 10° C./minute within the temperature range of 0 to 200° C. A DSC curve obtained based on the results of measurements under these conditions may be suitably used.

<Image Forming Method>

The electrostatic charge image developing toner of the present invention described above is particularly preferably applied to an image forming method comprising at least a charging step of charging an electrostatic latent image bearing member by applying a voltage to a charging member from the outside, a step of forming an electrostatic charge image on the charged electrostatic latent image bearing member, a developing step of developing the electrostatic charge image by using a toner to form a toner image on the electrostatic latent image bearing member, a transfer step of transferring the toner image on the electrostatic latent image bearing member to a recording medium, and a heat-fixing step of thermally fixing the toner image on the recording medium thereto. Alternatively, the toner of the present invention may be particularly preferably applied to the above-described method in which the transfer step comprises a first transfer step of transferring the toner image on the electrostatic latent image bearing member to an intermediate transfer member and a second transfer step of transferring the toner image on the intermediate transfer member to the recording medium.

It should be noted that the culture of microorganisms, the recovery of PHA from microorganism cells, resin compositions, molded articles or the like, and toner binder resins or the like of the present invention are not limited to those described in the above methods.

EXAMPLES

The present invention will be further described in the following Examples and Comparative Examples. The Examples are illustrative of the best mode of the embodiment of the present invention, but the present invention is not limited thereto. The number of parts in each of the following compositions represents part by mass, and "%" means a percentage on the basis of mass, unless otherwise specified.

PHA

First, a method for preparing polyhydroxyalkanoate of the present invention comprising a microbiological production step and a chemical processing step is shown below (Preparation Examples A-1 to A-4, Comparative Preparation Example A-1, and Examples A-1 to A-8).

Preparation Example A-1

Each 200 ml of an M9 culture medium containing 0.5% of sodium glutamate and 0.1% of 4-(phenylsulfanyl)butyric acid was charged into 24 shaking flasks of 500 ml volume, sterilized under high temperature and high pressure, and cooled to room temperature to prepare a culture medium. *Pseudomonas cichorii* YN2 strain was seeded on an M9 culture medium containing 0.5% of polypeptone and shaking-cultured at 30° C. for 8 hours to prepare a cell culture solution in advance. Each 2 ml of this culture solution was added to the above culture medium containing 4-(phenylsulfanyl)butyric acid as a matrix to shaking-culture the cells at 30° C. and 125 strokes/minute. Sixty-four hours later, the cells were collected by centrifugation, washed with cold methanol once, and then dried under vacuum.

The pellet of this dried cell was suspended in 150 ml of chloroform and stirred at 35° C. for 16 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 889 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 24,400, and the weight average molecular weight Mw was 55,100.

Figure 8:
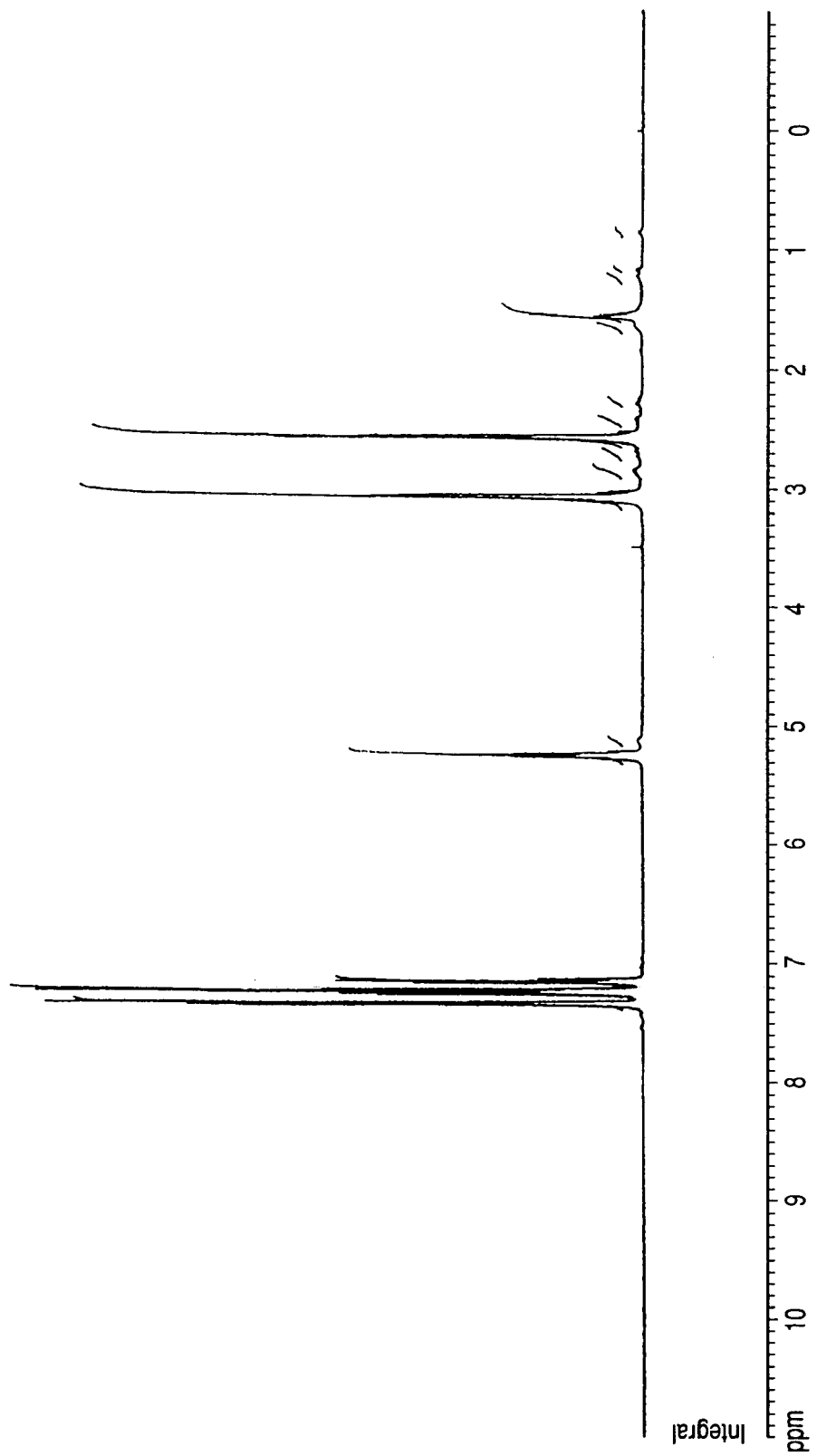
FIG. 8 shows a $^1$H-NMR spectrum of the compound prepared in Preparation example A-1.

The structure of the resultant PHA was determined by $^1$H-NMR (FT-NMR: Bruker DPX400; resonance frequency: 400 MHz; measurement nuclear species: $^1$H; solvent used: CDCl$_3$; reference: capillary-encapsulated TMS/CDCl$_3$; measurement temperature: room temperature) The $^1$H-NMR spectrum is shown in FIG. 8, and the identified results are shown in Table 1. As a result, the PHA was found to contain 95 mol % of 3-hydroxy-4-(phenylsulfanyl)butyric acid shown by chemical formula (22) and total 5 mol % of the others (straight-chained 3-hydroxyalkanoic acid having 4 to 12 carbon atoms and 3-hydroxyalk-5-enoic acid having 10 or 12 carbon atoms).

TABLE 1

(22)

| Chemical shift (ppm) | Identified result |
|---|---|
| 2.58 | b1 |
| 3.09 | d1 |
| 5.27 | c1 |
| 7.15 | h1 |
| 7.26 | g1, i1 |
| 7.36 | f1, j1 |

Polyhydroxyalkanoate obtained here was utilized in the next reaction.

403 mg of polyhydroxyalkanoate was charged in a 100 ml round bottomed flask, and 10 ml of chloroform was added and dissolved. The flask was placed in an ice bath, and methachloroperbenzoic acid in 20 ml of chloroform was gradually added followed by stirring. After stirring for 75 minutes cooling on ice bath, 100 ml of water and 1,000 mg of sodium bisulfite were added. Then, the mixture was extracted by chloroform to collect the polymer. Next, the mixture was washed with 2 portions of 100 ml of ethanol and dried under a reduced pressure to obtain 377 mg of the polymer.

The average molecular weight of the resultant PHA was evaluated by gel permeation chromatography (GPC; Tosoh HLC-8020, column: two Polymer Laboratory PlgelM-IXED-C (5 μm); moving phase solvent: DMF containing 0.1 wt % of LiBr chloroform; polystyrene equivalent), and hence it was found that the number average molecular weight Mn was 14,100, and the weight average molecular weight Mw was 39,200.

Figure 9:
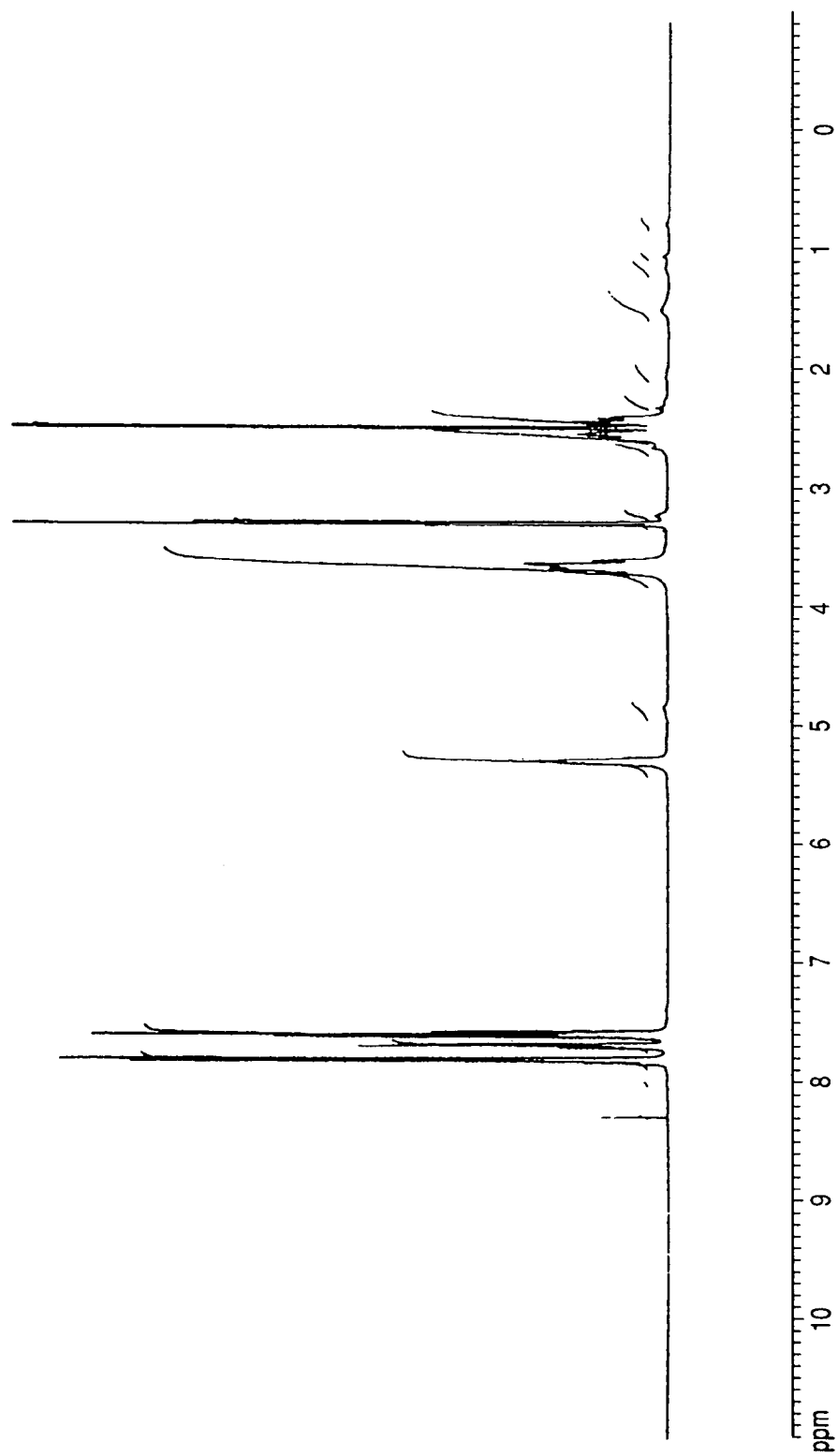
FIG. 9 shows a $^1$H-NMR spectrum of the compound prepared in Preparation example A-1.

The structure of the resultant polymer was determined by $^1$H-NMR (FT-NMR: Bruker DPX400; resonance frequency: 400 MHz; measurement nuclear species: $^1$H; solvent used: DMSO-$d_6$; reference: capillary-encapsulated DMSO-$d_6$; measurement temperature: room temperature). The $^1$H-NMR spectrum is shown in FIG. 9, and the identified results are shown in Table 2. As a result, the PHA was found to contain 98 mol % of 3-hydroxy-4-(phenylsulfonyl)butyric acid shown by chemical formula (23) and total 2 mol % of the others (straight-chained 3-hydroxyalkanoic acid having 4 to 12 carbon atoms and 3-hydroxyalk-5-enoic acid having 10 or 12 carbon atoms).

By scaling up the above preparation method, 50 g of PHA was obtained and it was referred to as PHAA-1.

TABLE 2

(23)

| Chemical shift (ppm) | Identified result |
| --- | --- |
| 2.32–2.69 | b2 |
| 3.68 | d2 |
| 5.31 | c2 |
| 7.61 | f2, h2 |
| 7.71 | g2 |
| 7.83 | e2, i2 |

Preparation Example A-2

Each 200 ml of an M9 culture medium containing 0.5% of polypeptone (from NIHON PHARMACEUTICAL CO., LTD.) and 0.1% of 5-(phenylsulfanyl)valeric acid was charged into 24 shaking flasks of 500 ml volume, sterilized under high temperature and high pressure, and cooled to room temperature to prepare a culture medium.

*Pseudomonas cichorii* YN2 strain was seeded on an M9 culture medium containing 0.5% of polypeptone and shaking-cultured at 30° C. for 8 hours to prepare a cell culture solution in advance. Each 2 ml of this culture solution was added to the above culture medium containing 5-(phenylsulfanyl)valeric acid as a matrix to shaking-culture the cells at 30° C. and 125 strokes/minute. Twenty-four hours later, the cells were collected by centrifugation, washed with cold methanol once, and then dried under vacuum.

The pellet of this dried cell was suspended in 200 ml of chloroform and stirred at 35° C. for 17 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 2,939 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 227,100, and the weight average molecular weight Mw was 671,300.

Figure 10:
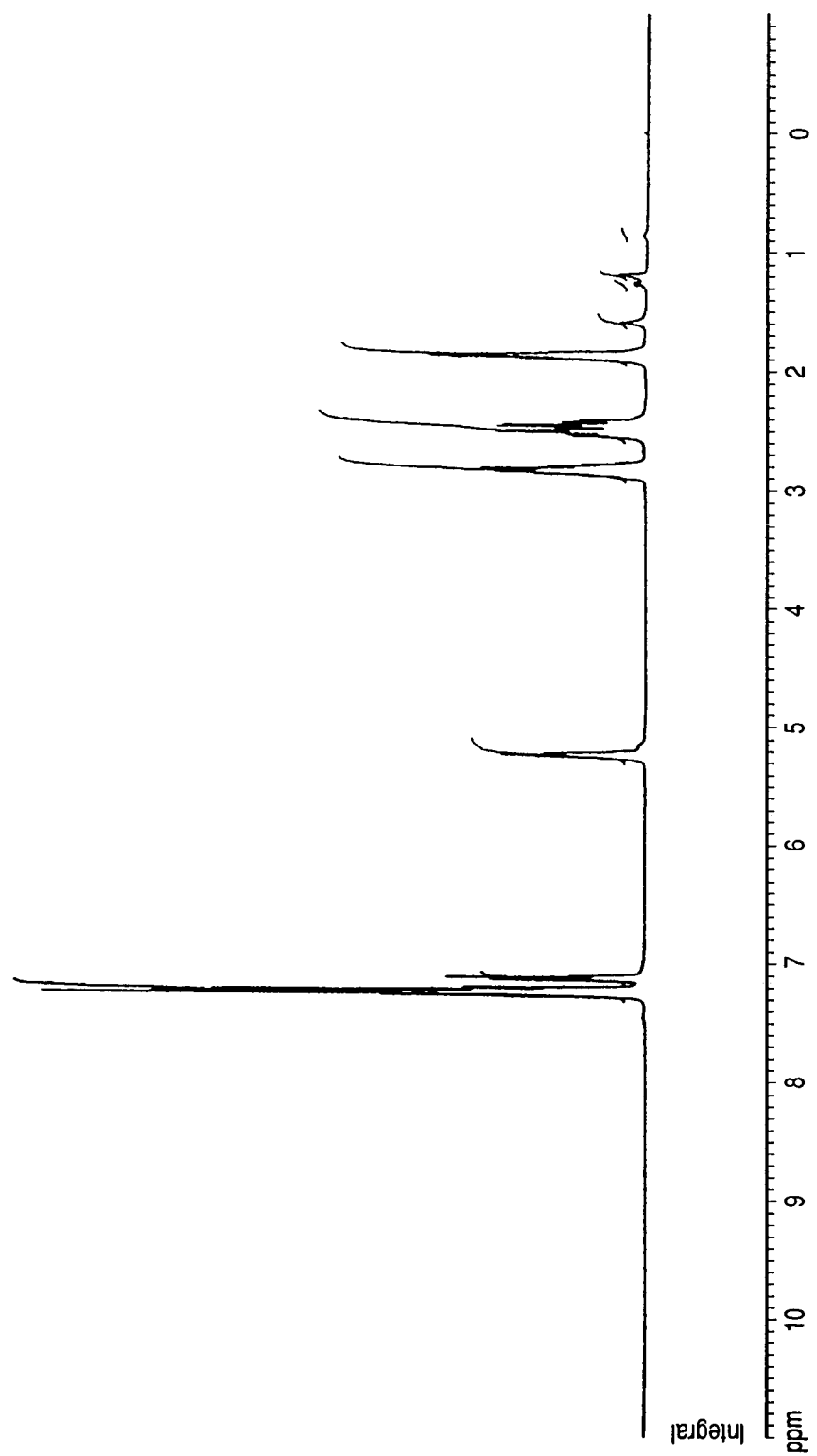
FIG. 10 shows a $^1$H-NMR spectrum of the compound prepared in Preparation example A-2.

The structure of the resultant PHA was determined by $^1$H-NMR (FT-NMR: Bruker DPX400; resonance frequency: 400 MHz; measurement nuclear species: $^1$H; solvent used: $CDCl_3$; reference: capillary-encapsulated TMS/$CDCl_3$; measurement temperature: room temperature). The $^1$H-NMR spectrum is shown in FIG. 10, and the identified results are shown in Table 3. As a result, the PHA was found to contain 94 mol % of 3-hydroxy-5-(phenylsulfanyl)valeric acid shown by chemical formula (24) and total 6 mol % of the others (straight-chained 3-hydroxyalkanoic acid having 4 to 12 carbon atoms and 3-hydroxyalk-5-enoic acid having 10 or 12 carbon atoms).

TABLE 3

(24)

| Chemical shift (ppm) | Identified result |
| --- | --- |
| 1.89 | d3 |
| 2.42–2.56 | b3 |
| 2.80–2.90 | e3 |
| 5.27 | c3 |
| 7.13 | i3 |
| 7.23–7.29 | g3, h3, j3, k3 |

Polyhydroxyalkanoate obtained here was utilized in the next reaction.

400 mg of polyhydroxyalkanoate was charged in a 100 ml round bottomed flask, and 10 ml of chloroform was added and dissolved. The flask was placed in an ice bath, and 1386 mg of methachloroperbenzoic acid in 20 ml of chloroform was gradually added followed by stirring. After stirring for 75 minutes cooling on ice bath, 100 ml of water and 3,020 mg of sodium bisulfite were added. Then, the mixture was extracted by chloroform to collect the polymer. Next, the mixture was washed with 2 portions of 100 ml of ethanol and dried under a reduced pressure to obtain 373 mg of the polymer.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 107,300, and the weight average molecular weight Mw was 275,500.

Figure 11:
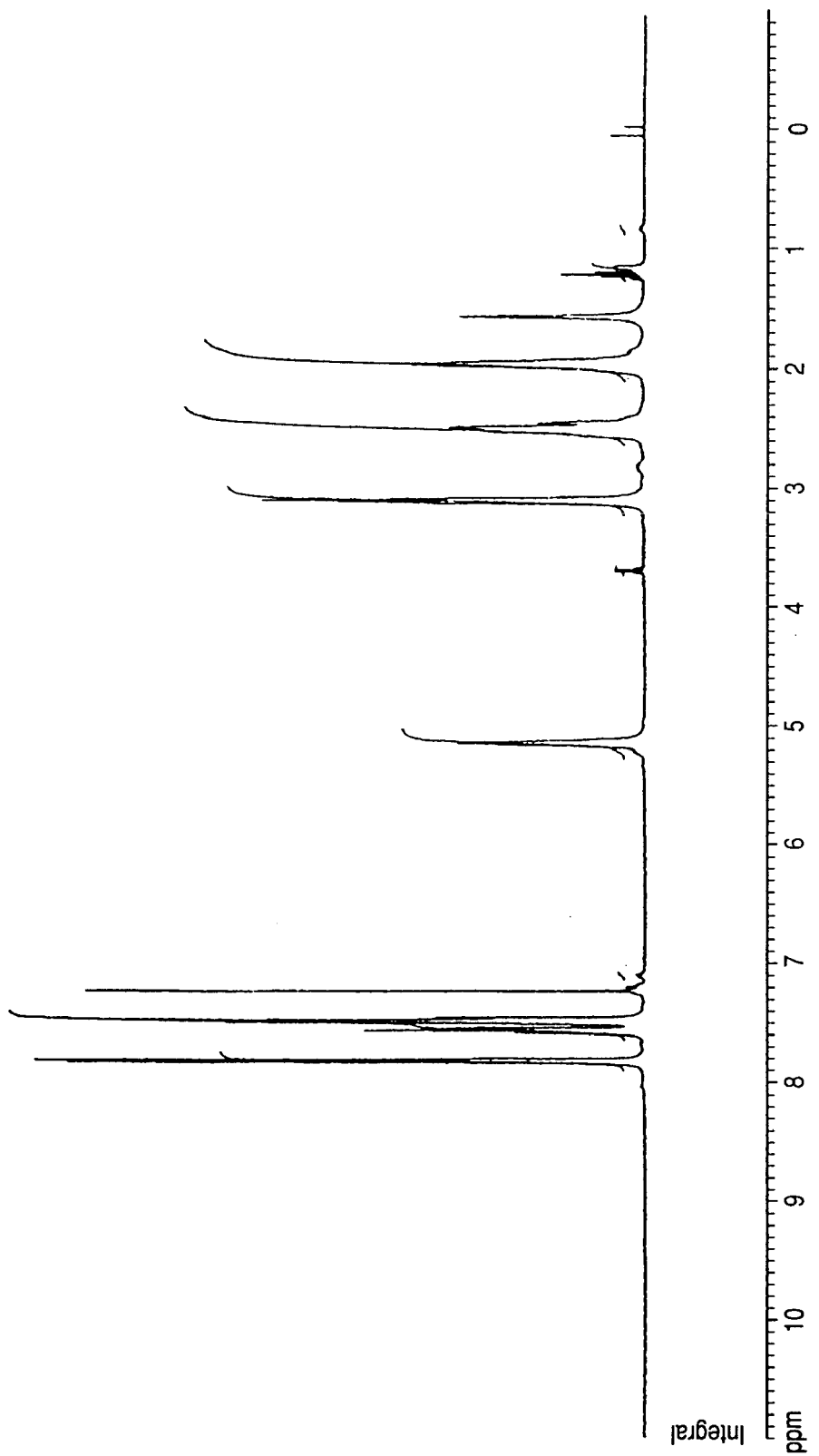
FIG. 11 shows a $^1$H-NMR spectrum of the compound prepared in Preparation example A-2.

The structure of the resultant polymer was determined by $^1$H-NMR (FT-NMR: Bruker DPX400; resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 11, and the identified results are shown in Table 4. As a result, the PHA was found to contain 91 mol % of 3-hydroxy-5-(phenylsulfonyl)valeric acid shown by chemical formula (25) and total 9 mol % of the others (straight-chained 3-hydroxyalkanoic acid having 4 to 12 carbon atoms and 3-hydroxyalk-5-enoic acid having 10 or 12 carbon atoms).

By scaling up the above preparation method, 50 g of PHA was obtained and it was referred to as PHAA-2.

TABLE 4

(25)

| Chemical shift (ppm) | Identified result |
|---|---|
| 1.99 | d4 |
| 2.47-2.60 | b4 |
| 3.12-3.16 | e4 |
| 5.18 | c4 |
| 7.51 | h4, j4 |
| 7.60 | i4 |
| 7.84 | g4, k4 |

Preparation Example A-3

Polyhydroxyalkanoate obtained here was utilized in the next reaction.

400 mg of polyhydroxyalkanoate was charged in a 100 ml round bottomed flask, and 10 ml of chloroform was added and dissolved. The flask was placed in an ice bath, and 463 mg of methachloroperbenzoic acid in 20 ml of chloroform was gradually added followed by stirring. After stirring for 75 minutes cooling on ice bath, 100 ml of water and 1,000 mg of sodium bisulfite were added. Then, the mixture was extracted by chloroform to collect the polymer. Next, the mixture was washed with 2 portions of 100 ml of ethanol and dried under a reduced pressure to obtain 366 mg of the polymer.

The average molecular weight of the resultant PHA was evaluated by gel permeation chromatography (Tosoh HLC-8020, column: two Polymer Laboratory PlgelMIXED-C (5 µm); moving phase solvent: DMF containing 0.1 wt % of LiBr; polystyrene equivalent), and hence it was found that the number average molecular weight Mn was 121,300, and the weight average molecular weight Mw was 286,500.

The structure of the resultant polymer was determined by $^1$H-NMR (FT-NMR: Bruker DPX400; resonance frequency: 400 MHz; measurement nuclear species: $^1$H; solvent used: CDCl$_3$; reference: capillary-encapsulated TMS/CDCl$_3$; measurement temperature: room temperature). As a result, the PHA was found to contain 63 mol % of 3-hydroxy-5-(phenylsulfinyl)valeric acid shown by chemical formula (26), 31 mol % of 3-hydroxy-5-(phenylsulfonyl)valeric acid shown by chemical formula (25), and total 9 mol % of the others (straight-chained 3-hydroxyalkanoic acid having 4 to 12 carbon atoms and 3-hydroxyalk-5-enoic acid having 10 or 12 carbon atoms).

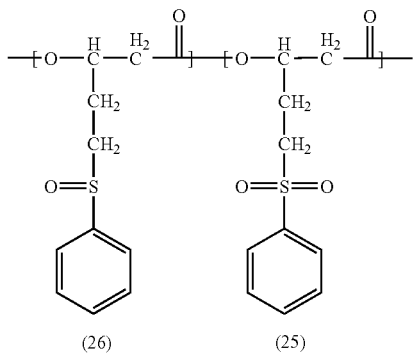

(26)    (25)

By scaling up the above preparation method, 50 g of PHA was obtained and it was referred to as PHAA-3.

Preparation Example A-4

Each 200 ml of an M9 culture medium containing 0.5% of polypeptone (from NIHON PHARMACEUTICAL CO., LTD.), 0.1% of 5-(phenylsulfanyl)valeric acid, and 1.0 mM of 5-phenylvaleric acid was charged into 8 shaking flasks of 500 ml volume, sterilized under high temperature and high pressure, cooled, and seeded with Pseudomonas cichorii YN2 strain. The cells were shaking-cultured at 30° C. and 125 strokes/minute. Forty-four hours later, the cells were collected by centrifugation, washed with cold methanol once, and then dried under vacuum.

The pellet of this dried cell was suspended in 100 ml of chloroform and stirred at 35° C. for 16 hours to extract PHA. After filtering by a membrane filter of the pore size of 0.45 µm, the extract was concentrated by a rotary evaporator. The concentrated solution was added to cold methanol, and PHA was reprecipitated. Only the precipitate was collected and dried under vacuum. The resultant PHA was weighed and found to be 929 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 141,200, and the weight average molecular weight Mw was 393,800.

Figure 12:
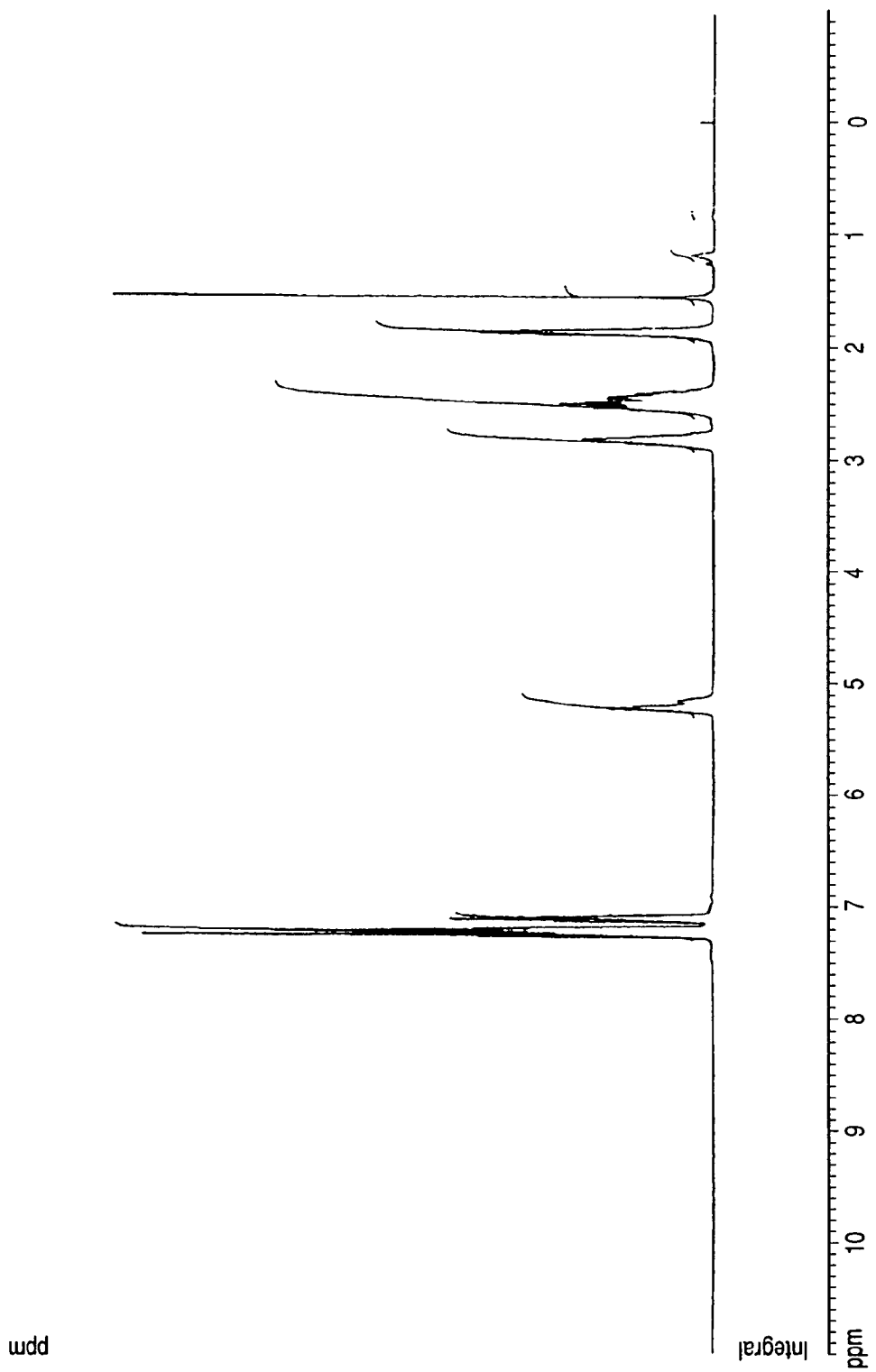
FIG. 12 shows a $^1$H-NMR spectrum of the compound prepared in Preparation example A-4.

The structure of the resultant PHA was determined by $^1$H-NMR (FT-NMR: Bruker DPX400; resonance frequency: 400 MHz; measurement nuclear species: $^1$H; solvent used: CDCl$_3$; reference: capillary-encapsulated TMS/CDCl$_3$; measurement temperature: room temperature) The $^1$H-NMR spectrum is shown in FIG. 12 and the identified results are shown in Table 5. As a result, the polyhydroxyalkanoate copolymer was found to contain 73 mol % of 3-hydroxy-5-(phenylsulfanyl)valeric acid shown by chemical formula (27), 21 mol % of 3-hydroxy-5-phenylvaleric acid shown by chemical formula (28), and total 6 mol % of the others (straight-chained 3-hydroxyalkanoic acid having 4 to 12 carbon atoms and 3-hydroxyalk-5-enoic acid having 10 or 12 carbon atoms).

TABLE 5

(27)

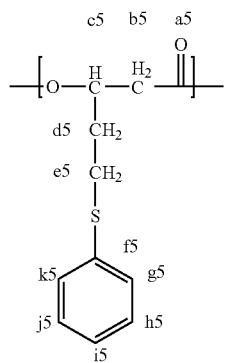

(28)

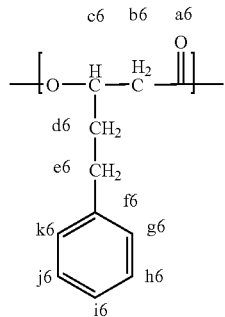

| Chemical shift (ppm) | Identified result |
|---|---|
| 1.88 | d5, d6 |
| 2.39- 2.57 | b5, b6, e6 |
| 2.78-2.88 | e5 |
| 5.18-5.27 | c5, c6 |
| 7.13 | i5, g6, i6, k6 |
| 7.24 | g5, h5, j5, k5, h6, j6 |

851 mg of a polyhydroxyalkanoate copolymer containing 73 mol % of 3-hydroxy-5-(phenylsulfanyl)valeric acid, 21 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms) as monomer units was added to a 300 ml round bottomed flask, and then 60 ml of dichloromethane was added and dissolved. The mixture was placed in an ice bath, and 9 ml of acetic acid and 2,537 mg of 18-crown-6-ether were added followed by stirring. Next, 2,020 mg of potassium permanganate was gradually added in an ice bath, followed by stirring at room temperature for 20 hours. After the reaction was completed, 50 ml of water and 6,030 mg of sodium bisulfite were added. Then, the solution was made to be pH 1 by adding 1.0N hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis by using chloroform. After purification, 1,137 mg of the desired PHA was obtained by drying under a reduced pressure.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 42,800, and the weight average molecular weight Mw was 112,200.

Figure 13:
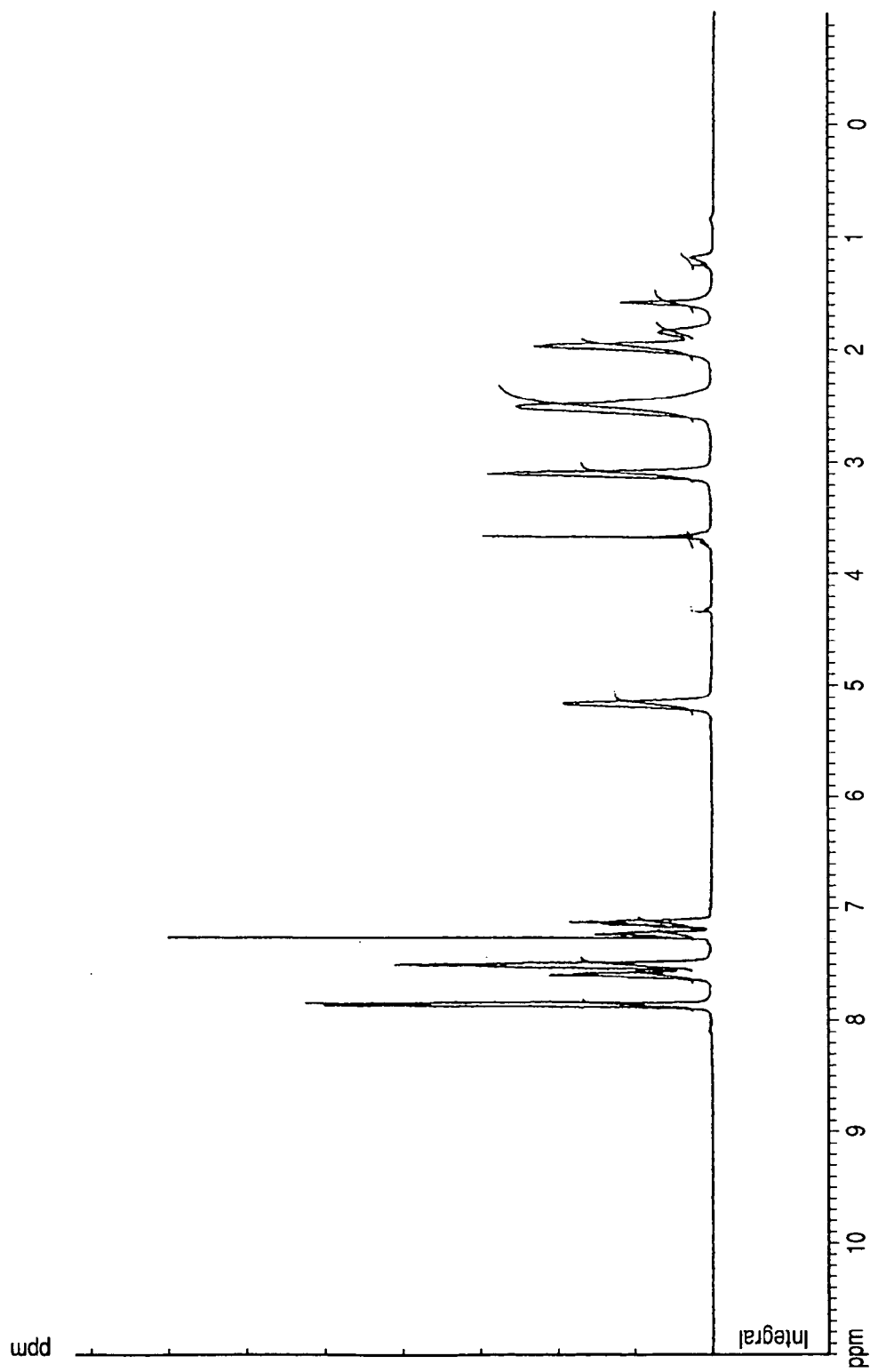
FIG. 13 shows a $^1$H-NMR spectrum of the compound prepared in Preparation example A-4.

In order to determine the construction of the resultant PHA, analysis was performed by $^1$H-NMR (FT-NMR: Bruker DPX400; resonance frequency: 400 MHz; measurement nuclear species: $^1$H; solvent used: $CDCl_3$; reference: capillary-encapsulated $TMS/CDCl_3$; measurement temperature: room temperature). The $^1$H-NMR spectrum is shown in FIG. 13, and the identified results are shown in Table 6. As a result, the PHA was found to be a polyhydroxyalkanoate copolymer containing 71 mol % of 3-hydroxy-5-(phenylsulfonyl)valeric acid shown by chemical formula (29), 23 mol % of 3-hydroxy-5-phenylvaleric acid shown by chemical formula (30), and total 6 mol % of the others (straight-chained 3-hydroxyalkanoic acid having 4 to 12 carbon atoms and 3-hydroxyalk-5-enoic acid having 10 or 12 carbon atoms).

By scaling up the above preparation method, 50 g of PHA was obtained and it was referred to as PHAA-4.

TABLE 6

(29)

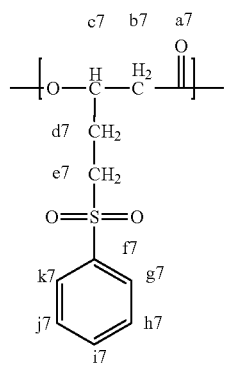

(30)

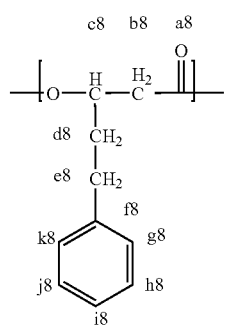

| Chemical shift (ppm) | Identified result |
|---|---|
| 1.88 | d8 |
| 2.00 | d7 |
| 2.54 | b8, e8, b7 |
| 3.15 | e7 |
| 5.18 | c8, c7 |
| 7.13 | g8, i8, k8 |
| 7.24 | h8, j8 |
| 7.51 | h7, j7 |
| 7.58 | i7 |
| 7.86 | g7, k7 |

Comparative Preparation Example A-1

200 ml of an M9 culture medium containing 0.5% of a yeast extract (from Oriental Yeast Co., Ltd.) was seeded with *Pseudomonas cichorii* H45 strain and shaking-cultured at 30° C. and 125 strokes/minute for 8 hours to prepare a spawn. 25 L of an M9 culture medium containing 0.1% of 5-phenylvaleric acid and 0.5% of D-glucose was prepared-in a 50 L jar fermenter, and the spawn was charged thereto and cultured with aeration and stirring at 30° C., 70 rpm, and 9.4 L/minute of an aeration amount. After 48 hours, the cells were collected by centrifugation, resuspended in 25 L of an M9 culture medium containing 0.1% of 5-phenylvaleric acid and 0.5% of D-glucose and not containing a nitrogen source ($NH_4Cl$), and further cultured with aeration and stirring at 30° C., 70 rpm, and 9.4 L/minute of an aeration amount. After 48 hours, the cells were collected by centrifugation, washed once with cold methanol, and lyophilized.

The lyophilized pellets were suspended in 200 ml of chloroform, stirred at 60° C. for 20 hours, and extracted. After filtered by a membrane filter of the pore size of 0.45 μm, the extract was concentrated by a rotary evaporator. The concentrated solution was reprecipitated in cold methanol, and only the precipitate was collected and dried under vacuum to obtain 15.0 g of a resin composition.

A portion of the resin composition was taken, subjected to methanolysis in the usual manner and then analyzed by a Gas Chromatography-Mass Spectrometer (GC-MS, Shimadzu QP-5050, EI method) to identify the methylesterified product of the monomer unit composing the resin composition. As a result, the resin composition was found to be comprised of PHA containing a 3-hydroxy-5-phenylvaleric acid unit only.

By scaling up the above preparation method, 50 g of PHA was obtained and it was referred to as PHAA-5.

Example A-1

Each 200 ml of an M9 culture medium containing 0.5% of polypeptone (from NIHON PHARMACEUTICAL CO., LTD.), 0.1% of 5-(phenylsulfanyl)valeric acid, and 1.0 mmol of 5-phenylvaleric acid was charged into 8 shaking flasks of 500 ml volume, sterilized under high temperature and high pressure, cooled, and seeded with *Pseudomonas cichorii* YN2 strain. The cells were shaking-cultured at 30° C. and 125 strokes/minute. Forty-four hours later, the cells were collected by centrifugation, washed with cold methanol once, and then dried under vacuum.

The pellet of this dried cell was suspended in 100 ml of chloroform and stirred at 35° C. for 16 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 929 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 141,200, and the weight average molecular weight Mw was 393,800.

Figure 14:
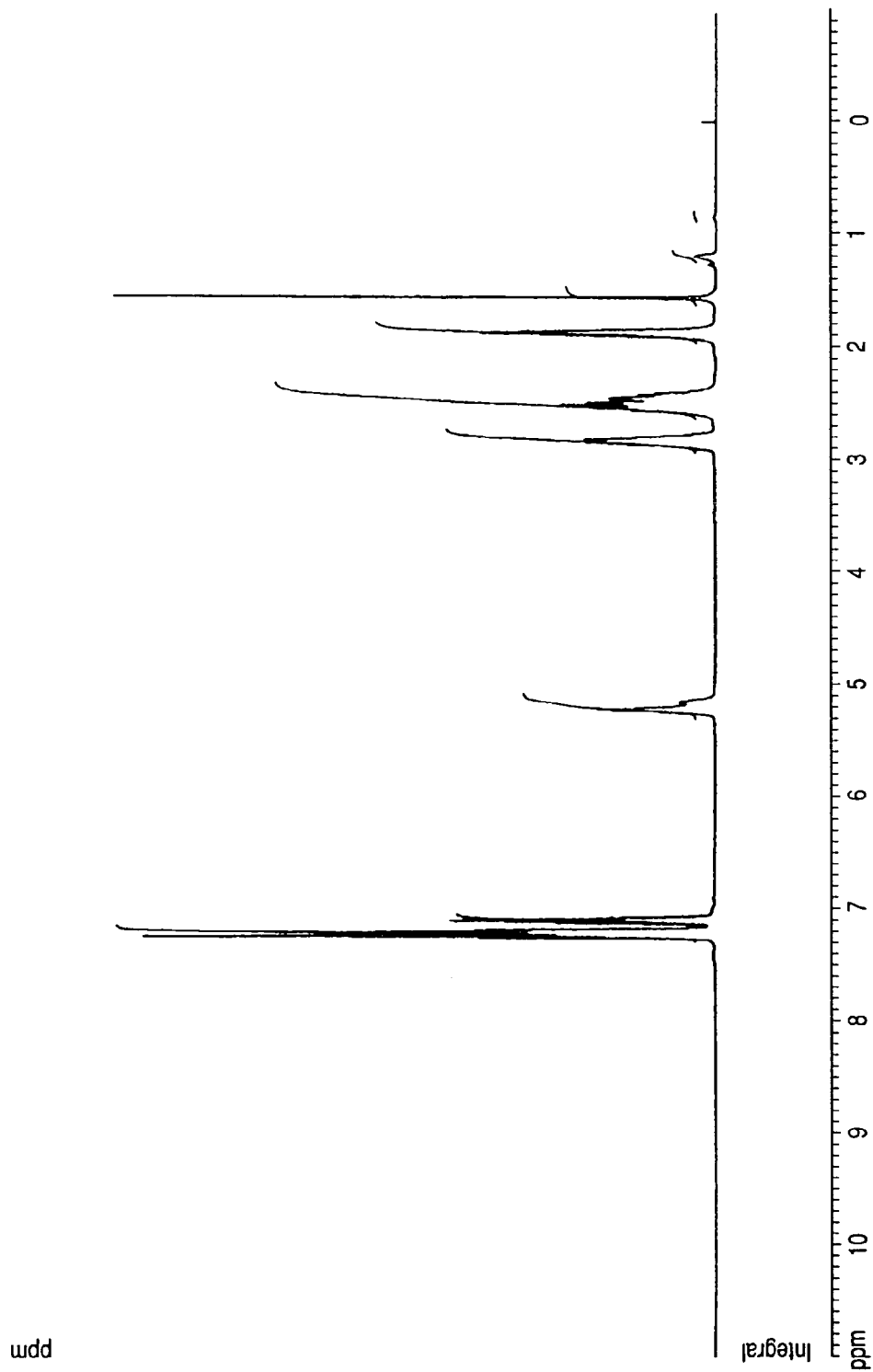
FIG. 14 shows a $^1$H-NMR spectrum of the compound prepared in example A-1.

The structure of the resultant PHA was determined by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature). The $^1$H-NMR spectrum is shown in FIG. 14 and the identified results are shown in Table 7. As a result, the polyhydroxyalkanoate copolymer was found to contain 73 mol % of 3-hydroxy-5-(phenylsulfanyl)valeric acid, 21 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms), as shown by chemical formula (31).

TABLE 7

(31)

[chemical structures showing two repeating units with labeled positions c1, b1, a1, d1, e1, f1, k1, j1, i1, h1, g1 (left structure with S) and c2, b2, a2, d2, e2, f2, k2, j2, i2, h2, g2 (right structure)]

| Chemical shift (ppm) | Scission | Identified result |
|---|---|---|
| 1.88 | br | d1, d2 |
| 2.39-2.57 | m | b1, b2, e2 |
| 2.78-2.88 | m | e1 |
| 5.18-5.27 | m | c1, c2 |
| 7.13 | m | i1, g2, i2, k2 |
| 7.24 | m | g1, h1, j1, k1, h2, j2 |

Example A-2

851 mg of a polyhydroxyalkanoate copolymer containing 73 mol % of 3-hydroxy-5-(phenylsulfanyl)valeric acid, 21 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms) as monomer units was added to a 300 ml round bottomed flask, and then 60 ml of dichloromethane was added and dissolved. The mixture was placed in an ice bath, and 9 ml of acetic acid and 2,537 mg of 18-crown-6-ether were added followed by stirring. Next, 2,020 mg of potassium permanganate was gradually added in an ice bath followed by stirring at room temperature for 20 hours. After the reaction was completed, 50 ml of water and 6,030 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. 1,137 mg of the desired PHA was obtained by drying under a reduced pressure.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 42,800, and the weight average molecular weight Mw was 112,200.

Figure 15:
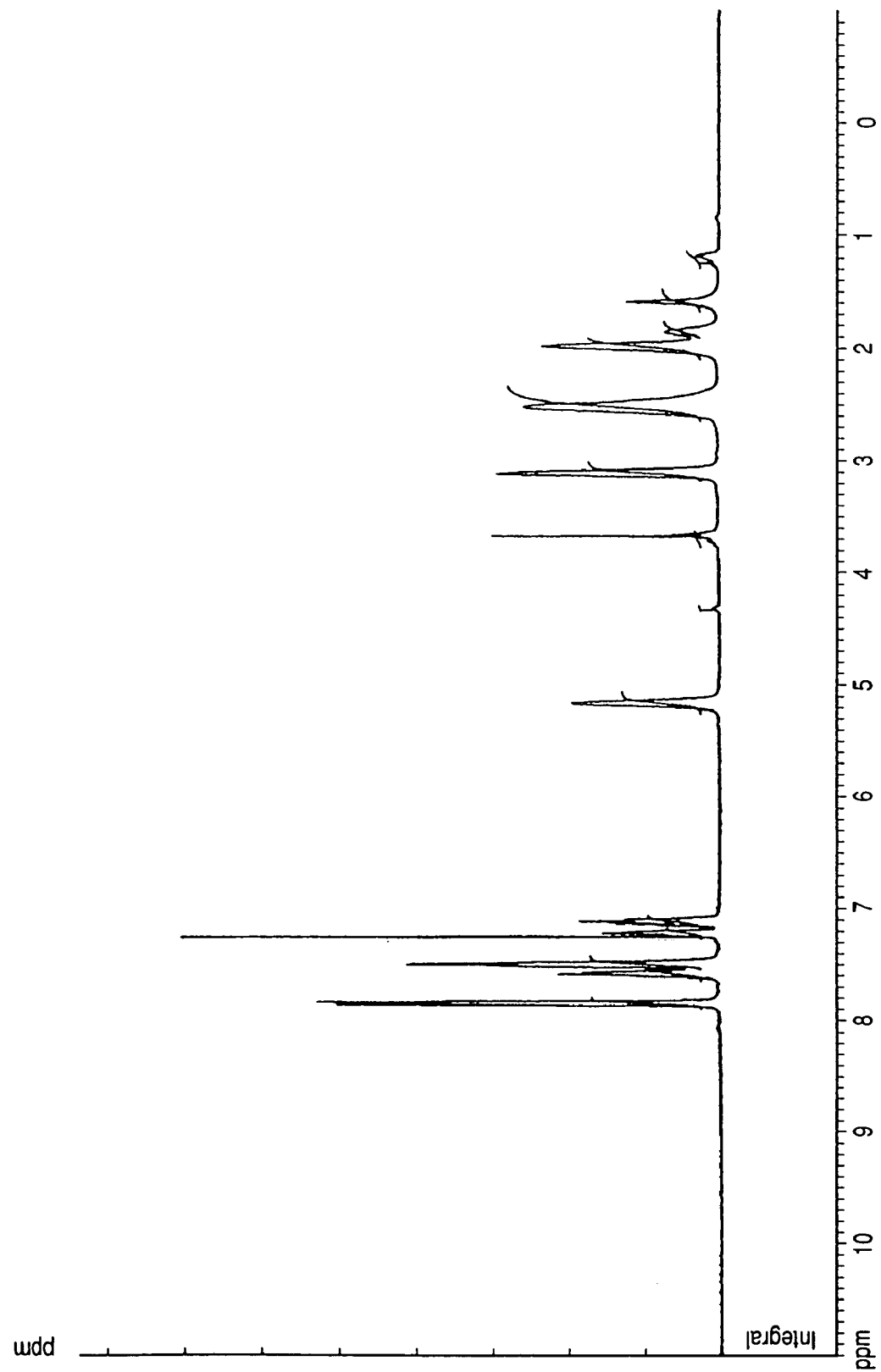
FIG. 15 shows a $^1$H-NMR spectrum of the compound prepared in example A-2.

In order to determine the construction of the resultant PHA, analysis was performed by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/CDCl$_3$; measurement temperature: room temperature). The $^1$H-NMR spectrum is shown in FIG. 15, and the identified results are shown in Table 8. As a result, the PHA was found to be a polyhydroxyalkanoate copolymer containing 71 mol % of 3-hydrbxy-5-(phenylsulfonyl)valeric acid, 23 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms), as shown by chemical formula

TABLE 8

(32)

| Chemical shift (ppm) | Scission | Identified result |
|---|---|---|
| 1.88 | br | d2 |
| 2.00 | br | d3 |
| 2.54 | br | b2, e2, b3 |
| 3.15 | br | e3 |
| 5.18 | br | c2, c3 |
| 7.13 | m | g2, i2, k2 |
| 7.24 | m | h2, j2 |
| 7.51 | br | h3, j3 |
| 7.58 | m | i3 |
| 7.86 | m | g3, k3 |

Example A-3

Each 200 ml of an M9 culture medium containing 0.5% of polypeptone (from NIHON PHARMACEUTICAL CO., LTD.), 0.1% of 5-(phenylsulfanyl)valeric acid, and 1.5 mmol of 5-phenylvaleric acid was charged into 8 shaking flasks of 500 ml volume, sterilized under high temperature and high pressure, cooled, and seeded with *Pseudomonas cichorii* YN2 strain. The cells were shaking-cultured at 30° C. and 125 strokes/minute. Thirty-nine hours later, the cells were collected by centrifugation, washed with cold methanol once, and then dried under vacuum.

The pellet of this dried cell was suspended in 100 ml of chloroform and stirred at 35° C. for 97 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 1,081 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 232,200, and the weight average molecular weight Mw was 554,000.

Figure 16:
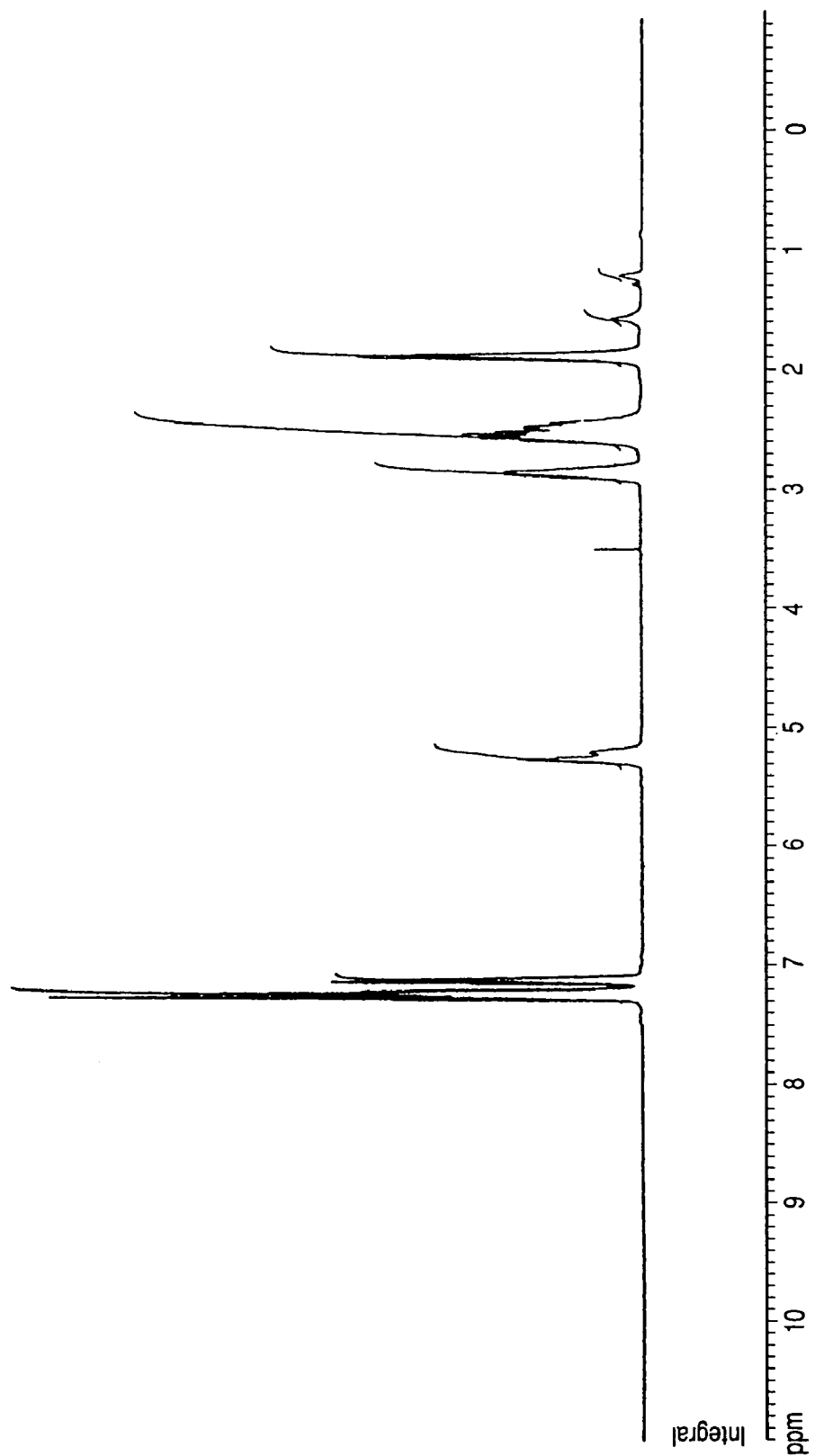
FIG. 16 shows a $^1$H-NMR spectrum of the compound prepared in example A-3.

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 16. As a result, the polyhydroxyalkanoate copolymer was found to contain 66 mol % of 3-hydroxy-5-(phenylsulfanyl)valeric acid, 29 mol % of 3-hydroxy-5-phenylvaleric acid, and total 5 mol % of the others (straight-chained 3-hydroxyalkanoic acid having 4 to 12 carbon atoms and 3-hydroxyalk-5-enoic acid having 10 or 12 carbon atoms), as shown by chemical formula (33).

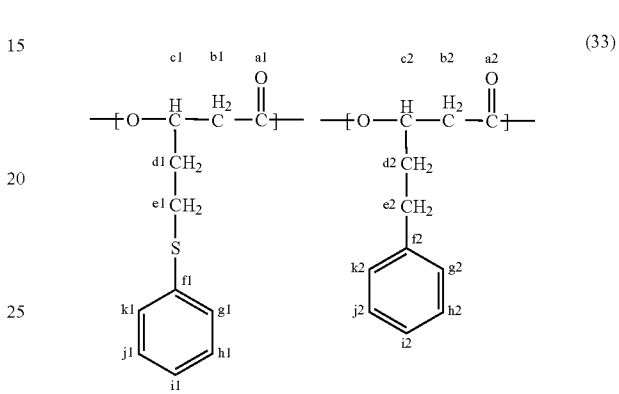

Example A-4

850 mg of a polyhydroxyalkanoate copolymer containing 66 mol % of 3-hydroxy-5-(phenylsulfanyl)valeric acid, 29 mol % of 3-hydroxy-5-phenylvaleric acid, and total 5 mol % of the others (straight-chained 3-hydroxyalkanoic acid having 4 to 12 carbon atoms and 3-hydroxyalk-5-enoic acid having 10 or 12 carbon atoms) as monomer units was added to a 300 ml round bottomed flask, and then 60 ml of dichloromethane was added and dissolved. The mixture was placed in an ice bath, and 9 ml of acetic acid and 2,306 mg of 18-crown-6-ether were added followed by stirring. Next, 1,839 mg of potassium permanganate was gradually added in an ice bath followed by stirring at room temperature for 20 hours. After the reaction was completed, 50 ml of water and 3,000 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 929 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 73,400, and the weight average molecular weight Mw was 195,000.

Figure 17:
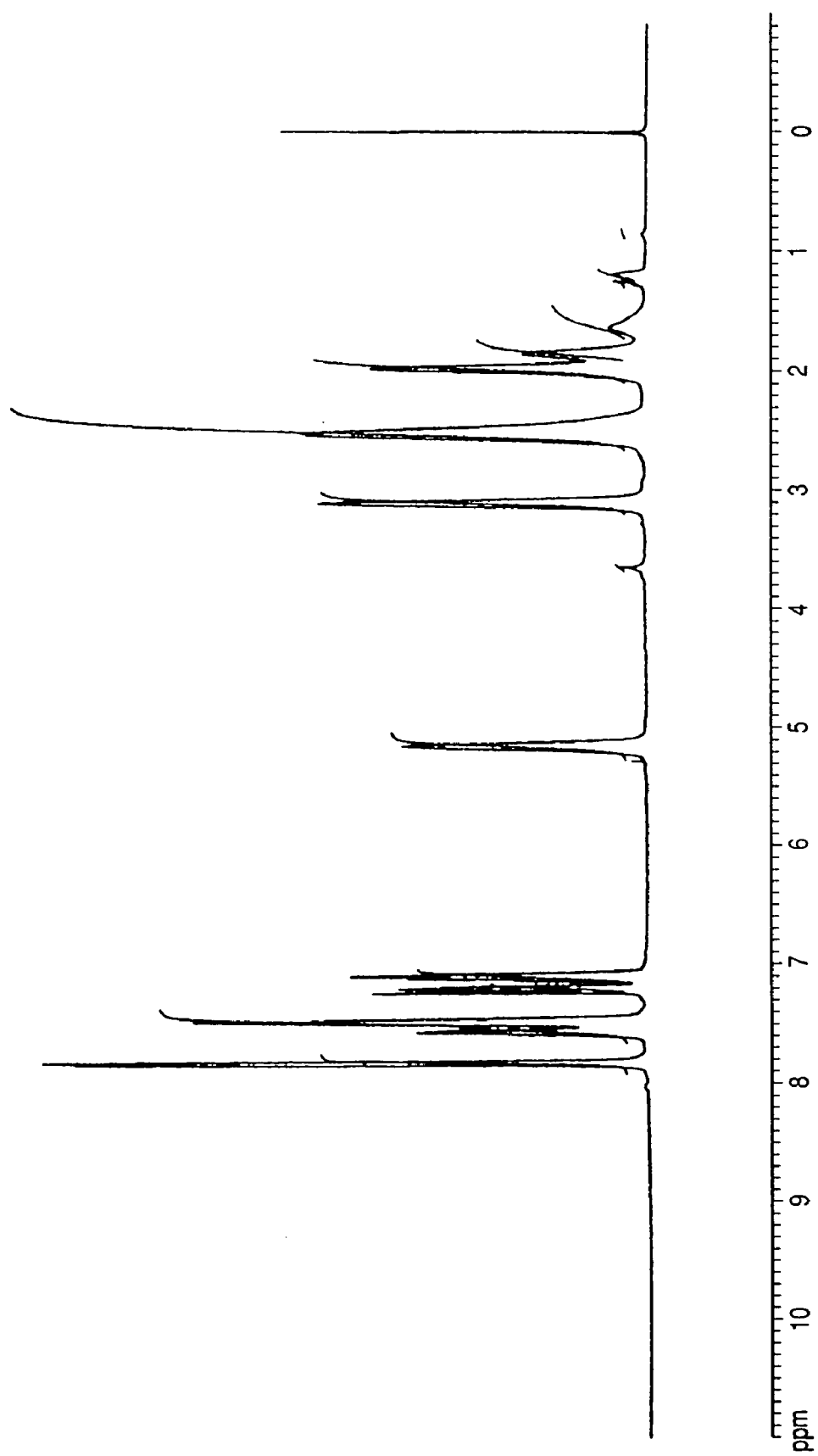
FIG. 17 shows a $^1$H-NMR spectrum of the compound prepared in example A-4.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 17. As a result, the polyhydroxyalkanoate copolymer was found to contain 66 mol % of 3-hydroxy-5-(phenylsulfonyl)valeric acid, 30 mol % of 3-hydroxy-5-phenylvaleric acid, and total 4 mol % of the others (straight-chained 3-hydroxyalkanoic acid having 4 to 12 carbon atoms and 3-hydroxyalk-5-enoic acid having 10 or 12 carbon atoms), as shown by chemical formula (34).

mol % of 3-hydroxy-5-(phenylsulfanyl)valeric acid, 34 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms), as shown by chemical formula (35).

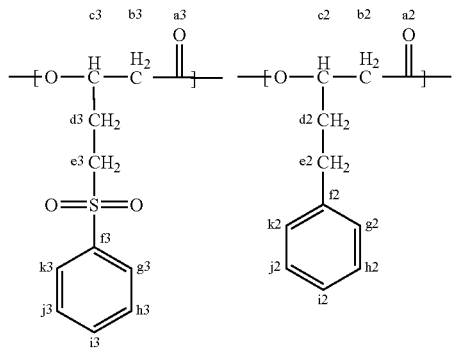

(34)

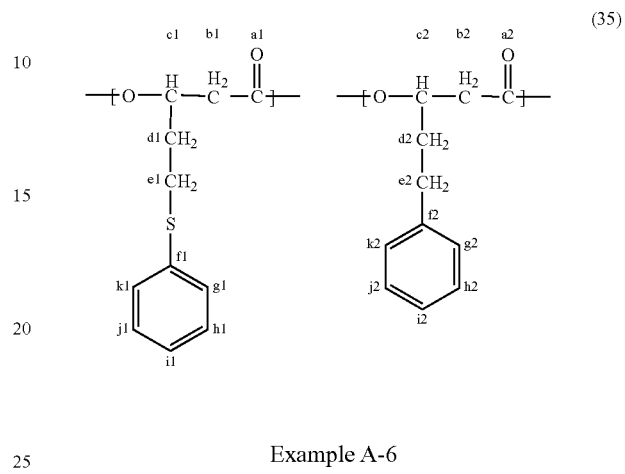

(35)

Example A-5

Each 200 ml of an M9 culture medium containing 0.5% of polypeptone (from NIHON PHARMACEUTICAL CO., LTD.), 0.1% of 5-(phenylsulfanyl)valeric acid, and 2.0 mmol of 5-phenylvaleric acid was charged into 8 shaking flasks of 500 ml volume, sterilized under high temperature and high pressure, cooled, and seeded with *Pseudomonas cichorii* YN2 strain. The cells were shaking-cultured at 30° C. and 125 strokes/minute. Thirty-nine hours later, the cells were collected by centrifugation, washed with cold methanol once, and then dried under vacuum.

The pellet of this dried cell was suspended in 100 ml of chloroform and stirred at 35° C. for 97 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 1,174 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 242,500, and the weight average molecular weight Mw was 615,500.

Figure 18:
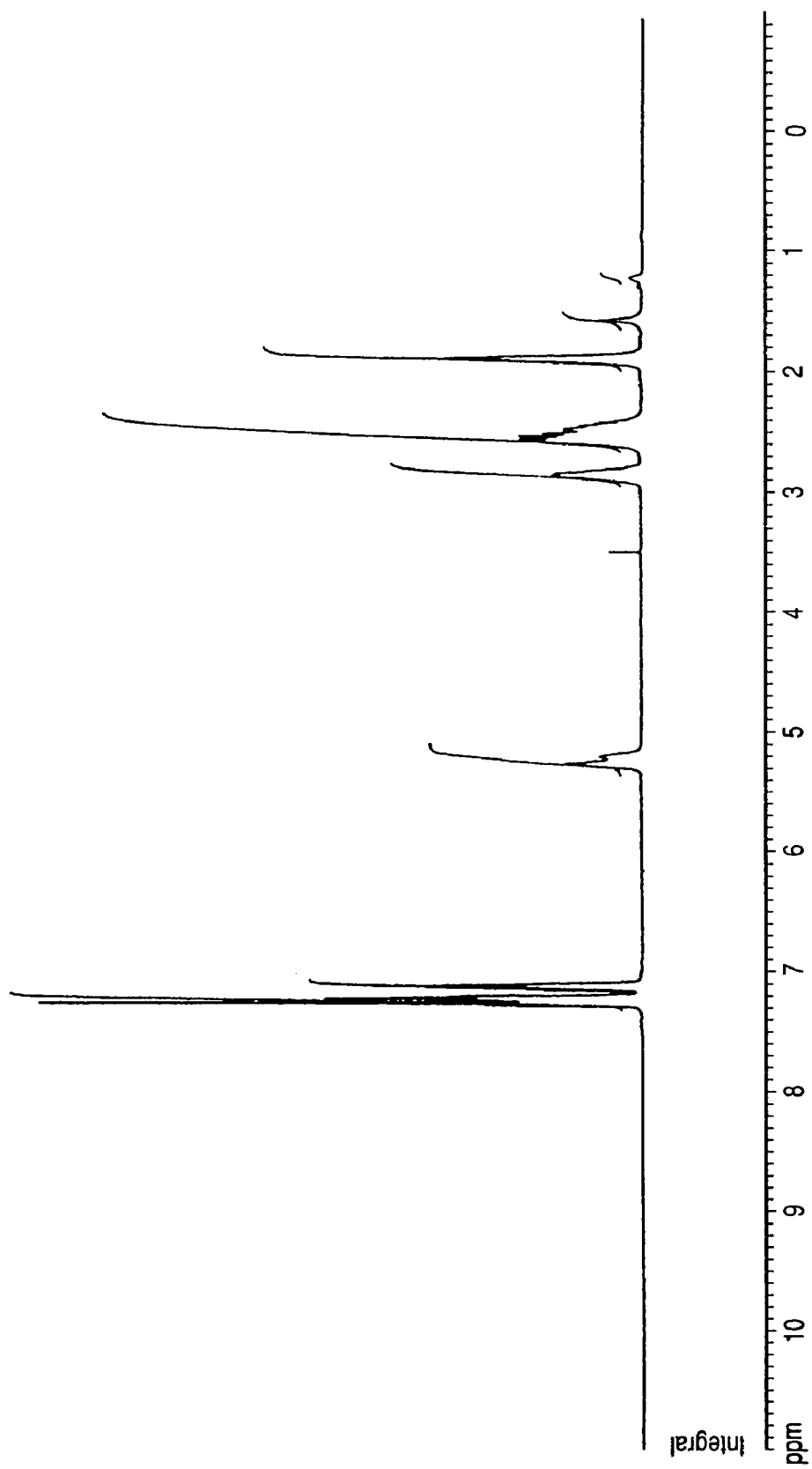
FIG. 18 shows a $^1$H-NMR spectrum of the compound prepared in example A-5.

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 18. As a result, the polyhydroxyalkanoate copolymer was found to contain 60

Example A-6

850 mg of a polyhydroxyalkanoate copolymer containing 60 mol % of 3-hydroxy-5-(phenylsulfanyl)valeric acid, 34 mol % of 3-hydroxy-5-phenylvaleric acid, and total 6 mol % of the others (straight-chained 3-hydroxyalkanoic acid having 4 to 12 carbon atoms and 3-hydroxyalk-5-enoic acid having 10 or 12 carbon atoms) as monomer units was added to a 300 ml round bottomed flask, and then 60 ml of dichloromethane was added and dissolved. The mixture was placed in an ice bath, and 9.0 ml of acetic acid and 2,127 mg of 18-crown-6-ether were added followed by stirring. Next, 1,696 mg of potassium permanganate was gradually added in an ice bath followed by stirring at room temperature for 20 hours. After the reaction was completed, 50 ml of water and 3,000 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 951 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 73,400, and the weight average molecular weight Mw was 194,000.

Figure 19:
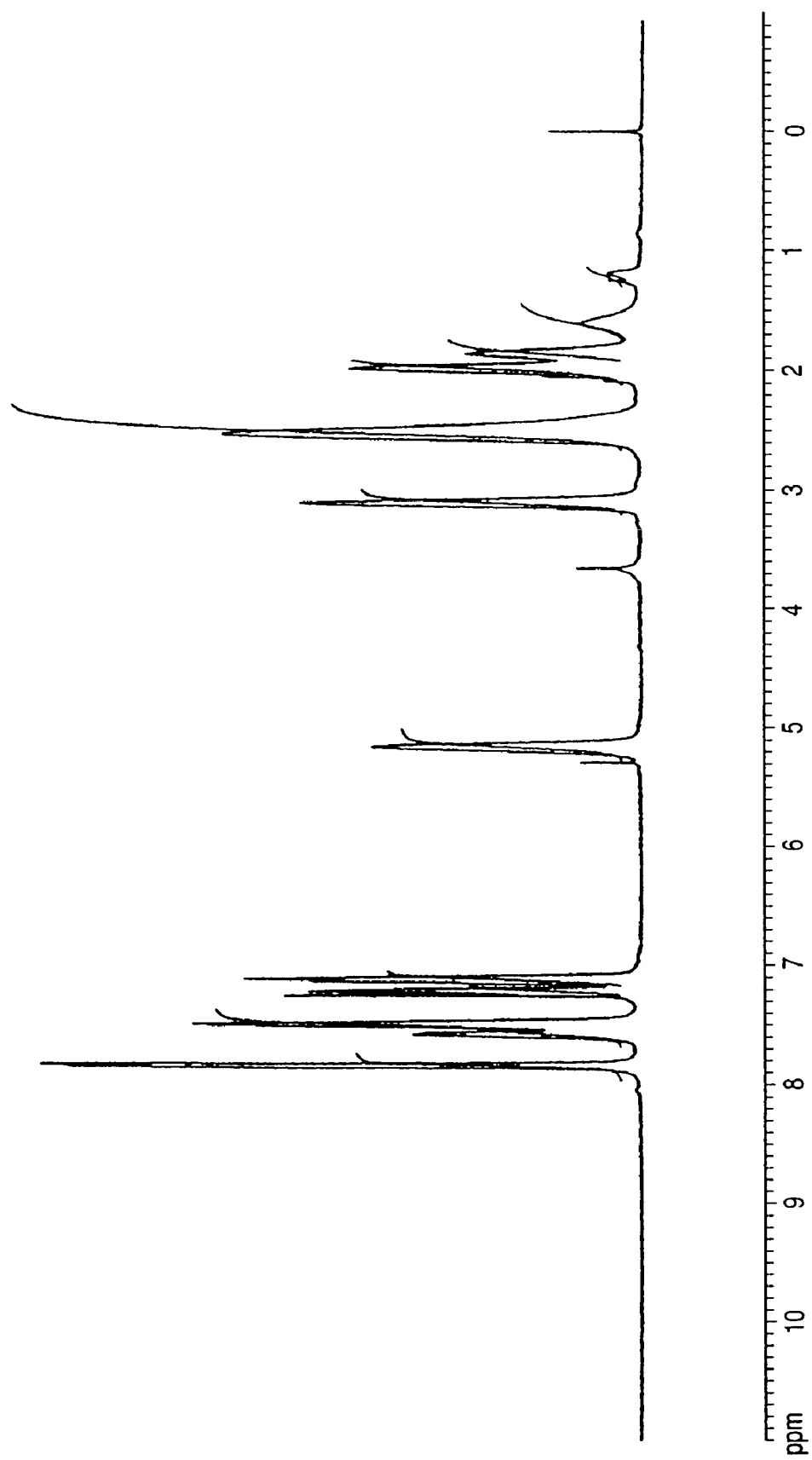
FIG. 19 shows a $^1$H-NMR spectrum of the compound prepared in example A-6.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 19. As a result, the polyhydroxyalkanoate copolymer was found to contain 66 mol % of 3-hydroxy-5-(phenylsulfonyl)valeric acid, 30 mol % of 3-hydroxy-5-phenylvaleric acid, and total 4 mol % of the others (straight-chained 3-hydroxyalkanoic acid having 4 to 12 carbon atoms and 3-hydroxyalk-5-enoic acid having 10 or 12 carbon atoms), as shown by chemical formula (36).

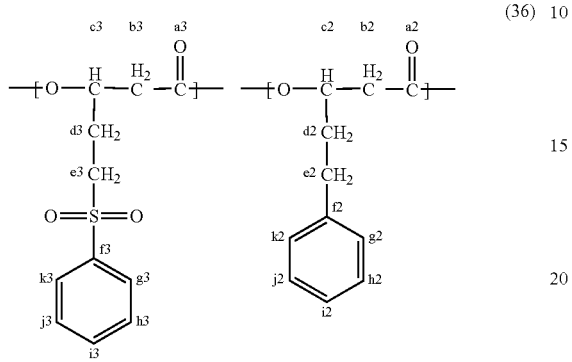

(36)

Example A-7

Each 200 ml of an M9 culture medium containing 0.5% of polypeptone (from NIHON PHARMACEUTICAL CO., LTD.), 0.1% of 5-(phenylsulfanyl)valeric acid, and 6.0 mmol of 5-phenylvaleric acid was charged into 8 shaking flasks of 500 ml volume, sterilized under high temperature and high pressure, cooled, and seeded with *Pseudomonas cichorii* YN2 strain. The cells were shaking-cultured at 30° C. and 125 strokes/minute. Forty-seven hours later, the cells were collected by centrifugation, washed with cold methanol once, and then dried under vacuum.

The pellet of this dried cell was suspended in 100 ml of chloroform and stirred at 35° C. for 97 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed and found to be 633 mg.

The average molecular weight of the resultant PHA was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 84,000, and the weight average molecular weight Mw was 248,800.

Figure 20:
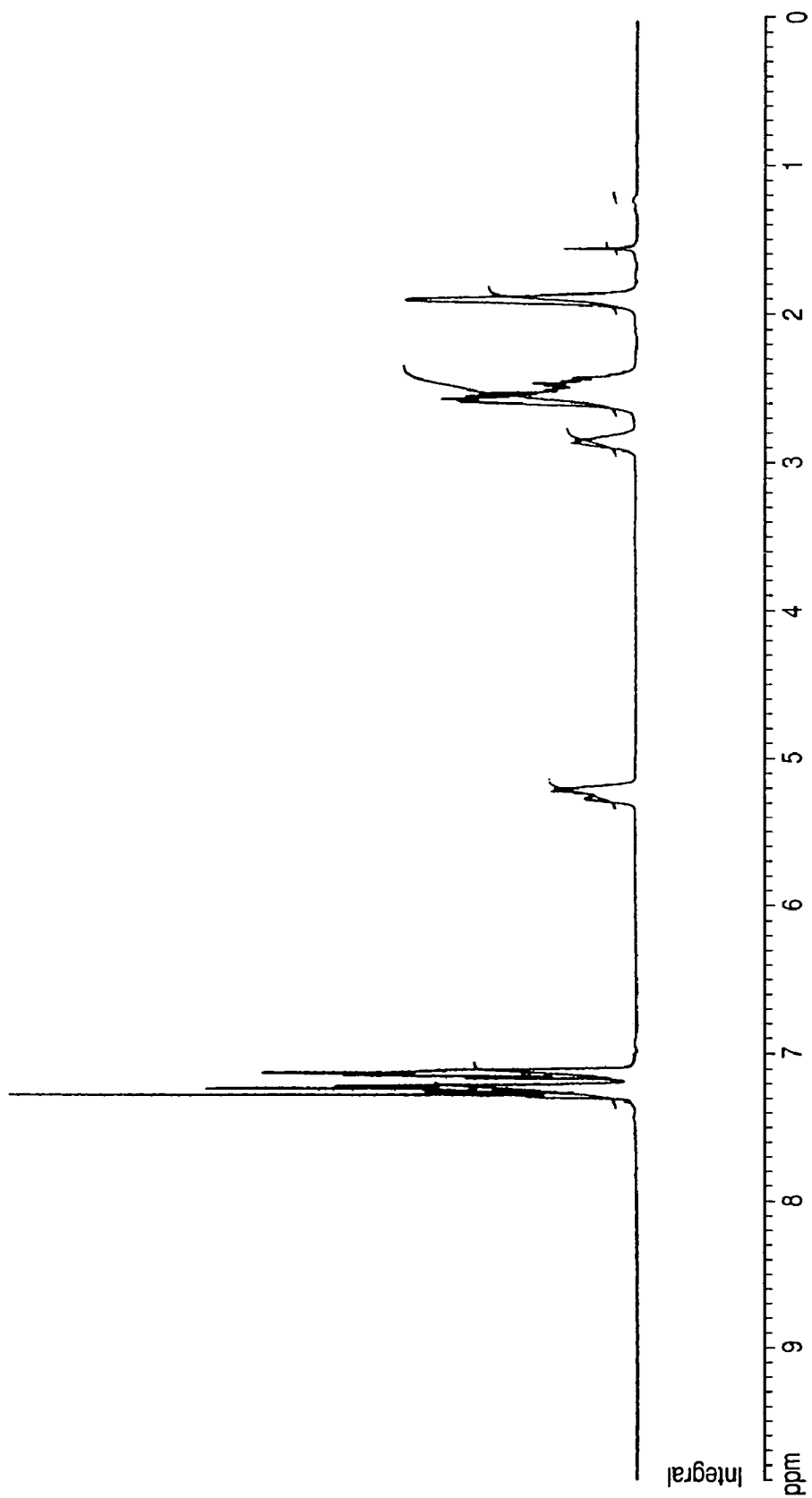
FIG. 20 shows a $^1$H-NMR spectrum of the compound prepared in example A-7.

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 20. As a result, the polyhydroxyalkanoate copolymer was found to contain 38 mol % of 3-hydroxy-5-(phenylsulfanyl)valeric acid, 60 mol % of 3-hydroxy-5-phenylvaleric acid, and total 2 mol % of the others (straight-chained 3-hydroxyalkanoic acid having 4 to 12 carbon atoms and 3-hydroxyalk-5-enoic acid having 10 or 12 carbon atoms), as shown by chemical formula (37).

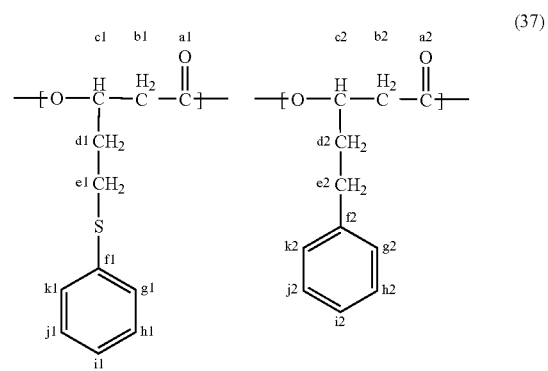

(37)

Example A-8

505 mg of a polyhydroxyalkanoate copolymer containing 38 mol % of 3-hydroxy-5-(phenylsulfanyl)valeric acid, 60 mol % of 3-hydroxy-5-phenylvaleric acid, and total 3 mol % of the others (straight-chained 3-hydroxyalkanoic acid having 4 to 12 carbon atoms and 3-hydroxyalk-5-enoic acid having 10 or 12 carbon atoms) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 550 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 36,200, and the weight average molecular weight Mw was 82,500.

Figure 21:
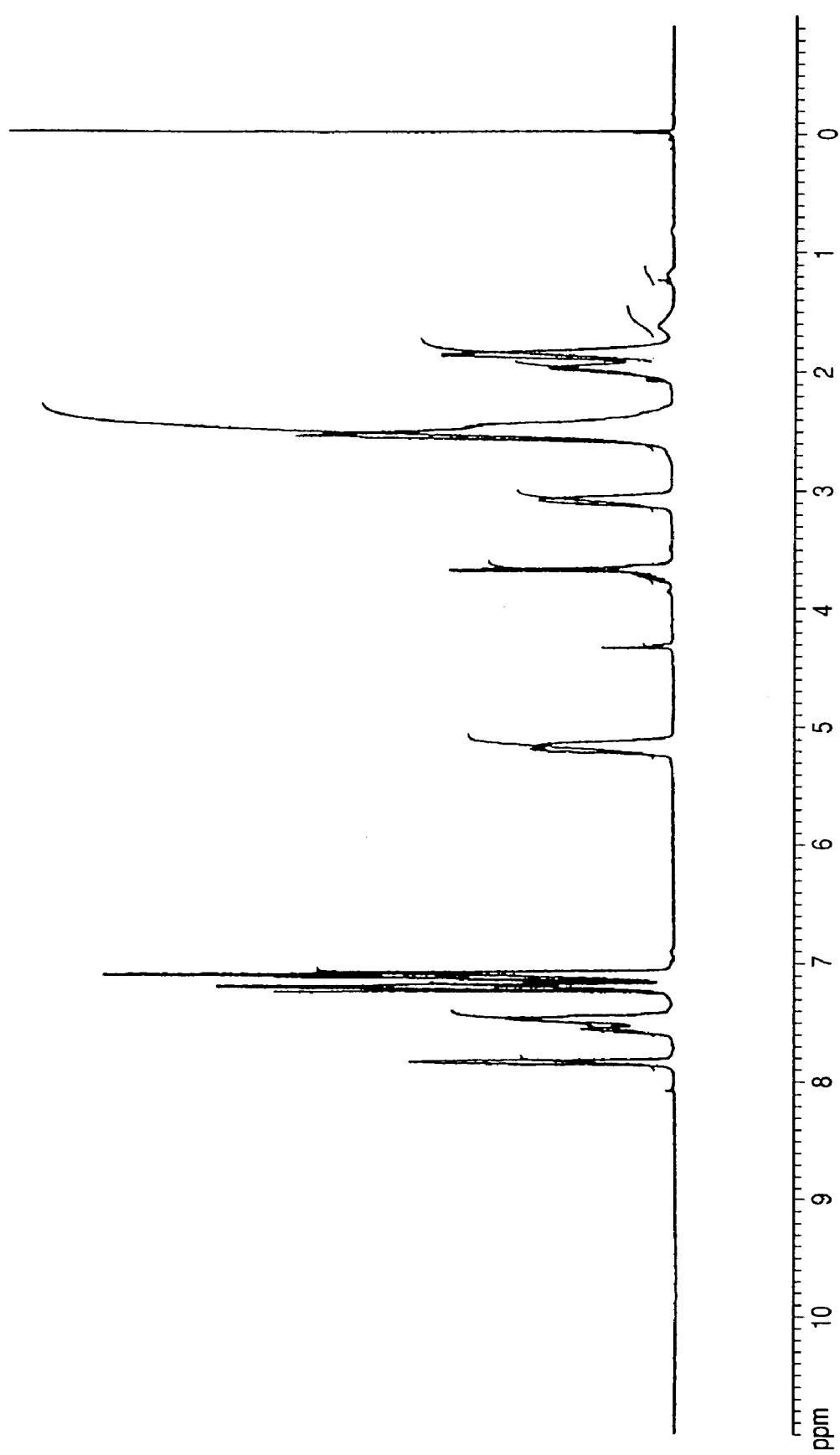
FIG. 21 shows a $^1$H-NMR spectrum of the compound prepared in example A-8.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). The $^1$H-NMR spectrum is shown in FIG. 21. As a result, the polyhydroxyalkanoate copolymer was found to contain 37 mol % of 3-hydroxy-5-(phenylsulfonyl)valeric acid, 62 mol % of 3-hydroxy-5-phenylvaleric acid, and total 1 mol % of the others (straight-chained 3-hydroxyalkanoic acid having 4 to 12 carbon atoms and 3-hydroxyalk-5-enoic acid having 10 or 12 carbon atoms), as shown by chemical formula (38).

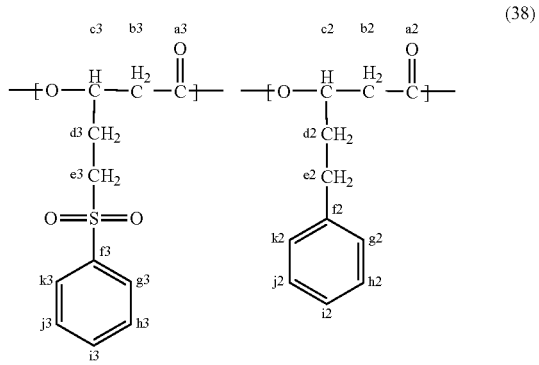

(38)

Example A-9

1,000 ml of an M9 culture medium containing 0.5% of polypeptone (from NIHON PHARMACEUTICAL CO., LTD.), 1 mM of 5-(phenylsulfanyl)valeric acid, and 6 mM of 5-phenoxyvaleric acid was charged into a 2,000 ml shaking flask, sterilized under high temperature and high pressure, cooled, and seeded with *Pseudomonas cichorii* YN2 strain. The cells were shaking-cultured at 30° C. and 100 strokes/minute. Forty hours later, the cells were collected by centrifugation, washed with cold methanol once, and then dried under vacuum.

The pellet of this dried cell was suspended in chloroform and stirred at 35° C. for 16 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 9.

TABLE 9

| CDW (mg/L) | PDW (mg/L) | P/C (%) | Mn (×10⁴) | Mw (×10⁴) | Mw/Mn |
|---|---|---|---|---|---|
| 650 | 190 | 29.2 | 5.8 | 13.0 | 2.2 |

CDW: dry weight of cells
PDW: dry weight of polymer
P/C: dry weight of polymer/dry weight of cells
Mn: number average molecular weight
Mw: weight average molecular weight
Mw/Mn: molecular weight distribution
(The definitions of the above CDW, PDW, P/C, Mn, Mw, and Mw/Mn are the same also in the following tables.)

The structure of the resultant PHA was determined by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature). As a result, the polyhydroxyalkanoate copolymer was found to contain 25 mol % of a 3-hydroxy-5-(phenylsulfanyl)valeric acid unit, 69 mol % of a 3-hydroxy-5-phenoxyvaleric acid unit, and total 6 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (39).

This step was carried out for 3 batches, and the resultant polyhydroxyalkanoate copolymer was used in the next Example.

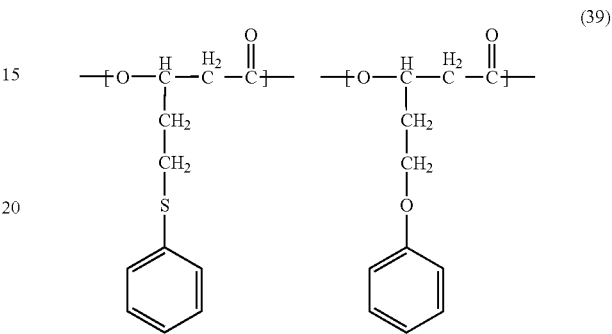

(39)

Example A-10

505 mg of a polyhydroxyalkanoate copolymer containing 25 mol % of a 3-hydroxy-5-(phenylsulfanyl)valeric acid unit, 69 mol % of a 3-hydroxy-5-phenoxyvaleric acid unit, and total 6 mol % of the others (a straight-chained 3-hydroxyalkanoic acid unit having 4 to 12 carbon atoms and a 3-hydroxyalk-5-enoic acid unit having 10 or 12 carbon atoms) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 525 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 23,500, and the weight average molecular weight Mw was 50,500.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature). As a result, the polyhydroxyalkanoate copolymer was found to contain 27 mol % of 3-hydroxy-5-(phenylsulfonyl)valeric acid, 69 mol % of 3-hydroxy-5-phenylvaleric acid, and total 4 mol % of the others (straight-chained 3-hydroxyalkanoic acid having 4 to 12 carbon atoms and 3-hydroxyalk-5-enoic acid having 10 or 12 carbon atoms), as shown by chemical formula (40).

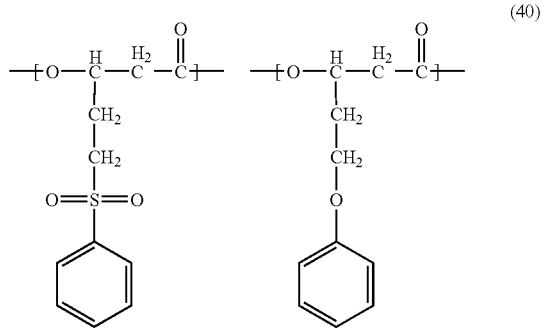

Example A-11

1,000 ml of an M9 culture medium containing 0.5% of polypeptone (from NIHON PHARMACEUTICAL CO., LTD.), 1.28 g of 5-(phenylsulfanyl)valeric acid, and 0.21 g of 5-(4-vinylphenyl)valeric acid was charged into a 2,000 ml shaking flask, sterilized under high temperature and high pressure, cooled, and seeded with *Pseudomonas cichorii* YN2 strain. The cells were shaking-cultured at 30° C. and 100 strokes/minute. Thirty-eight hours later, the cells were collected by centrifugation, washed with cold methanol once, and then dried under vacuum.

The pellet of this dried cell was suspended in chloroform and stirred at 35° C. for 17 hours to extract PHA. After filtering by a membrane filter of the pore size of 0.45 µm, the extract was concentrated by a rotary evaporator. The solution was redissolved in acetone, and the undissolved portion was filtered off. Then, after the filtrate was concentrated by a rotary evaporator, the concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 10.

TABLE 10

| CDW (mg/L) | PDW (mg/L) | P/C (%) | Mn (×10$^4$) | Mw (×10$^4$) | Mw/Mn |
|---|---|---|---|---|---|
| 917 | 369 | 40.2 | 4.8 | 12.3 | 2.5 |

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/ CDCl$_3$; measurement temperature: room temperature). As a result, the polyhydroxyalkanoate copolymer was found to contain 70 mol % of a 3-hydroxy-5-(phenylsulfanyl)valeric acid unit, 20 mol % of a 3-hydroxy-5-(4-vinylphenyl)valeric acid unit, and total 10 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (41).

This step was carried out for 2 batches, and the resultant polyhydroxyalkanoate copolymer was used in the next Example.

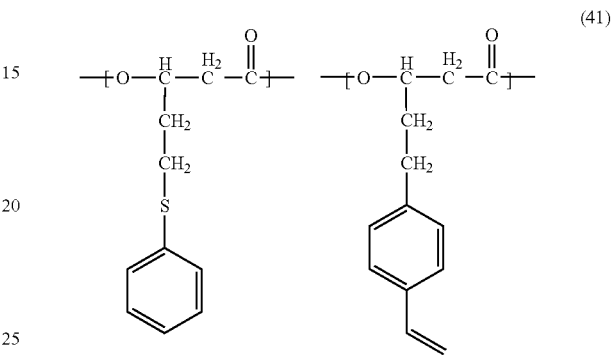

Example A-12

505 mg of a polyhydroxyalkanoate copolymer containing 70 mol % of a 3-hydroxy-5-(phenylsulfanyl)valeric acid unit, 20 mol % of a 3-hydroxy-5-(4-vinylphenyl)valeric acid unit, and total 10 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 590 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 22,300, and the weight average molecular weight Mw was 45,000.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 71 mol % of 3-hydroxy-5-(phenylsulfonyl)valeric acid, 21 mol % of 3-hydroxy-5-(4-carboxyphenyl)valeric acid, and total 8 mol % of the others (straight-chained 3-hydroxyalkanoic acid having 4 to 12 carbon atoms and 3-hydroxyalk-5-enoic acid having 10 or 12 carbon atoms), as shown by chemical formula (42).

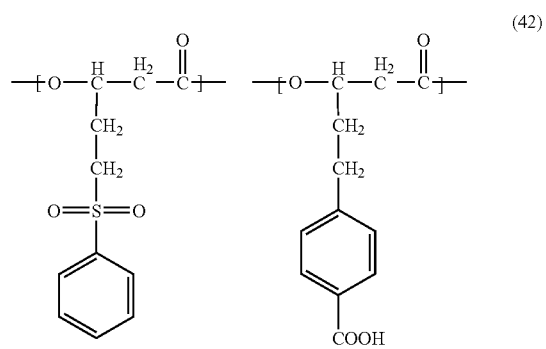

(42)

Example A-13

200 ml of an M9 culture medium containing 0.5% of polypeptone (from NIHON PHARMACEUTICAL CO., LTD.), 1 mM of 5-(phenylsulfanyl)valeric acid, and 6 mM of 4-cyclohexylbutyric acid was charged into a 500 ml shaking flask, sterilized under high temperature and high pressure, cooled, and seeded with *Pseudomonas cichorii* YN2 strain. The cells were shaking-cultured at 30° C. and 125 strokes/minute. Forty hours later, the cells were collected by centrifugation, washed with cold methanol once, and then dried under vacuum.

The pellet of this dried cell was suspended in chloroform and stirred at 35° C. for 16 hours to extract PHA. After filtering by a membrane filter of the pore size of 0.45 µm, the extract was concentrated by a rotary evaporator. The concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 11.

TABLE 11

| CDW (mg/L) | PDW (mg/L) | P/C (%) | Mn (×10$^4$) | Mw (×10$^4$) | Mw/Mn |
|---|---|---|---|---|---|
| 790 | 210 | 26.6 | 5.5 | 12.8 | 2.3 |

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 66 mol % of a 3-hydroxy-5-(phenylsulfanyl)valeric acid unit, and total 34 mol % of a 3-hydroxy-4-cyclohexylbutyric acid unit and the others (straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (43).

This step was carried out for 3 batches, and the resultant polyhydroxyalkanoate copolymer was used in the next Example.

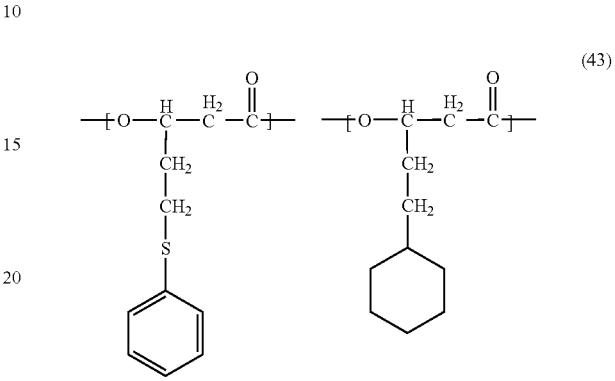

(43)

Example A-14

505 mg of a polyhydroxyalkanoate copolymer containing 66 mol % of a 3-hydroxy-5-(phenylsulfanyl)valeric acid unit, a 3-hydroxy-4-cyclohexylbutyric acid unit, and total 34 mol % of the others (straight-chained 3-hydroxyalkanoic acid unit having 4 to 12 carbon atoms and a 3-hydroxyalk-5-enoic acid unit having 10 or 12 carbon atoms, not shown in the following chemical formula) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 545 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 27,000, and the weight average molecular weight Mw was 62,000.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 68 mol % of 3-hydroxy-5-(phenylsulfonyl)valeric acid, and total 32 mol % of a 3-hydroxy-4-cyclohexylbutyric acid unit and the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (44).

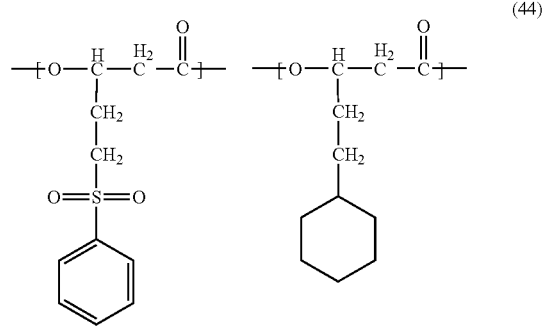

(44)

Example A-15

200 ml of an M9 culture medium containing 0.5% of polypeptone (from NIHON PHARMACEUTICAL CO., LTD.), 1 mM of 5-(phenylsulfanyl)valeric acid, and 6 mM of 5-benzoylvaleric acid was charged into a 500 ml shaking flask, sterilized under high temperature and high pressure, cooled, and seeded with *Pseudomonas cichorii* YN2 strain. The cells were shaking-cultured at 30° C. and 125 strokes/minute. Forty hours later, the cells were collected by centrifugation, washed with cold methanol once, and then dried under vacuum.

The pellet of this dried cell was suspended in chloroform and stirred at 35° C. for 16 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 12.

TABLE 12

| CDW (mg/L) | PDW (mg/L) | P/C (%) | Mn (×10$^4$) | Mw (×10$^4$) | Mw/Mn |
|---|---|---|---|---|---|
| 750 | 200 | 26.7 | 10.8 | 34.5 | 3.2 |

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 28 mol % of a 3-hydroxy-5-(phenylsulfanyl)valeric acid unit, 53 mol % of a 3-hydroxy-5-benzoylvaleric acid unit, and total 19 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (45).

This step was carried out for 3 batches, and the resultant polyhydroxyalkanoate copolymer was used in the next Example.

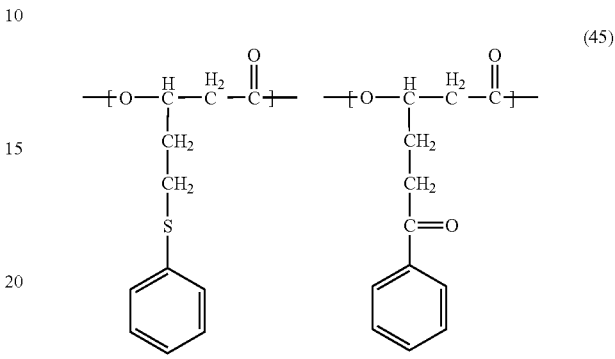

(45)

Example A-16

505 mg of a polyhydroxyalkanoate copolymer containing 28 mol % of a 3-hydroxy-5-(phenylsulfanyl)valeric acid unit, 53 mol % of a 3-hydroxy-5-benzoylvaleric acid unit, and total 19 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 515 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 41,000, and the weight average molecular weight Mw was 115,000.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 30 mol % of 3-hydroxy-5-(phenylsulfonyl)valeric acid, 54 mol % of a 3-hydroxy-5-benzoylvaleric acid unit, and total 16 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (46).

3-hydroxyalkanoic acid unit having 4 to 12 carbon atoms and a 3-hydroxyalk-5-enoic acid unit having 10 or 12 carbon atoms, not shown in the following chemical formula), as shown by chemical formula (47).

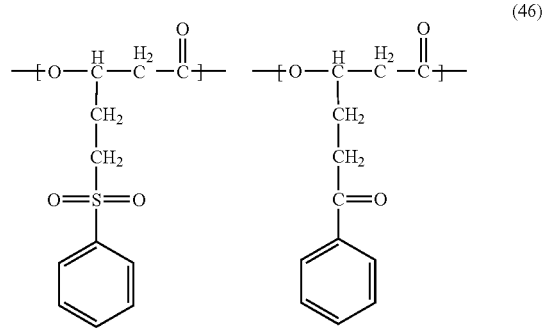

(46)

Example A-17

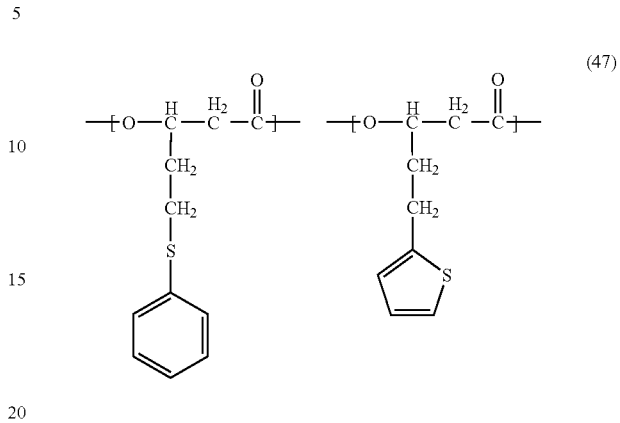

(47)

Example A-18

200 ml of an M9 culture medium containing 0.5% of polypeptone (from NIHON PHARMACEUTICAL CO., LTD.), 1 mM of 5-(phenylsulfanyl)valeric acid, and 6 mM of 5-(2-thienyl)valeric acid was charged into a 500 ml shaking flask, sterilized under high temperature and high pressure, cooled, and seeded with *Pseudomonas cichorii* YN2 strain. The cells were shaking-cultured at 30° C. and 125 strokes/minute. Forty hours later, the cells were collected by centrifugation, washed with cold methanol once, and then dried under vacuum.

The pellet of this dried cell was suspended in chloroform and stirred at 35° C. for 16 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 13.

TABLE 13

| CDW (mg/L) | PDW (mg/L) | P/C (%) | Mn (×10⁴) | Mw (×10⁴) | Mw/Mn |
|---|---|---|---|---|---|
| 1,100 | 540 | 49.1 | 8.0 | 19.6 | 2.5 |

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 16 mol % of a 3-hydroxy-5-(phenylsulfanyl)valeric acid unit, 80 mol % of a 3-hydroxy-5-(2-thienyl)valeric acid unit, and total 4 mol % of the others (a straight-chained 505 mg of a polyhydroxyalkanoate copolymer containing 16 mol % of a 3-hydroxy-5-(phenylsulfanyl)valeric acid unit, 80 mol % of a 3-hydroxy-5-(2-thienyl)valeric acid unit, and total 4 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 520 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 37,300, and the weight average molecular weight Mw was 78,500.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 15 mol % of 3-hydroxy-5-(phenylsulfonyl)valeric acid, 82 mol % of a 3-hydroxy-5-(2-thienyl)valeric acid unit, and total 3 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (48).

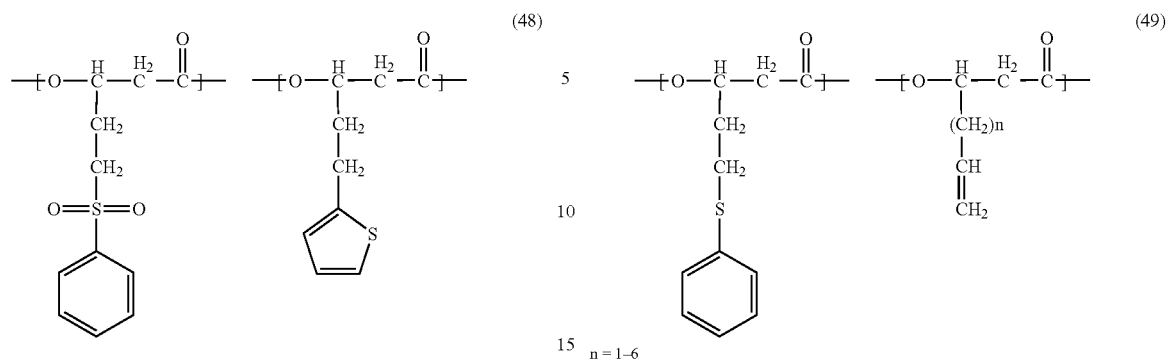

n = 1-6

Example A-19

1,000 ml of an M9 culture medium containing 0.5% of polypeptone (from NIHON PHARMACEUTICAL CO., LTD.), 1.0 g of 5-(phenylsulfanyl)valeric acid, and 2 mM of 10-undecenoic acid was charged into a 2,000 ml shaking flask, sterilized under high temperature and high pressure, cooled, and seeded with *Pseudomonas cichorii* YN2 strain. The cells were shaking-cultured at 30° C. and 100 strokes/minute. Thirty-eight hours later, the cells were collected by centrifugation, washed with cold methanol once, and then dried under vacuum.

The pellet of this dried cell was suspended in chloroform and stirred at 35° C. for 25 hours to extract PHA. After filtering by a membrane filter of the pore size of 0.45 μm, the extract was concentrated by a rotary evaporator. The concentrated solution was added to cold methanol, and PHA was reprecipitated. Only the precipitate was collected and dried under vacuum. The resultant PHA was weighed.

The average molecular weight of the resultant PHA was evaluated by gel permeation chromatography (GPC; Tosoh HLC-8220, column: Tosoh TSK-GEL SuperHM-H; solvent; chloroform; polystyrene equivalent).

The dry weight of cells obtained in the above step, the dry weight of the collected polymer, the weight ratio of the collected polymer to dried cells, and the number average molecular weight, the weight average molecular weight, and the molecular weight distribution of the resultant polymer are shown together in Table 14.

TABLE 14

| CDW (mg/L) | PDW (mg/L) | P/C (%) | Mn (×10$^4$) | Mw (×10$^4$) | Mw/Mn |
|---|---|---|---|---|---|
| 1,410 | 640 | 45.4 | 15.0 | 43.0 | 2.9 |

The structure of the resultant PHA was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 78 mol % of a 3-hydroxy-5-(phenylsulfanyl)valeric acid unit, 19 mol % of a straight-chained 3-hydroxyalkenoic acid unit with an unsaturated terminal, and total 3 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (49).

Example A-20

505 mg of a polyhydroxyalkanoate copolymer containing 78 mol % of a 3-hydroxy-5-(phenylsulfanyl)valeric acid unit, 19 mol % of a straight-chained 3-hydroxyalkenoic acid unit with an unsaturated terminal, and total 3 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula) as monomer units was added to a 300 ml round bottomed flask, and then 30 ml of dichloromethane was added and dissolved. The mixture was placed in an ice bath, and 4 ml of acetic acid and 779 mg of 18-crown-6-ether were added followed by stirring. Next, 618 mg of potassium permanganate was gradually added in an ice bath followed by stirring at room temperature for 20 hours. After the reaction was completed, 50 ml of water and 1,500 mg of sodium bisulfite were added. Then, the solution was made to be pH 1 by adding 1.0 mol/L (1.0N) hydrochloric acid. After dichloromethane in the mixed solution was distilled off by an evaporator, the polymer in the solution was collected. The polymer was washed with 100 ml of methanol, and then three portions of 100 ml of pure water followed by collecting the polymer. The thus obtained polymer was purified by dialysis using chloroform. After purification, 585 mg of the desired polyhydroxyalkanoate was obtained by drying under a reduced pressure.

The average molecular weight of the resultant polyhydroxyalkanoate was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 63,500, and the weight average molecular weight Mw was 163,000.

In order to determine the construction of the resultant polyhydroxyalkanoate, analysis was performed by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature). As a result, the polyhydroxyalkanoate copolymer was found to contain 77 mol % of 3-hydroxy-5-(phenylsulfonyl)valeric acid, 21 mol % of a 3-hydroxy-o-carboxyalkanoic acid unit, and total 2 mol % of the others (a straight-chained 3-hydroxyalkanoic acid unit having 4 to 12 carbon atoms and a 3-hydroxyalk-5-enoic acid unit having 10 or 12 carbon atoms, not shown in the following chemical formula), as shown by chemical formula (50).

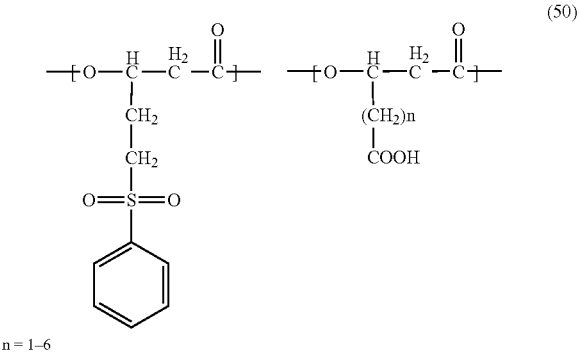

(50)

n = 1–6

Molded Product of Resin Composition

PHAA-1 to PHAA-5 of the above Preparation Examples A-1 to A-4 and Comparative Preparation Example A-1, or a resin composition containing thereof were molded to evaluate degradability and performance as a molded article as follows (Examples B-1 to B-4, Comparative Examples B-1 and B-2).

Example B-1

Foamed extruded sheets were molded by using resin compositions PHAA-1 to PHAA-4 described in Preparation Examples A-1 to A-4 and subjected to a second molding to produce instant noodle containers 1 to 4. Meanwhile, the resin compositions PHAA-1 to PHAA-4 described in Preparation Examples A-1 to A-4 and a polystyrene polymer (Styron 685, from Asahi Kasei Corporation) were blended in a mass ratio of 75:25 to produce instant noodle containers 5 to 8 in the same manner. They were also blended in a mass ratio of 51:49 in the same manner to produce instant noodle containers 9 to 12 in the same manner. Each mass was 3.0 g per container.

Comparative Example B-1

A foamed extruded sheet was molded by using the resin composition PHAA-5 described in Comparative Preparation Example A-1 and subjected to a second molding to produce an instant noodle container 9. Meanwhile, the resin composition PHAA-5 described in Comparative Preparation Example A-1 and a polystyrene polymer (Styron 685, from Asahi Kasei Corporation) were blended in mass ratios of 75:25 and 51:49 to produce instant noodle containers 14 and 15 in the same manner. Further, using only the above polystyrene polymer, an instant noodle container 16 was produced in the same manner. Each mass was 3.0 g per container.

Example B-2

Using resin compositions PHAA-1 to PHAA-4 described in Preparation Examples A-1 to A-4, drink containers 1 to 4 were produced by injection blow molding. Meanwhile, the resin compositions PHAA-1 to PHAA-4 described in Preparation Examples A-1 to A-4 and a lactone polymer (Polycaprolactone, from DAICEL CHEMICAL INDUSTRIES, LTD.) were blended in a mass ratio of 75:25 to produce drink containers 5 to 8 in the same manner. They were also blended in a mass ratio of 51:49 in the same manner to produce drink containers 9 to 12 in the same manner.

Each mass was 3.0 g per container.

Comparative Example B-2

Using a resin composition PHAA-5 described in Comparative Preparation Example A-1, a drink container 9 was produced by injection blow molding. Meanwhile, the resin composition PHAA-5 described in Comparative Preparation Example A-1 and a lactone polymer (Polycaprolactone, from DAICEL CHEMICAL INDUSTRIES, LTD.) were blended in mass ratios of 75:25 and 51:49 to produce drink containers 14 and 15 in the same manner. Further, using only the above lactone polymer, a drink container 16 was produced in the same manner.

Each mass was 3.0 g per container.

Example B-3

With respect to an instant noodle container described in Example B-1 or Comparative Example B-1, the following evaluation items were tested in order to compare and evaluate the quality as an instant noodle container. The results are shown in Table 15.

A: good, B: usable, C: unusable, -: untested

Biodegradability: It was checked visually whether or not to be almost invisible after buried in the soil for 6 months. It should be noted that B in the table indicates that resin residues were slightly recognized during the above period, and C indicates that there was not substantial biodegradability during the above period.

Quality as instant noodle container: Hardness, brittleness, and fracture/leakage were evaluated at 25° C. (assuming the storage time) and 100° C. (assuming the time to pour hot water).

Tg and Tm: The measurements were performed by a differential scanning calorimeter (DSC; from PerkinElmer, Inc., Pyris 1, temperature elevation: 20° C./minute)

TABLE 15

|  |  | 25° C. | | | 100° C. | | | | |
| --- | --- | --- | --- | --- | --- | --- | --- | --- | --- |
| Container | Biodegradability | Hardness | Brittleness | Fracture/leakage | Hardness | Brittleness | Fracture/leakage | Tg | Tm |
| 1 | A | A | A | A | A | A | A | 91 | 195 |
| 2 | A | A | A | A | A | A | A | 67 | 183 |
| 3 | A | A | A | A | A | A | A | 55 | 172 |
| 4 | A | A | A | A | A | A | A | 57 | 170 |
| 5 | A | A | A | A | A | A | A | — | — |
| 6 | A | A | A | A | A | A | A | — | — |
| 7 | A | A | A | A | A | A | A | — | — |
| 8 | A | A | A | A | A | A | A | — | — |
| 9 | B | A | A | A | A | A | A | — | — |

TABLE 15-continued

| | | 25° C. | | | 100° C. | | | | |
|---|---|---|---|---|---|---|---|---|---|
| Container | Biodegradability | Hardness | Brittleness | Fracture/ leakage | Hardness | Brittleness | Fracture/ leakage | Tg | Tm |
| 10 | B | A | A | A | A | A | A | — | — |
| 11 | B | A | A | A | A | A | A | — | — |
| 12 | B | A | A | A | A | A | A | — | — |
| 13 | A | C | — | — | C | — | — | 19 | 158 |
| 14 | A | B | A | B | C | — | — | — | — |
| 15 | B | B | A | B | C | — | — | — | — |
| 16 | C | A | A | A | A | A | A | 93 | 210 |

Example B-4

With respect to the drink container described in Example B-2 or Comparative Example B-2, the following evaluation items were tested in order to compare and evaluate the quality as a drink container. The results are shown in Table 16.

A: good, B: usable, C: unusable, -: untested

Biodegradability: It was checked visually whether or not to be almost invisible after buried in the soil for 6 months. It should be noted that B in the table indicates that resin residues were slightly recognized during the above period, and C indicates that there was not substantial biodegradability during the above period.

Quality as instant noodle container: Hardness, brittleness, and fracture/leakage were evaluated at 25° C. (assuming the storage time) and 100° C. (assuming the time of heat sterilization).

Tg and Tm: The measurement was performed by a differential scanning calorimeter (DSC; from PerkinElmer, Inc., Pyris 1, temperature elevation: 20° C./minute).

Example C-1

80 g of polylactic acid (Lacty (trade name), from Shimadzu Corporation, melt viscosity at 195° C. 20,000 Pa.s (=200,000 poise), weight average molecular weight 200,000) and 120 g of PHA of Preparation Example A-1 (PHAA-1) were blended, charged in an injection molding machine, and melt-kneaded at 195-230° C. for molding. The thus obtained polymer blend was referred to as PHAC-1 and used as a binder resin.

Example C-2

80 g of polylactic acid (Lacty (trade name), from Shimadzu Corporation, melt viscosity at 195° C. 20,000 Pa.s (=200,000 poise), weight average molecular weight 200,000) and 120 g of PHA of Preparation Example A-2 (PHAA-2) were blended, charged in an injection molding machine, and melt-

TABLE 16

| | | 25° C. | | | 100° C. | | | | |
|---|---|---|---|---|---|---|---|---|---|
| Container | Biodegradability | Hardness | Brittleness | Fracture/ leakage | Hardness | Brittleness | Fracture/ leakage | Tg | Tm |
| 1 | A | A | A | A | A | A | A | 91 | 195 |
| 2 | A | A | A | A | A | A | A | 67 | 183 |
| 3 | A | A | A | A | A | A | A | 55 | 172 |
| 4 | A | A | A | A | A | A | A | 57 | 170 |
| 5 | A | A | A | A | A | A | A | — | — |
| 6 | A | A | A | A | A | A | A | — | — |
| 7 | A | A | A | A | A | A | A | — | — |
| 8 | A | A | A | A | A | A | A | — | — |
| 9 | A | A | A | A | A | A | A | — | — |
| 10 | A | A | A | A | A | A | A | — | — |
| 11 | A | A | A | A | A | A | A | — | — |
| 12 | A | A | A | A | A | A | A | — | — |
| 13 | A | C | — | — | C | — | — | 19 | 158 |
| 14 | A | C | — | — | C | — | — | — | — |
| 15 | A | C | — | — | C | — | — | — | — |
| 16 | A | C | — | — | C | — | — | — | 60 |

Besides the above Examples, the molded articles of the present invention was experimented under conditions of 40° C. and 140° C., and it was found that the molded articles do not have any problem in hardness, brittleness, and fracture/leakage, being excellent in biodegradability.

[Binder Resin]

Next, the polymer blends which are used as binder resins of the present invention are shown as follows (Examples C-1 to C-4).

kneaded at 195-230° C. for molding. The thus obtained polymer blend was referred to as PHAC-2 and used as a binder resin.

(Example C-3)

80 g of polylactic acid (Lacty (trade name), from Shimadzu Corporation, melt viscosity at 195° C. 20,000 Pa.s (=200,000 poise), weight average molecular weight 200,000) and 120 g of PHA of Preparation Example A-3 (PHAA-3) were blended, charged in an injection molding machine, and melt-kneaded at 195-230° C. for molding. The thus obtained polymer blend was referred to as PHAC-3 and used as a binder resin.

Example C-4

80 g of polylactic acid (Lacty (trade name), from Shimadzu Corporation, melt viscosity at 195° C. 20,000 Pa.s (=200,000 poise), weight average molecular weight 200,000) and 120 g of PHA of Preparation Example A-4 (PHAA-4) were blended, charged in an injection molding machine, and melt-kneaded at 195-230° C. for molding. The thus obtained polymer blend was referred to as PHAC-4 and used as a binder resin.

Various toners were produced using the polymer blends of the above Examples C-1 to C-4 and a single PHA polymer (above Preparation Examples A-1 to A-4) and evaluated (Examples D-1 to D-8, Comparative Examples D-1 and D-2

Example D-1

| | |
|---|---|
| PHAA-1 (Preparation Example A-1) | 100 parts by mass |
| Magenta pigment (C.I. Pigment Red 114) | 5 parts by mass |
| Charge controlling agent (from Hoechst AG: NXVP 434) | 2 parts by mass |

The above composition was mixed and melt-kneaded by a biaxial extruder (L/D=30). The resultant kneaded product was cooled, roughly ground by a hammer mill, finely ground by a jet mill, and then classified to obtain magenta coloring particles (1) by a grinding method. For the particle size of the magenta coloring particles (1), the weight average particle size was 8.1 μm and the ratio of fines was 2.9% by number.

As a fluidity improver, 1.5 parts by mass of hydrophobic silica fine powder (BET: 250 m$^2$/g) treated with hexamethyldisilazane were dry-mixed with 100 parts by mass of the magenta coloring particles (1) by a Henshel mixer, whereby a magenta toner (1) of this Example was obtained. In addition, 7 parts by mass of the resultant magenta toner (1) were mixed with 93 parts by mass of a resin-coated magnetic ferrite carrier (average particle size: 45 μm) to prepare a two-component type magenta developer (1) for magnetic brush development.

Examples D-2 to D-8

Magenta toners (2) to (8) of Examples D-2 to D-8 were obtained in the same manner as in Example D-1 except that 100 parts by mass of each of PHAA-2 to PHAA-4 and PHAC-1 to PHAC-4 were used in place of PHAA-1. The properties of the toners were measured in the same manner as in Example D-1, and the results are shown in Table 17. In addition, two-component type magenta developers (2) to (8) were obtained in the same manner as in Example D-1 using the toners, respectively.

Comparative Example D-1

A magenta toner (9) of Comparative Example D-1 was obtained in the same manner as in Example D-1 except that 100 parts by mass of a styrene-butylacrylate copolymer resin (glass transition temperature 70° C.) was used in place of PHAA-1. The properties of the toner were measured in the same manner as in Example D-1, and the results are shown in Table 17. In addition, a two-component type magenta developer (9) of Comparative Example D-1 was obtained in the same manner as in Example D-1 using the toner.

<Evaluation>

For the two-component type magenta developers (1) to (8) obtained in the above Examples D-1 to D-8 and the two-component type magenta developer (9) obtained in Comparative Example D-1, the charge levels of the toners after stirring for 10 and 300 seconds were measured under conditions of normal temperature and normal humidity (25° C., 60% RH) and high temperature and high humidity (30° C., 80% RH) using the previously described method for measuring charge levels. Then, numbers from measurement values of two-component blow-off charge levels were rounded off to one decimal place to make evaluations according to the following criteria. The results are shown together in Table 17.

TABLE 17

Electrification property of magenta toners (1) to (9)

| | | | Particle size distribution | | Electrifiability | | | |
|---|---|---|---|---|---|---|---|---|
| | | | | | Normal temperature and normal humidity (Q/M) | | High temperature and high humidity (Q/M) | |
| Examples | Number of PHA | Toner Number: Red | Weight average particle size (μm) | Ratio of fines (% by number) | Stirring for 10 seconds | Stirring for 300 seconds | Stirring for 10 seconds | Stirring for 300 seconds |
| D-1 | PHAA-1 | 1 | 8.1 | 2.9 | A | E | A | E |
| D-2 | PHAA-2 | 2 | 7.9 | 2.7 | A | E | A | E |
| D-3 | PHAA-3 | 3 | 8.1 | 3.0 | E | E | E | E |
| D-4 | PHAA-4 | 4 | 8.2 | 3.3 | E | E | E | E |
| D-5 | PHAC-1 | 5 | 8.4 | 4.0 | A | E | A | E |
| D-6 | PHAC-2 | 6 | 8.3 | 3.5 | A | E | A | E |

TABLE 17-continued

Electrification property of magenta toners (1) to (9)

| | | | Particle size distribution | | Electrifiability | | | |
|---|---|---|---|---|---|---|---|---|
| | | | | | Normal temperature and normal humidity (Q/M) | | High temperature and high humidity (Q/M) | |
| Examples | Number of PHA | Toner Number: Red | Weight average particle size (μm) | Ratio of fines (% by number) | Stirring for 10 seconds | Stirring for 300 seconds | Stirring for 10 seconds | Stirring for 300 seconds |
| D-7 | PHAC-3 | 7 | 8.4 | 4.3 | E | E | E | E |
| D-8 | PHAC-4 | 8 | 8.7 | 3.9 | E | E | E | E |
| Comparative Example D-1 | — | 9 | 7.0 | 4.9 | E | E | E | E |

<Electrifiability>
E: Excellent (−20 μC/g or lower)
A: Good (−19.9 to −10.0 μC/g)
B: Usable (−9.9 to −5.0 μC/g)
C: Unusable (−4.9 μC/g or higher)

Examples D-9 to D-16

Black toners (1) to (8) of Examples D-9 to D-16 were obtained respectively in the same manner as in Example D-1 except that 100 parts by mass of PHAA-1 to PHAA-4 and PHAC-1 to PHAC-4 were used, and a carbon black (DBP oil absorption 110 ml/100 g) was used in place of the magenta pigment. The properties of the toners were measured in the same manner as in Example D-1, and the results are shown in Table 18. In addition, two-component type black developers (1) to (8) were obtained in the same manner as in Example D-1 using the toners.

Comparative Example D-2

A black toner (9) of Comparative Example D-2 was obtained in the same manner as in Example D-1 except that 100 parts by mass of a styrene-butylacrylate copolymer resin (glass transition temperature 70° C.) was used in place of PHAA-1 and a carbon black (DBP oil absorption 110 ml/100 g) was used in place of the magenta pigment. The properties of the toner were measured in the same manner as in Example D-1, and the results are shown in Table 18. In addition, a two-component type black developer (9) of Comparative Example D-2 was obtained in the same manner as in Example D-1 using the toner.

<Evaluation>

For the two-component type black developer (1) to (8) obtained in the above Examples D-9 to D-16 and the two-component type black developer (9) obtained in Comparative Example D-2, the charge levels of the toners after stirring for 10 and 300 seconds were measured under conditions of normal temperature and normal humidity (25° C., 60% RH) and high temperature and high humidity (30° C., 80% RH) using the previously described method for measuring charge levels. Then, numbers from measurement values of two-component blow-off charge levels were rounded off to one first decimal place to make evaluations according to the following criteria. The results are shown together in Table 18.

TABLE 18

Electrification property of black toners (1) to (9)

| | | | Particle size distribution | | Electrifiability | | | |
|---|---|---|---|---|---|---|---|---|
| | | | | | Normal temperature and normal humidity (Q/M) | | High temperature and high humidity (Q/M) | |
| Examples | Number of PHA | Toner Number: Black | Weight average particle size (μm) | Ratio of fines (% by number) | Stirring for 10 seconds | Stirring for 300 seconds | Stirring for 10 seconds | Stirring for 300 seconds |
| D-9 | PHAA-1 | 1 | 7.3 | 3.2 | A | E | A | E |
| D-10 | PHAA-2 | 2 | 7.7 | 2.9 | A | E | A | E |
| D-11 | PHAA-3 | 3 | 7.3 | 3.1 | E | E | E | E |
| D-12 | PHAA-4 | 4 | 8.0 | 3.5 | E | E | E | E |
| D-13 | PHAC-1 | 5 | 8.1 | 3.3 | A | E | A | E |
| D-14 | PHAC-2 | 6 | 7.9 | 3.9 | A | E | A | E |

TABLE 18-continued

Electrification property of black toners (1) to (9)

|  |  |  | Particle size distribution |  | Electrifiability | | | |
| --- | --- | --- | --- | --- | --- | --- | --- | --- |
|  |  |  |  |  | Normal temperature and normal humidity (Q/M) | | High temperature and high humidity (Q/M) | |
| Examples | Number of PHA | Toner Number: Black | Weight average particle size (μm) | Ratio of fines (% by number) | Stirring for 10 seconds | Stirring for 300 seconds | Stirring for 10 seconds | Stirring for 300 seconds |
| D-15 | PHAC-3 | 7 | 8.2 | 4.1 | E | E | E | E |
| D-16 | PHAC-4 | 8 | 8.3 | 3.7 | E | E | E | E |
| Comparative Example D-2 | — | 9 | 7.5 | 4.2 | E | E | E | E |

<Electrifiability>
E: Excellent (−20 μC/g or lower)
A: Good (−19.9 to −10.0 μC/g)
B: Usable (−9.9 to −5.0 μC/g)
C: Unusable (−4.9 μC/g or higher)

Example D-17

<Deinking Property Test>

Test paper was produced by forming test images with a black and white ratio of 6% on the paper surface of 75 g/m$^2$ by using the black toners (1) to (9) obtained in Examples D-9 to D-16 and Comparative Example D-2. A hand-made sheet for evaluation was produced with following conditions by using the test paper.

Disaggregation: An aqueous dispersion of the following composition was stirred in a beaker at 50° C. for 20 minutes to be disaggregated.

Test paper 5.0%
NaOH 0.7%
Sodium silicate 3.0%
$H_2O_2$ 1.0%
Deinking agent (from Lion Corporation, "Liptol S 2800") 0.2%

Dilution/dehydration/kneader treatment: Water was added to the above aqueous dispersion to dilute to 5%. The mixture was dehydrated centrifugally, and pulp, sodium silicate and the like were added to make the proportion of 20% of pulp, 3.0% of sodium silicate, and 0.5% of NaOH and disaggregated by a kneader.

Aging: The kneader-disaggregated product was aged at 50° C. for 2 hours.

Flotation: Water was added to the aged product to prepare a dispersion with pulp concentration of 1%, and fine bubbles were discharged into the dispersion for 7 minutes. The toner in the solution was adsorbed to the bubbles and floated on the water surface to separate the toner and water.

Washing: 2.4 g of pulp subjected to deinking was washed with two portions of 1 liter of water.

Preparation of hand-made sheet for test: A hand-made sheet (basis weight 100 g/m$^2$) was produced by a tappet sheet machine.

Evaluation of deinking property: The number of the toners existing in 9 cm$^2$ of the hand-made sheet was evaluated visually and microscopically by classifying the toners into two sizes of 100 μm or larger (visible visually) and 60 to 100 μm.

The results of the above test are shown in Table 19. The values in the table indicate the number of the remaining toners.

TABLE 19

Results of deinking property test

|  | 60 to 100 μm Number | 100 μm or larger Number | Total Number |
| --- | --- | --- | --- |
| Example D-9 | 12 | 10 | 22 |
| Example D10 | 11 | 9 | 20 |
| Example D11 | 8 | 9 | 17 |
| Example D12 | 7 | 9 | 16 |
| Example D13 | 13 | 15 | 28 |
| Example D14 | 10 | 13 | 23 |
| Example D15 | 11 | 14 | 25 |
| Example D16 | 9 | 11 | 20 |
| Comparative Example D-2 | 43 | 38 | 81 |

Example D-18

<Biodegradability Test>

Red toners (1) to (8), black toners (1) to (8), comparative red toner (9), and comparative black toner (9) were melt-molded to films with thickness of about 50 μm and buried in the soil for 6 months. As a result, films of red toners (1) to (8) and black toners (1) to (8) lost the shapes completely. On the other hand, the shapes of comparative red toner (9) and comparative black toner (9) remain intact.

Examples D-19 to D-34 and Comparative Examples D-3 and D-4

First, an image forming apparatus used in the image forming methods of Examples D-19 to D-34 and Comparative Examples D-3 and D-4 will be described. FIG. 1 is a schematic explanatory view of the cross section of an image forming apparatus for carrying out the image forming methods of Examples and Comparative Examples of the present invention. A photoconductor drum 1 shown in FIG. 1 has a photosensitive layer 1a having an organic photo semiconductor on a substrate 1b, and is conFig.d to rotate in the direction indicated by the arrow, and its surface is electrically charged at a potential of about −600 V by a charge roller 2 being a charge member situated opposite to the photoconductor drum 1 and contacting and rotating with the drum. As shown in FIG. 1, the charge roller 2 has a cored bar 2b covered with a conductive elastic layer 2a.

Figure 2:
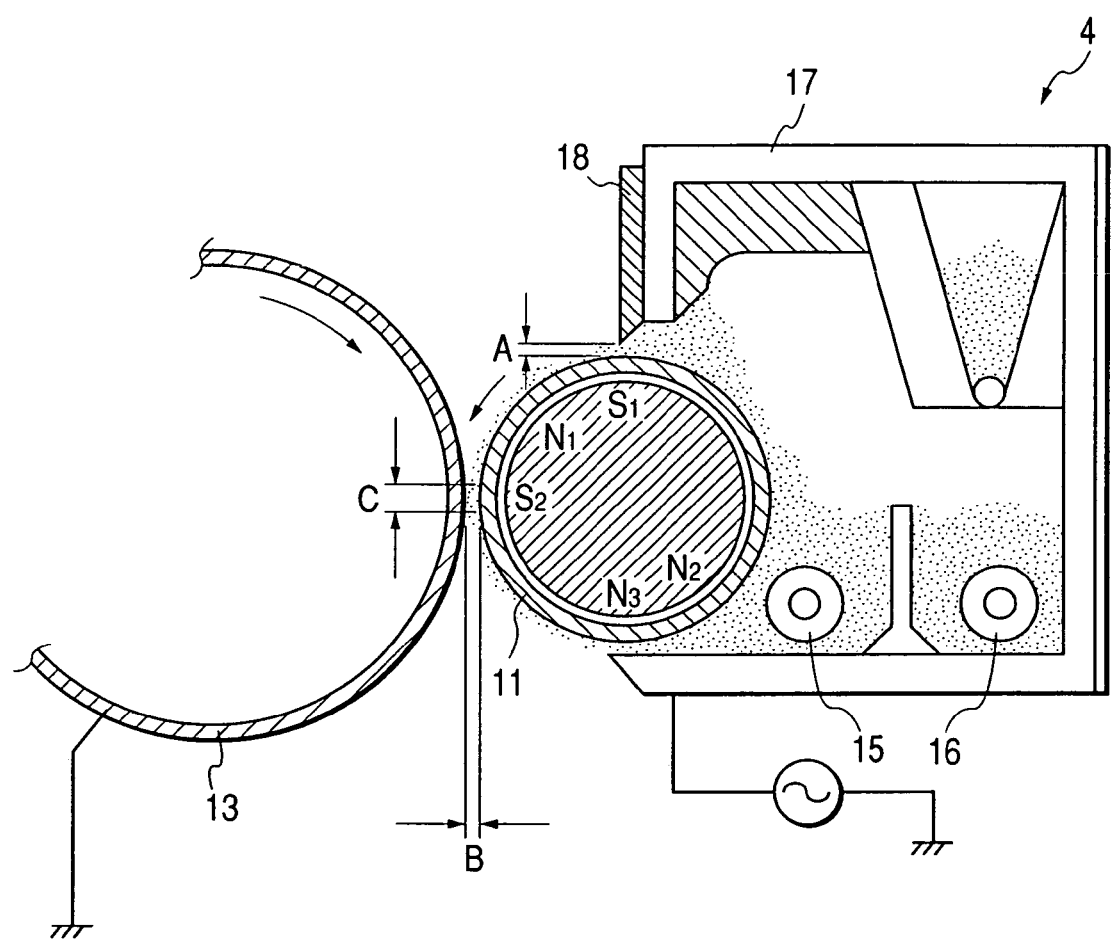
FIG. 2 is a sectional view of a principal part of a development apparatus for a two-component developer used in Examples D-19 to D-34 and Comparative Examples D-3 and D-4.

Next, the photoconductor drum 1 with its surface electrically charged is exposed to light 3 and at this time, on/off operations are performed on the photoconductor by a polygon mirror according to digital image information, whereby an electrostatic latent image with the potential of the exposed area being −100 V and the potential of the dark area being −600 V is formed. Subsequently, this electrostatic latent image on the photoconductor drum 1 is reverse-developed and thereby actualized using a plurality of development apparatuses 4-1, 4-2, 4-3 and 4-4, and thus a toner image is formed on the photoconductor drum 1. At this time, the two-component type developers obtained in Examples D-1 to D-16 and Comparative Examples D-1 and D-2 were respectively used as developers to form a toner image with a magenta toner or a black toner. FIG. 2 is an enlarged sectional view of principal parts of development apparatuses 4 for two-component type developers used at that time. Then, the toner image on the photoconductor drum 1 is transferred to an intermediate transfer body 5 contacting and rotating with the photoconductor drum 1. As a result, a four-color color combination developed image is formed on the intermediate transfer body 5. A non-transferred toner remaining on the photoconductor drum 1 without being transferred is collected in a container 9 for residual toners by a cleaner member 8.

The intermediate transfer body 5 is constituted by a cored bar 5b as a support and an elastic layer 5a provided thereon as shown in FIG. 1. In this Example, the intermediate transfer body 5 having the cored bar 5b coated with the elastic layer 5a with a carbon black as a conductivity producer sufficiently dispersed in nitrile-butadiene rubber (NBR) was used. The degree of hardness of the elastic layer 5a measured in accordance with "JIS K-6301" was 30 degrees, and the volume resistivity was $10^9$ Ω.cm. The level of transfer current required for transferring the image from the photoconductor drum 1 to the intermediate transfer body 5 is about 5 μA, and this level of current was obtained by adding a voltage of +500 V to the cored bar 5b.

The four-color toner color combination visible image formed on the intermediate transfer body 5 is transferred to an object transferring material such as a paper by a transfer roller 7, and is thereafter fixed by a heat-fixation apparatus H. The transfer roller 7 is provided thereon the core metal 7b with the outside diameter of 10 mm on which an elastic layer 7a is formed by coating of a foam of ethylene-propylene-diene based tridimensional copolymer (EPDM) dispersing carbon sufficiently therein as a conductivity producing material. The layer had a volume specific resistance of $10^6$Ω.cm and a hardness degree of 35° as measured in accordance with "JIS K-6301". In addition, a voltage was applied to this transfer roller 7 to pass a transfer current of 15 μA therethrough.

Figure 5:
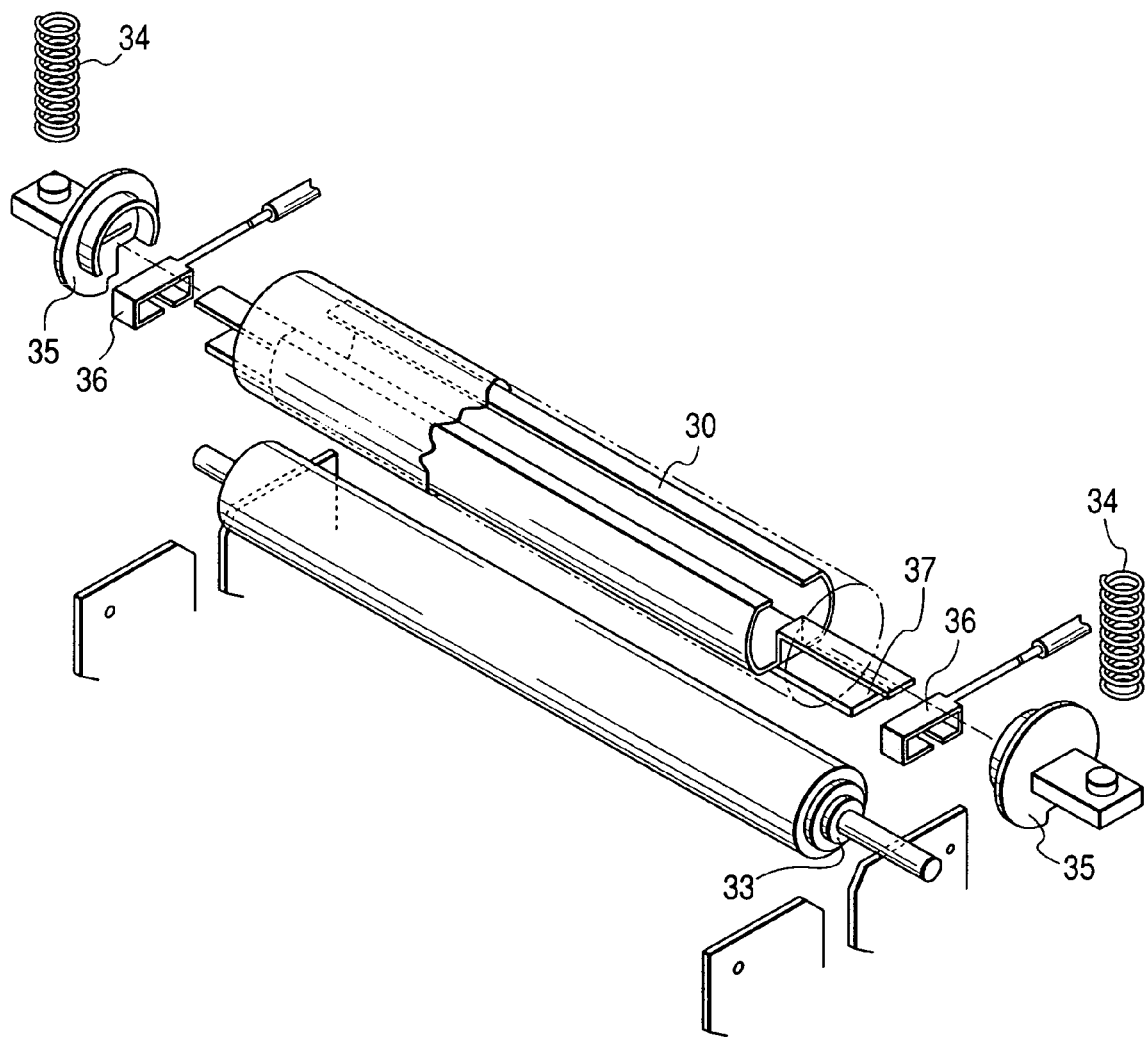
FIG. 5 is an exploded perspective view of a principal part of a fixation apparatus used in the Examples of the present invention.
Figure 6:
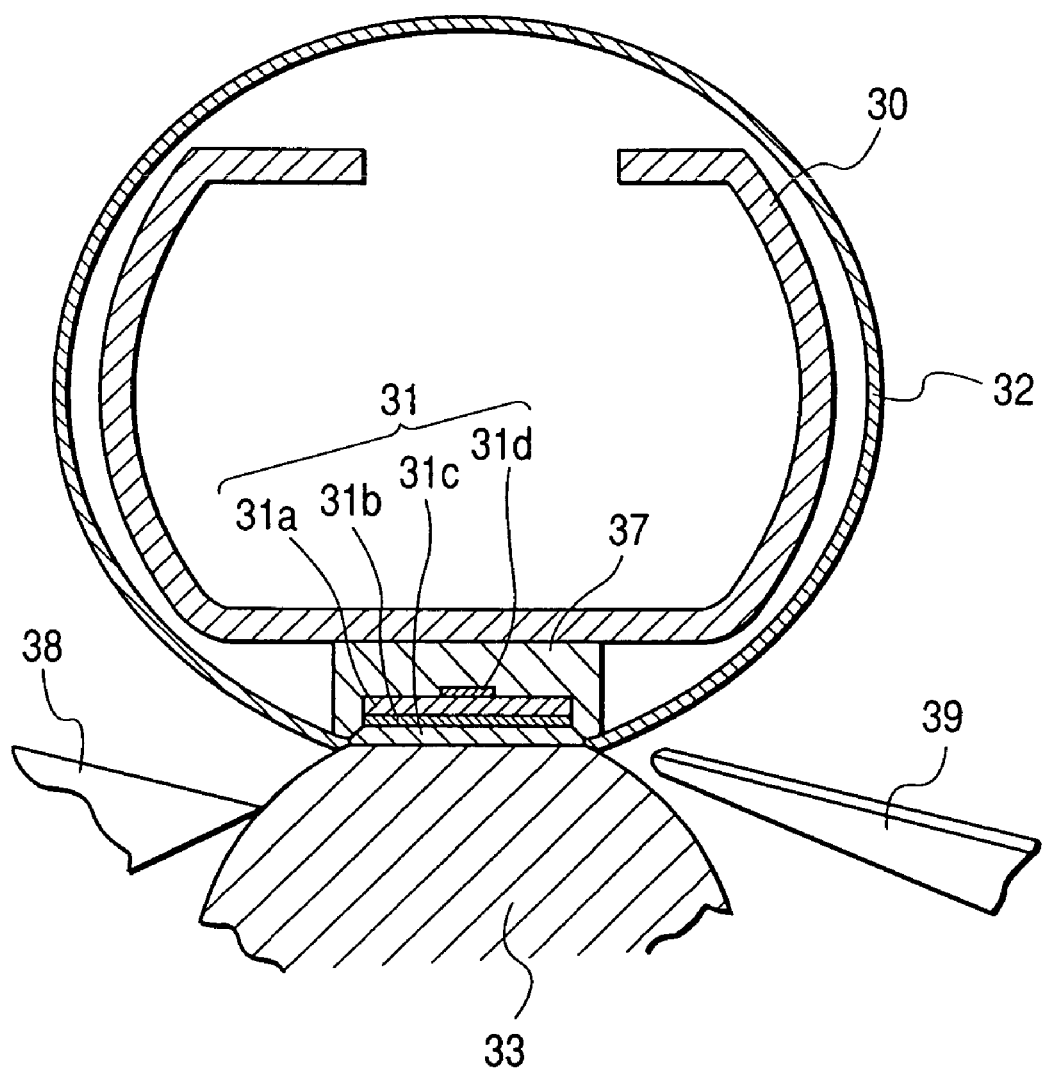
FIG. 6 is an enlarged sectional view of a principal part showing a film state of the fixation apparatus used in the Examples of the present invention at the time when it is not driven.

In the apparatus shown in FIG. 1, a fixation apparatus of heated roll type having no oil coating mechanism shown in FIGS. 5 and 6 was used in the heat-fixation apparatus H. The both upper and lower rollers of the fixation apparatus used here had surface layers made of fluorine based resin. In addition, the diameter of the roller was 60 mm. The fixation temperature for fixation was 160° C., and the nipping width was set at 7 mm. Furthermore, a transfer residual toner on the photoconductor drum 1, which was collected by cleaning, was transported to a developing device by a reuse mechanism for reuse.

<Evaluation>

Two-component type developers produced using the toners of Examples D-1 to D-16 and two-component type developers produced using toners of Comparative Examples D-1 and D-2 were used, respectively, to perform printout testing at a printout rate of 8 sheets (A4 size) per minute while the developer was supplied one after another in a monochromatic intermittent mode (namely a mode in which the developing device is stopped for 10 seconds for each printout to accelerate the degradation of a toner in a preliminary operation during restart of the device) at a normal temperature and normal humidity (25° C., 60% RH) and a high temperature and high humidity (30° C., 80% RH) under the conditions described above, and resulting printout images were evaluated for the following items. The evaluation results are shown together in Table 20.

(Evaluation of Printout Images)

1. Image Density

Images were printed out on a predetermined number of normal copying papers (75 g/m$^2$), and the image density was evaluated according to the level at which the density of the image from the final printout was retained with respect to the density of the initial image. Furthermore, for the measurement of image density, a Macbeth reflective densitometer (manufactured by Macbeth Co., Ltd.) was used to measure a density relative to that of the printout image on a white ground with the density of original copy equal to 0.00.

E: Excellent (image density from the final printout is 1.40 or greater)
A: Good (image density from the final printout is 1.35 or greater and lower than 1.40)
B: Usable (image density from the final printout is 1.00 or greater and lower than 1.35)
C: Unusable (image density from the final printout is lower than 1.00)

2. Image fog

Images were printed out on a predetermined number of normal copying papers (75 g/m$^2$), and the image fog was evaluated with a solid white image from the final printout. Specifically, the evaluation was made as follow: the worst value of the reflective density of the white ground after printing and the average reflective density of the paper before printing, as measured using a reflective densitometer (Reflectometer ODEL TC-6DS manufactured by Tokyo Denshoku Co., Ltd.), were defined as DS and Dr, respectively, (Ds-Dr) was calculated from these values as a fog level to make an evaluation according to the following criterion.

E: Excellent (fog level is 0% or higher and lower than 1.5%)
A: Good (fog level is 1.5% or higher and lower than 3.0%)
B: Usable (fog level is 3.0% or higher and lower than 5.0%)
C: Unusable (fog level is 5.0% or higher)

3. Transferability

Solid black images were printed out on a predetermined number of normal copying papers (75 g/m$^2$), and the image dislocation level of the image from the final printout was visually observed to make an evaluation according to the following criterion.

E: Excellent (almost not observed)
A: Good (slightly observed)
B: Usable
C: Unusable In addition, in Examples D-19 to D-34 and Comparative Examples D-3 and D-4, occurrences of scars and sticking residual toners on the surfaces of the photoconductor drum and intermediate transfer body, and their influence on printout images (matching with the image forming apparatus) were visually evaluated after 5000 images were outputted, and as the result, scars and sticking residual toners on the surfaces of the photoconductor drum and intermediate transfer body were not observed, and thus matching with the image forming apparatus was excellent.

28 having a surface roughness Ra of 1.1 with the surface coated with a resin having a carbon black dispersed thereon was used.

An enlarged sectional view of the principal part of the development apparatus for one-component type developers used in Example D-35 to Example D-52 and Comparative

TABLE 20

Evaluation result of printout image

| Examples/ Comparative Examples | Two-component type developer | Normal temperature and normal humidity | | | High temperature and high humidity | | |
|---|---|---|---|---|---|---|---|
| | | Image density | Image fog | Transfer-ability | Image density | Image fog | Transfer-ability |
| D-19 | Red 1 | E | A | E | E | A | E |
| D-20 | Red 2 | E | A | E | E | A | A |
| D-21 | Red 3 | E | E | E | E | E | E |
| D-22 | Red 4 | E | E | E | E | E | E |
| D-23 | Red 5 | E | A | E | E | A | E |
| D-24 | Red 6 | E | A | E | E | A | A |
| D-25 | Red 7 | E | E | E | E | E | E |
| D-26 | Red 8 | E | E | E | E | E | E |
| D-27 | Black 1 | E | A | E | E | A | E |
| D-28 | Black 2 | E | A | E | E | A | A |
| D-29 | Black 3 | E | E | E | E | E | E |
| D-30 | Black 4 | E | E | E | E | E | E |
| D-31 | Black 5 | E | A | E | E | A | E |
| D-32 | Black 6 | E | A | E | E | A | A |
| D-33 | Black 7 | E | E | E | E | E | E |
| D-34 | Black 8 | E | E | E | E | E | E |
| Comparative Example D-3 | Red 9 | E | E | E | E | E | E |
| Comparative Example D-4 | Black 9 | E | E | E | E | E | E |

Example D-35 to Example D-42, Comparative Example D-5 and Comparative Example D-6

Figure 3:
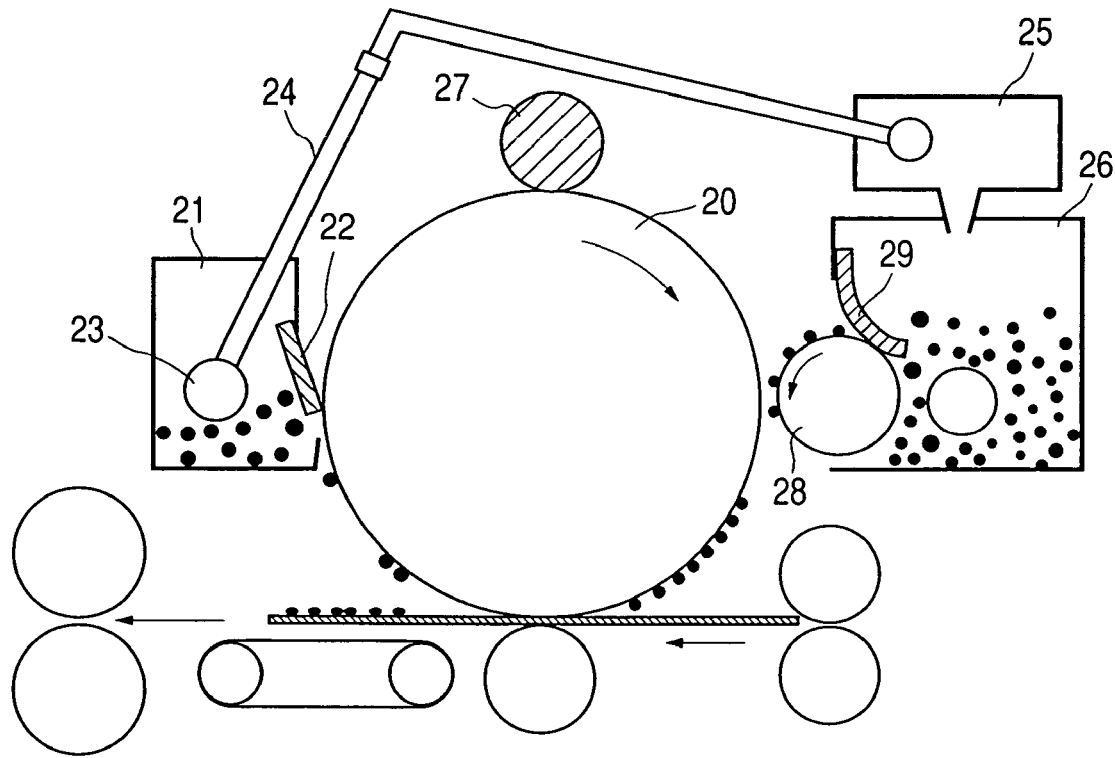
FIG. 3 is a schematic explanatory view of an image forming apparatus having a reuse mechanism of a toner used in Examples D-35 to D-42 and Comparative Examples D-5 and D-6.

For carrying out the image forming methods of Example D-35 to Example D-42 and Comparative Example D-5 and Comparative Example D-6, the toners obtained in Examples D-9 to D-16 and Comparative Examples D-1 and D-2 were used respectively as developers. In addition, for means for forming an image, an image forming apparatus with a commercially available laser beam printer LBP-EX (from Canon Inc.) modified so that it was provided with a reuse mechanism and reset as shown in FIG. 3 was used. That is, the image forming apparatus shown in FIG. 3 is provided with a system in which a non-transferred toner remaining on the photoconductor drum 20 after the transfer process is scraped off by an elastic blade 22 of a cleaner 21 abutting against the photoconductor drum 20, then sent into the cleaner 21 by a cleaner roller, passed through a cleaner reuse 23, and returned to the development device 26 via a hopper 25 by a supply pipe 24 with a carrier screw mounted thereon, and the toner collected in this way is reused.

Figure 4:
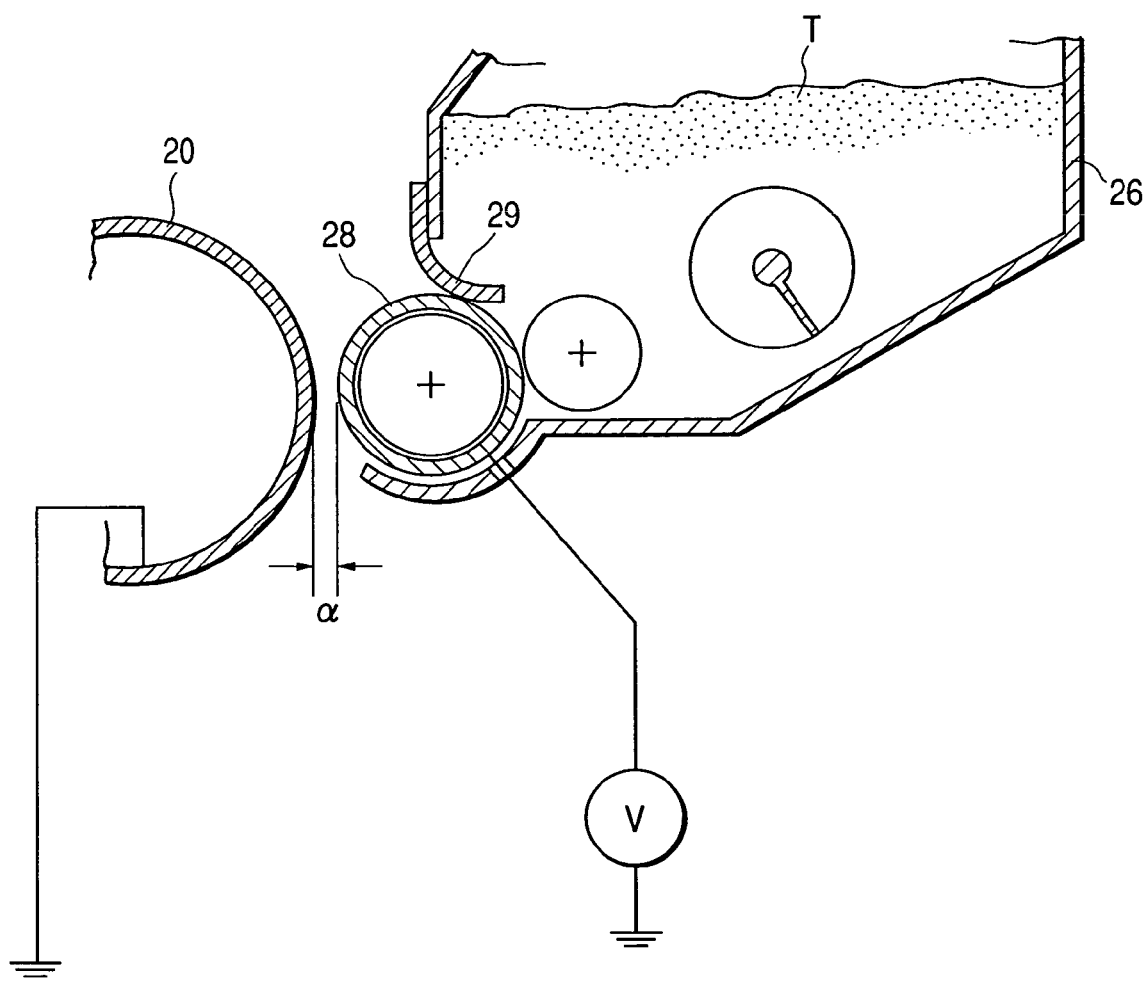
FIG. 4 is a sectional view of a principal part of a development apparatus for a one-component developer used in Examples D-35 to D-42 and Comparative Examples D-5 and D-6.

In the image forming apparatus shown in FIG. 3, the surface of the photoconductor drum 20 is electrically charged by a primary charge roller 27. A rubber roller (diameter 12 mm, abutment pressure 50 g/cm) coated with a nylon resin and having conductive carbon dispersed therein was used for the primary charge roller 27, and an electrostatic latent image with a dark area potential VD of −700 V and a light area potential VL of −200 V was formed on the electrostatic latent image carrier (photoconductor drum 20) by laser exposure (600 dpi, not shown). As a toner carrier, a development sleeve Example D-5 and Comparative Example D-6 is shown in FIG. 4. For conditions for developing electrostatic latent images, the speed of the development sleeve 28 was set at a speed 1.1 times as high as the movement speed of the surface of the photoconductor drum 20 opposite thereto, and the space α between the photoconductor drum 20 and the development sleeve 28 (between S and D) was 270 μm. For the member for controlling the thickness of the toner layer, an abutting urethane rubber blade 29 was used. In addition, the set temperature of the heat-fixation apparatus for fixing a toner image was 160° C. Furthermore, for the fixation apparatus, a fixation apparatus shown in FIG. 5 and FIG. 6 was used. In FIG. 32, the part referred to with a reference numeral 32 is tension free.

As described above, under the condition of normal temperature and normal humidity (25° C., 60% RH), images were printed out on up to 30,000 sheets at a printout rate of 8 sheets (A4 size) per minute while the toner was supplied one after another in a continuous mode (namely, a mode in which the development device is not stopped, thereby promoting consumption of the toner), and the densities of resulting printout images were measured to evaluate the durability of the image according to the following criteria. In addition, the image from the 10,000th printout was observed to make an evaluation about image fog according to the following criteria. At the same time, situations of the components comprising the image forming apparatus after the durability testing were observed to evaluate matching between each component and the above toners. The results thereof are shown together in Table 21. Change in image density during endurance Images were printed out on a predetermined number of normal copying papers (75 g/m²), and the image density was evaluated according to the level at which the density of the image from the final printout was retained with respect to the density of the initial image. Furthermore, for the measurement of image density, a Macbeth reflective densitometer (from Macbeth Co., Ltd.) was used to measure a density relative to that of the printout image on a white ground with the density of original copy equal to 0.00 for evaluation.

E: Excellent (image density from the final printout is 1.40 or greater)
A: Good (image density from the final printout is 1.35 or greater and lower than 1.40)
B: Usable (image density from the final printout is 1.00 or greater and lower than 1.35)
C: Unusable (image density from the final printout is lower than 1.00)

Image Fog

Images were printed out on a predetermined number of normal copying papers (75 g/m$^2$), and the image fog was evaluated with a solid white image from the final printout. Specifically, the evaluation was made as follows: the worst value of the reflective density of the white ground after printing and the average reflective density of the paper before printing, as measured using a reflective densitometer (Reflectometer ODEL TC-6DS from Tokyo Denshoku Co., Ltd.), were defined as Ds and Dr, respectively, and (Ds-Dr) was calculated from these values as a fog level to make an evaluation according to the following criteria.

E: Excellent (fog level is 0% or higher and lower than 1.5%)
A: Good (fog level is 1.5% or higher and lower than 3.0%)
B: Usable (fog level is 3.0% or higher and lower than 5.0%)
C: Unusable (fog level is 5.0% or higher) Evaluation of matching with image forming apparatus 1. Matching with Development Sleeve After the printout testing was completed, the situation of residual toners sticking to the surface of the development sleeve and their influence on the printout image were visually evaluated.

E: Excellent (not observed)
A: Good (almost not observed)
B: Usable (sticking residual toners are observed but the influence on the image is not significant)
C: Unusable (sticking of residual toners is significant, causing unevenness in the image)

2. Matching with Photoconductor Drum

Occurrences of scars and sticking residual toners on the surface of the photoconductor drum and their influence on the printout image were visually evaluated.

E: Excellent (not observed)
A: Good (scars are slightly observed but no influence on the image)
B: Usable (sticking residual toners and scars are observed but the influence on the image is not significant)
C: Unusable (sticking of residual toners is significant, causing longitudinal striped defects in the image)

3. Matching with Fixation Apparatus

The surface situation of the fixation film was observed, and the results of surface characteristics and occurrences of sticking residual toners were collectively averaged to evaluate the durability of the film.

(1) Surface Characteristics

Occurrences of scars and flaking on the surface of the fixation film were visually observed and evaluated after the printout testing was completed.

E: Excellent (not observed)
A: Good (almost not observed)
B: Usable
C: Unusable (2) Situation of Sticking Residual Toners The situation of residual toners sticking to the surface of the fixation film was visually observed and evaluated after the printout testing was completed.

E: Excellent (not observed)
A: Good (almost not observed)
B: Usable
C: Unusable

TABLE 21

Evaluation results of printout image and matching with image forming apparatus

| | | Evaluation of printout image | | | | Evaluation of matching with each apparatus | | | |
|---|---|---|---|---|---|---|---|---|---|
| | | Change in image density during endurance | | | 10 thousands | | Photo- | Fixation apparatus | |
| Examples | Toner | Initial | 10 Thousand | 10 thousands | 30 thousands | fogged images | Development sleeve | conductor drum | Surface characteristic | Toner fixation |
| D-35 | Black 1 | E | E | E | A | E | E | E | E | A |
| D-36 | Black 2 | E | E | A | A | E | E | E | E | A |
| D-37 | Black 3 | E | E | E | E | E | E | E | E | E |
| D-38 | Black 4 | E | E | E | E | E | E | E | E | E |
| D-39 | Black 5 | E | E | E | A | E | E | E | E | A |
| D-40 | Black 6 | E | E | A | A | A | E | A | E | A |
| D-41 | Black 7 | E | E | E | E | E | E | E | E | E |
| D-42 | Black 8 | E | E | E | E | E | E | E | E | E |
| Comparative Example D-5 | Red 9 | E | E | E | E | E | E | E | E | E |
| Comparative Example D-6 | Black 9 | E | E | E | E | E | E | E | E | E |

Example D-43

Printout testing was performed in the same manner as in Example D-42 except that the toner reuse mechanism of the image forming apparatus of FIG. 3 was removed and a printout rate was set to 16 sheets (A4 size) per minute, while the black toner (1) of Example D-1 was supplied one after another in a continuous mode (namely, a mode in which the development device is not stopped, thereby promoting consumption of the toner). The resultant printout images and the matching with the image forming apparatus used were evaluated in the same items as those of Example D-35 to Example D-42 and Comparative Example D-5 and Comparative Example D-6. As a result, good results were obtained for all the items.

The invention claimed is:

1. A polyhydroxyalkanoate copolymer comprising at least, per polymer molecule, one kind of unit selected from the group consisting of chemical formulae (1) and (2):

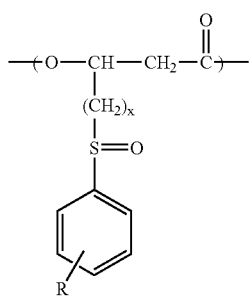

(1)

X = 1–7

(wherein R is any one selected from the group consisting of H, halogen, CN, $NO_2$, COOR', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for each unit)

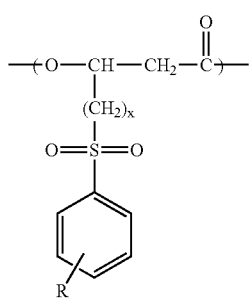

(2)

X = 1–7

(wherein R is any one selected from the group consisting of H, halogen, CN, $NO_2$, COO R', $SO_2R''$ (R' is any one selected from the group consisting of H, Na, K, $CH_3$ and $C_2H_5$; R'' is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for unit)

and at least one unit selected from the group consisting of chemical formulae (3) to (6):

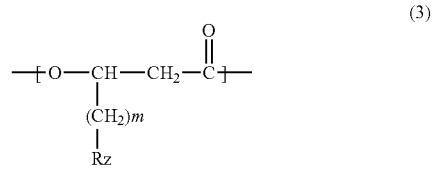

(3)

m = 1–8

(wherein m is an integer selected from the range shown in the same chemical formula; wherein Rz in chemical formula (3) is any one residue selected from the group consisting of chemical formulae (8), (9), (10), (12), (13), (14) and (15):

(8)

(wherein $R_1$ is any one selected from the group consisting of H, halogen, CN, $NO_2$, COOR' except the substituent introduced into the para-position of the phenyl group (R' is any one selected from the group consisting of H, Na and K), $CH_3$, $C_2H_5$, $C_3H_7$, $CF_3$, $C_2F_5$ and $C_3F_7$, and when more than one unit exist, $R_1$ of each unit can represent any one of the substituents described above independently)

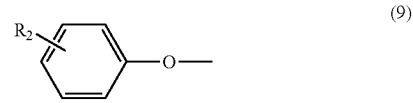

(9)

(wherein $R_2$ is any one selected from the group consisting of H, halogen, CN, $NO_2$, $CH_3$, $C_2H_5$, $C_3H_7$, $SCH_3$, $CF_3$, $C_2F_5$ and $C_3F_7$, and when more than one unit exist, $R_1$ of each unit can represent any one of the substituents described above independently)

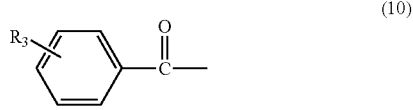

(10)

(wherein $R_3$ is any one selected from the group consisting of H, halogen, CN, $NO_2$, $CH_3$, $C_2H_5$, $C_3H_7$, $CF_3$, $C_2F_5$ and $C_3F_7$, and when more than one exist, $R_3$ of each unit can represent any one of the substituents described above independently)

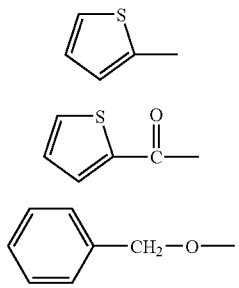

and when more than one unit exist, m and Rz of each unit can independently represent any one of the integers and the substituents described above, respectively)

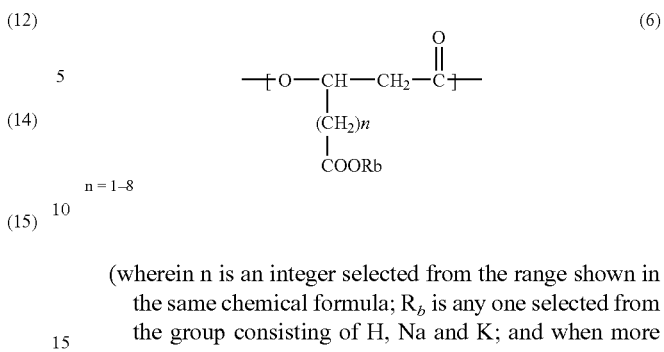

(wherein $R_a$ is any one selected from the group consisting of H, CN, $NO_2$, halogen, $CH_3$, $C_2H_5$, $C_3H_7$, $CF_3$, $C_2F_5$ and $C_3F_7$; k is an integer selected from the range shown in the same chemical formula; and when more than one unit exist, k and $R_a$ of each unit can independently represent any one of the integers and the substituents described above, respectively)

(5)

—(O—CH—CH$_2$—C)—
          |              ||
       (CH$_2$)n         O
          |
         CH
          ||
         CH$_2$ n = 1–8

(wherein n is an integer selected from the range shown in the same chemical formula, and when more than one unit exist, n of each unit can represent any one of the integers described above independently)

(6)

—(O—CH—CH$_2$—C)—
          |              ||
       (CH$_2$)n         O
          |
        COORb n = 1–8

(wherein n is an integer selected from the range shown in the same chemical formula; $R_b$ is any one selected from the group consisting of H, Na and K; and when more than one unit exist, n and Rb of each unit can independently represent any one of the integers and the substituents described above, respectively).

2. The polyhydroxyalkanoate copolymer according to claim 1, further comprising, per polymer molecule, at least one unit selected from the group consisting of 3-hydroxy-(substituted phenylsulfanyl)alkanoic acid units having chemical formula (7):

(7)

—(O—CH—CH$_2$—C)—
          |              ||
       (CH$_2$)x         O
          |
          S
          |
         (phenyl)-R

X = 1–7

(wherein R is any one selected from the group consisting of H, halogen, CN, $NO_2$, COO R', $SO_2R''$ (R' is any one selected from the group consisting of H, Na, K, $CH_3$ and $C_2H_5$; R" is any one selected from the group consisting of OH, ONa, OK, halogen, $OCH_3$ and $OC_2H_5$), $CH_3$, $C_2H_5$, $C_3H_7$, $(CH_3)_2$—CH and $(CH_3)_3$—C, and when more than one unit exist, R of each unit can represent any one of the substituents described above independently; and x is an integer selected from 1 to 7 and can differ for unit).

3. The polyhydroxyalkanoate copolymer according to claim 1, which has a number average molecular weight of 1,000 to 1,000,000.

* * * * *